United States Patent
Zhang

(10) Patent No.: US 9,695,178 B2
(45) Date of Patent: Jul. 4, 2017

(54) 6-(2-PYRIDYL)-7,8-DIHYDRO-5H-PYRIDO[4,3-D]PYRIMIDINE ANALOGS AS HEDGEHOG PATHWAY SIGNALING INHIBITORS AND THERAPEUTIC APPLICATIONS THEREOF

(71) Applicant: Suzhou Yunxuan Yiyao Keji Youxian Gongsi, Suzhou (CN)

(72) Inventor: Xiaohu Zhang, Suzhou (CN)

(73) Assignee: Suzhou Kintor Pharmaceuticals, Inc., Suzhou (CN)

( * ) Notice: Subject to any disclaimer, the term of this patent is extended or adjusted under 35 U.S.C. 154(b) by 0 days.

(21) Appl. No.: 14/761,166

(22) PCT Filed: Dec. 20, 2013

(86) PCT No.: PCT/US2013/077305
§ 371 (c)(1),
(2) Date: Jul. 15, 2015

(87) PCT Pub. No.: WO2014/113191
PCT Pub. Date: Jul. 24, 2014

(65) Prior Publication Data
US 2016/0024095 A1    Jan. 28, 2016

(30) Foreign Application Priority Data

Jan. 15, 2013  (CN) .......................... 2013 1 0014254
Feb. 25, 2013  (CN) .......................... 2013 1 0057744
Oct. 8, 2013   (CN) .......................... 2013 1 0463448
Oct. 8, 2013   (CN) .......................... 2013 1 0465383
Oct. 16, 2013  (CN) .......................... 2013 1 0485380

(51) Int. Cl.
C07D 487/04    (2006.01)
C07D 513/04    (2006.01)
C07D 498/04    (2006.01)
C07D 471/04    (2006.01)

(52) U.S. Cl.
CPC ......... *C07D 487/04* (2013.01); *C07D 471/04* (2013.01); *C07D 498/04* (2013.01); *C07D 513/04* (2013.01)

(58) Field of Classification Search
CPC .. C07D 487/04; C07D 513/04; C07D 498/04; C07D 471/04
See application file for complete search history.

(56) References Cited

U.S. PATENT DOCUMENTS 7,789,958 B2 * 9/2010 Sturgill .............. C01G 45/1221
                                                    106/14.05

* cited by examiner

*Primary Examiner* — Alexander R Pagano
*Assistant Examiner* — Ebenezer O Sackey
(74) *Attorney, Agent, or Firm* — Feng Tian

(57) ABSTRACT

The hedgehog (Hh) signaling pathway is a pathway which regulates patterning, growth and cell migration during embryonic development, but in adulthood is limited to tissue maintenance and repair. Mutational inactivation of the inhibitory pathway components leads to constitutive ligand-independent activation of the Hh signaling pathway, results in cancers such as basal cell carcinoma and medulloblastoma. Ligand-dependent activation of Hh signaling is involved in prostate cancer, pancreatic cancer, breast cancer and some blood cancers. Therefore, inhibition of the aberrant Hh signaling represents a promising approach toward novel anticancer therapy. The present invention provides novel molecules of formula I that inhibit hedgehog pathway signaling and provides therapeutic applications for the treatment of malignancies (basal cell carcinoma, medulloblastoma, glioblastoma, non-small cell lung cancer, prostate cancer, pancreatic cancer, blood cancers, mesenchymal cancers, etc.), prevention of tumor regrowth, sensitization of radio-chemo therapies, and other diseases (inflammation, fibrosis and immune disorders) related to hedgehog signaling.

8 Claims, 2 Drawing Sheets

6-(2-PYRIDYL)-7,8-DIHYDRO-5H-PYRIDO[4,3-D]PYRIMIDINE ANALOGS AS HEDGEHOG PATHWAY SIGNALING INHIBITORS AND THERAPEUTIC APPLICATIONS THEREOF

CROSS REFERENCE TO RELATED APPLICATIONS

This application claims the benefit of Chinese Patent Applications 201310014254.4, filed on Jan. 15, 2013; 201310057744.2, filed on Feb. 25, 2013; 201310465383.5, filed on Oct. 8, 2013; 201310463448.2, filed on Oct. 8, 2013; and 201310485380.8, filed on Oct. 16, 2013; all of which are hereby incorporated by reference.

FIELD OF INVENTION

The present invention generally relates to heterocyclic compounds and, more particularly, relates to novel heterocyclic compounds that are useful in therapies targeting the hedgehog signaling pathway mediated diseases, such as cancer, in mammals.

BACKGROUND OF THE INVENTION

The hedgehog (Hh) signaling pathway is a key developmental pathway which regulates patterning, growth and cell migration during embryonic development, but in adulthood is limited to tissue maintenance and repair. Under normal conditions, the endogenous ligands sonic hedgehog, Indian hedgehog and desert hedgehog bind to their receptor Patched (Ptch) which in turn relieves the inhibitory effect of Ptch on smoothened (Smo). Smo activation triggers a series of events ultimately lead to specific gene expression mediated by the Gli family transcription factors (Jiang and Hui, *Dev. Cell Review* (2008) 15:801-812). Aberrant Hh signaling has been linked to numerous human cancers. Mutational inactivation of the inhibitory pathway components leads to constitutive ligand-independent activation of the Hh signaling pathway, results in cancers such as basal cell carcinoma and medulloblastoma (Xie et al., *Nature* (1998) 391:90-92), glioblastoma (Bar et al. *Stem Cells* (2007) 25(10):2524-33; Filbin et al. *Nature Medicine* (2013) dio:10.1038/nm.3328). Ligand-dependent activation of Hh signaling is involved in prostate cancer (Sanchez et al. *PNAS* 101(2004) (34):12561-566), pancreatic cancer (Thayer et al. *Nature* (2003) 423:851-856), breast cancer (Kubo et al. *Cancer Res.* (2003) 64:6071-6074), non-small cell lung cancer (Yuan et al. *Oncogene* (2007) 26:1046-1055), small cell lung cancer (Watkins et al. *Nature* (2003) 422:313-317), and some blood cancers (Scales et al., *Trends Pharmacol. Sci.* (2009) 30:303-312). Therefore, inhibition of the aberrant Hh signaling represents a promising approach toward novel anti-cancer therapy (Peukert and Miller-Moslin, *Chem Med Chem* (2010) 5:500-512).

It has been found that hedgehog signaling regulates the expression of the ABC transporter proteins multi-drug resistance protein-1 (MDR1, ABCB1, P-glycoprotein) and (BCRP, ABCG2), and that targeted knockdown of MDR1 and BCRP expression by small interfering RNA partially reverses Hh-induced chemoresistance. This indicates the Hh pathway maybe a target to overcome MDR and increase chemotherapeutic response (Sims-Mourtada et al. *Oncogene* (2007) 26:5674-79). The blockade of sonic hedgehog signaling pathway was found to enhance the antiproliferative effect of EGFR inhibitors in pancreatic cancer cells (Hu et al. *Acta Pharmacol. Sin.* (2007) 28 1224-30) and prostate cancer cells (Mimeault et al. *Int. J. Cancer* (2006) 118:1022-31).

The hedgehog pathway has also been associated with tumor regrowth after chemoradiotherapy and as a potential target to improve radiation response (Sim-Mourtada et al. *Clin. Cancer Res.* (2006) 12:6565-6572).

It has also been reported that the inhibition of the hedgehog signaling pathway may be of use for the treatment of a range of diseases related to inflammation, epithelial cell hyperplasia, fibrosis of tissue or immune disorders (Lamb et al. EP1183040).

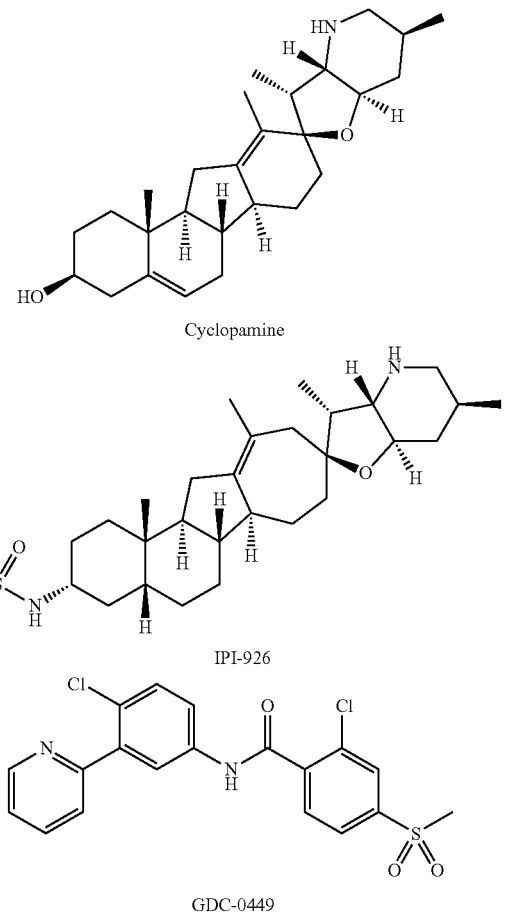

Cyclopamine

IPI-926

GDC-0449

Cyclopamine, a naturally occurring alkaloid, was the first reported Hh signaling pathway inhibitor (Cooper et al., *Science* (1998) 280:1603-1607), and later identified as Smo antagonist (Chen et al., *Genes. Dev.* (2002) 16:2743-2748). A cyclopamine derivative IPI-926, which demonstrated better potency, stability and other pharmaceutical properties than that of cyclopamine, has entered clinical development (Trembley et al., *J. Med. Chem.* (2009) 52:4400-4418). One embryonic pathway inhibitor, GDC-0449 (Robarge et al., *Bioorg. Med. Chem. Lett.* (2009) 19: 5576-5581), was approved by FDA in January 2012 for the treatment of basal cell carcinoma which is not suitable for operation.

Despite advances with these compounds, there are numerous problems. For example, GDC-0449 possesses all sp2-hybridized carbons but one, thereby resulting in high melting point (251° C.) and poor solubility (9.5 μg/mL)—the enhanced solubility was obtained by adding an ortho-chloro group to the right side ring to introduce tilt and reduce planarity of the aryl amide (Robarge et al.). It also introduced mutations in SMO and resulted rapid tumor relapse in at least one patient (Yauch et al., *Science* (2009) 326:572-574). There remains a need to develop potent hedgehog pathway inhibitors.

SUMMARY OF THE INVENTION

In one aspect, the present invention provides compounds of formula I:

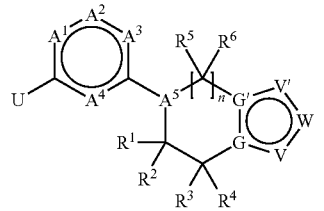

I or a pharmaceutically acceptable salt, or solvate thereof, wherein
$A^1$ to $A^5$ are independently selected from N and C—$R^7$, provided that at least one from $A^1$ to $A^4$ is N;
G and G' are independently selected from C and N;
V and V' are independently selected from N, O, S and C—$R^7$;
n is 0, 1, 2, 3, 4, 5, or 6;
$R^1$ to $R^7$ are independently selected from hydrogen, halogen, haloalkyl, CN, cyanoalkyl, trifluoromethyl, alkyl, alkenyl, alkynyl, amino, oxygen, hydroxyl, sulfur, hydrosulfuryl, alkoxy, acyloxy, acylamino, urea, carbamoyloxy, thiourea, sulfone, sulfoxide, sulfonamide, azido, alkylalkenyl, alkylalkynyl, alkylamino, alkylacyloxy, alkylsulphonyl, alkylsulfinyl, alkylsulfonamide, azidoalkyl, cycloalkyl, cycloalkenyl, 3-12 membered heterocycle, aryl, and 5-12 membered heteroaryl, wherein when both $R^5$ and $R^6$ are oxygen, $R^5$ and $R^6$ are an oxygen atom which forms a double bond (=O);
U is

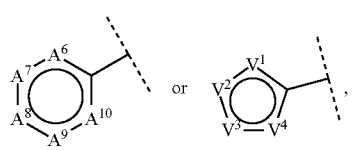

wherein $A^6$ to $A^{10}$ are independently selected from N and C—$R^7$, $V^1$ to $V^4$ are independently selected from N, O, S and C—$R^7$, provided that at least one from $V^1$ to $V^4$ is N, O or S; and
W is $V^5$, $V^6$—$V^7$, or $V^6$=$V^7$, wherein $V^5$ to $V^7$ are independently selected from N, O, S and C—$R^7$, $V^6$ connects with V', and $V^7$ connects with V.

In another aspect, herein provides compounds of formula I, wherein:
$A^1$ and $A^2$ are independently C—$R^{22}$;
$A^3$ and $A^5$ are N;
$A^4$ is N or C—$R^7$;
n is 1;
$R^1$ and $R^2$ are hydrogen;
$R^3$ and $R^4$ are independently H or methyl;

$R^5$ and $R^6$ are independently H, methyl or oxygen, wherein when both $R^5$ and $R^6$ are oxygen, $R^5$ and $R^6$ are an oxygen atom which forms a double bond (=O);
G and G' are carbon;
V and V' are independently N or C—$R^7$;
W is $V^6$—$V^7$, wherein $V^6$ is N or C—$R^7$, $V^7$ is C—$R^{23}$;
U is

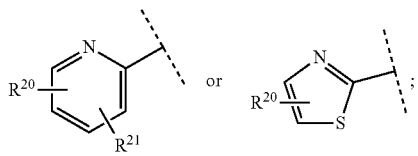

$R^{20}$ to $R^{22}$ are independently selected from hydrogen, halogen, haloalkyl, alkyl, trifluoromethyl, alkylsulfonyl, alkylsulfinyl, alkylsulfonamide, sulfonamide, and alkylacyloxy; and
$R^{23}$ is selected from the group consisting of:

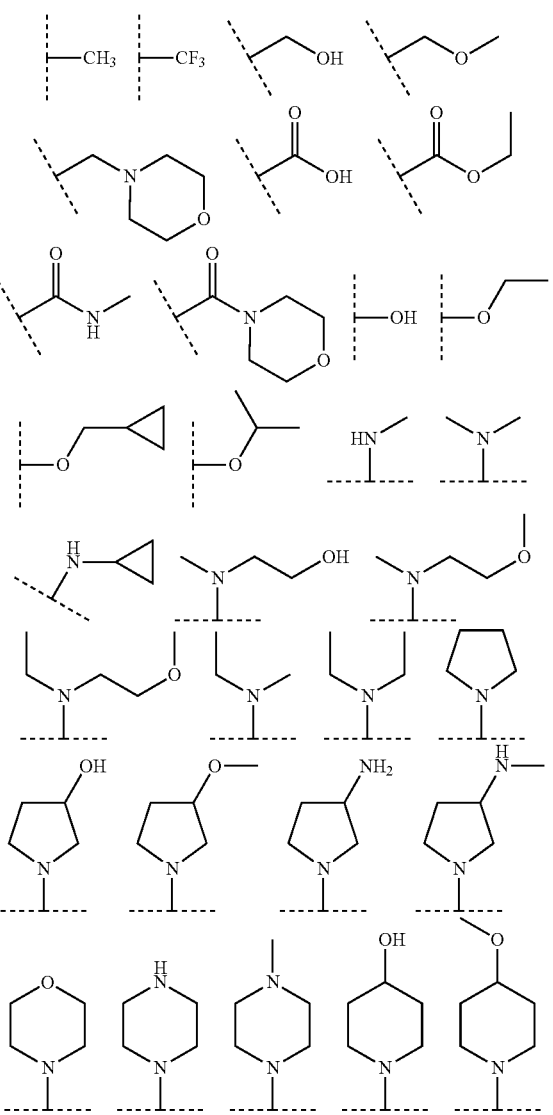

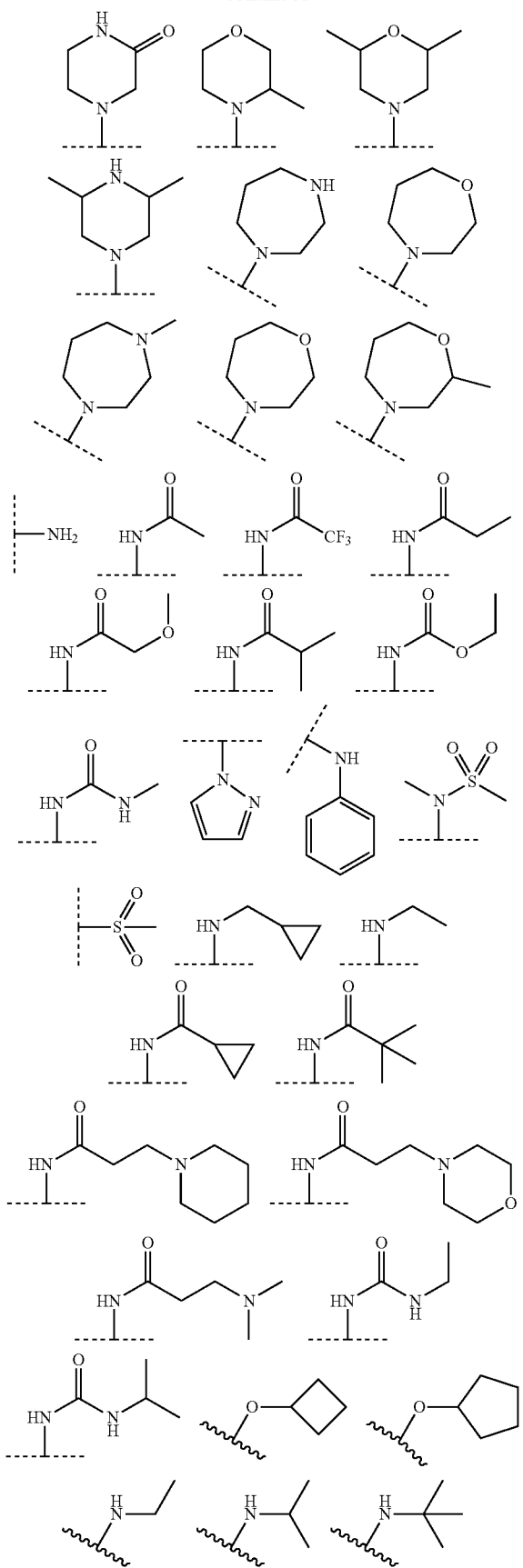

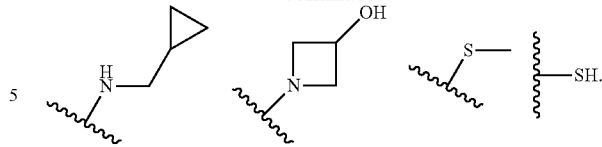

In another aspect, herein provides compounds of formula I, wherein:
- $A^1$, $A^2$ and $A^4$ are independently C—$R^{22}$;
- $A^3$ and $A^5$ are N;
- n is 1;
- $R^1$ and $R^2$ are hydrogen;
- $R^3$ and $R^4$ are independently H or methyl;
- $R^5$ and $R^6$ are independently H, methyl or oxygen, wherein when both $R^5$ and $R^6$ are oxygen, $R^5$ and $R^6$ are an oxygen atom which forms a double bond (=O);
- G and G' are carbon;
- V is N and V' is S;
- W is C—$R^9$;
- U is

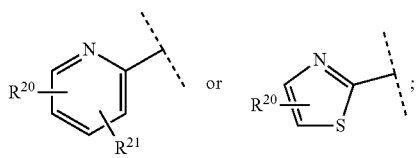

$R^{20}$ to $R^{22}$ are independently selected from hydrogen, halogen, haloalkyl, alkyl, trifluoromethyl, alkylsulfonyl, alkylsulfinyl, alkylsulfonamide, sulfonamide, and alkylacyloxy; and $R^9$ is selected from the group consisting of:

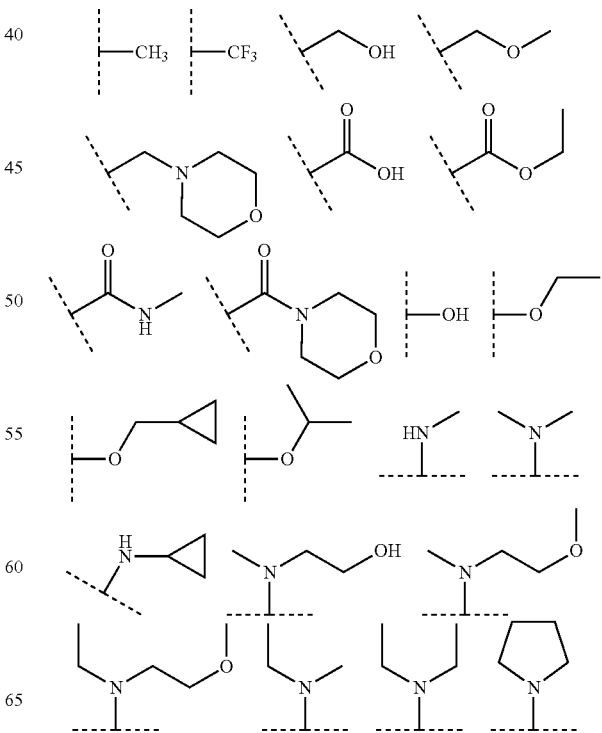

-continued

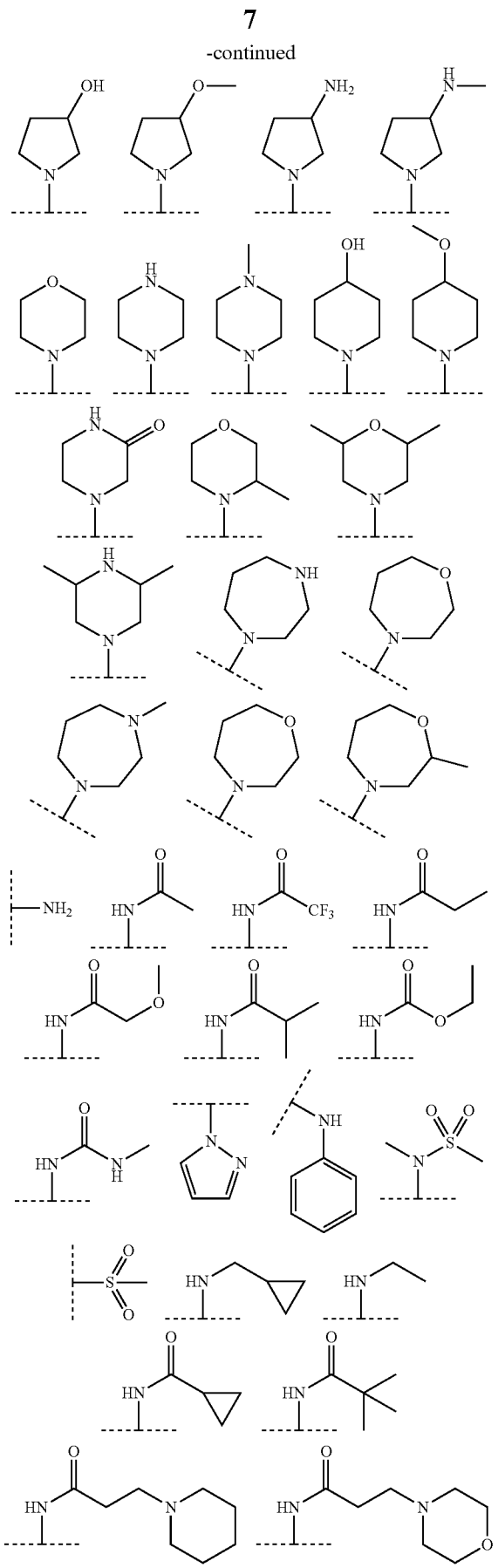

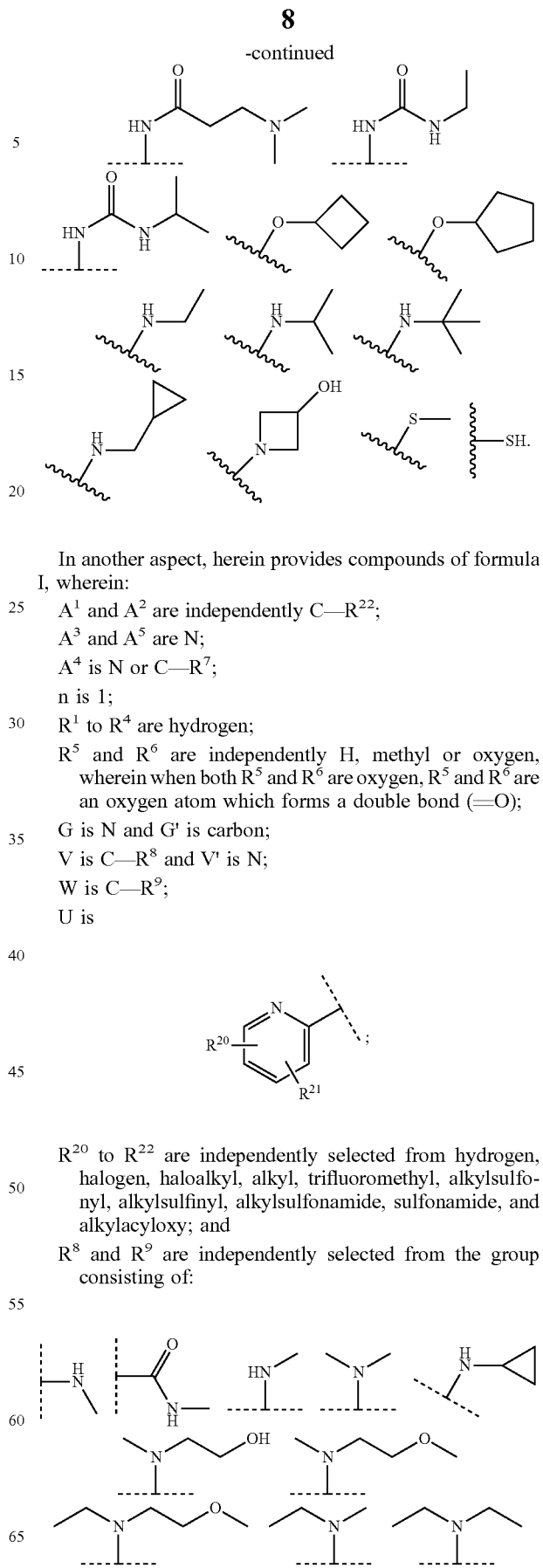

In another aspect, herein provides compounds of formula I, wherein:

$A^1$ and $A^2$ are independently $C-R^{22}$;
$A^3$ and $A^5$ are N;
$A^4$ is N or $C-R^7$;
n is 1;
$R^1$ to $R^4$ are hydrogen;
$R^5$ and $R^6$ are independently H, methyl or oxygen, wherein when both $R^5$ and $R^6$ are oxygen, $R^5$ and $R^6$ are an oxygen atom which forms a double bond (=O);
G is N and G' is carbon;
V is $C-R^8$ and V' is N;
W is $C-R^9$;
U is

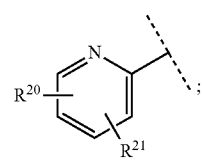

$R^{20}$ to $R^{22}$ are independently selected from hydrogen, halogen, haloalkyl, alkyl, trifluoromethyl, alkylsulfonyl, alkylsulfinyl, alkylsulfonamide, sulfonamide, and alkylacyloxy; and
$R^8$ and $R^9$ are independently selected from the group consisting of:

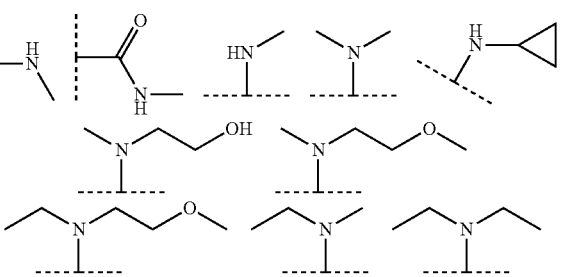

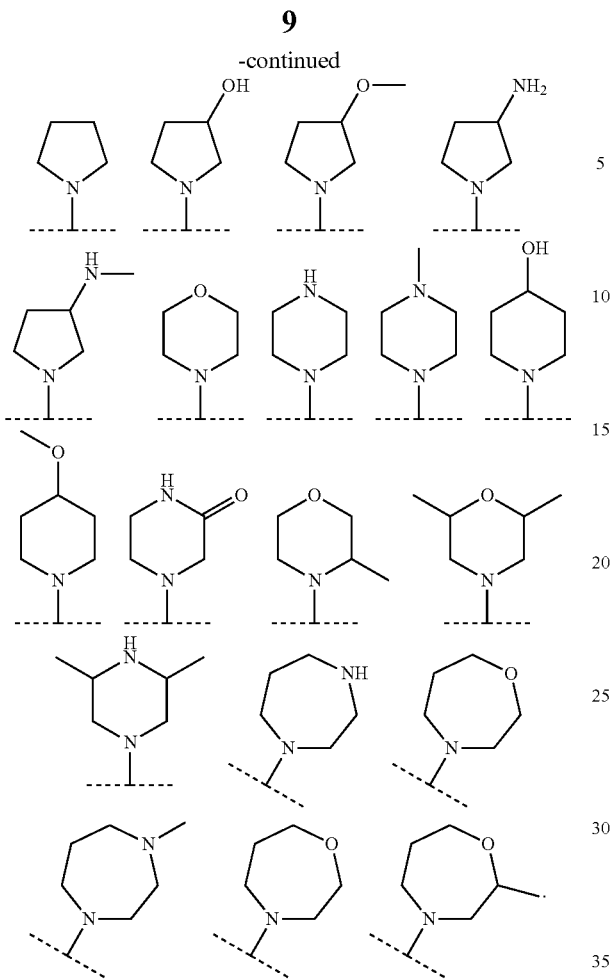
In another aspect, herein provides compounds of the following structures:
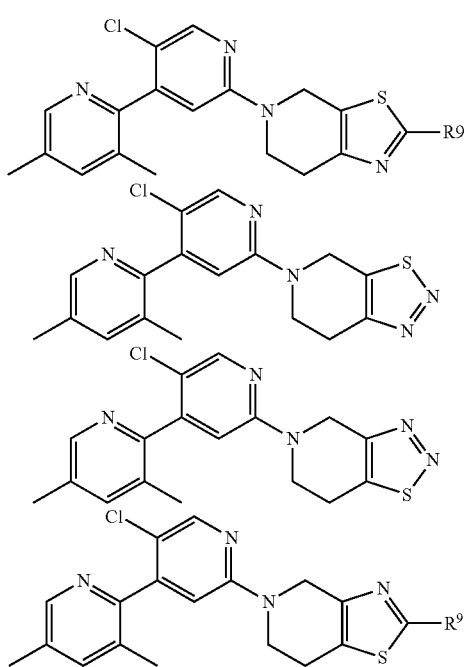
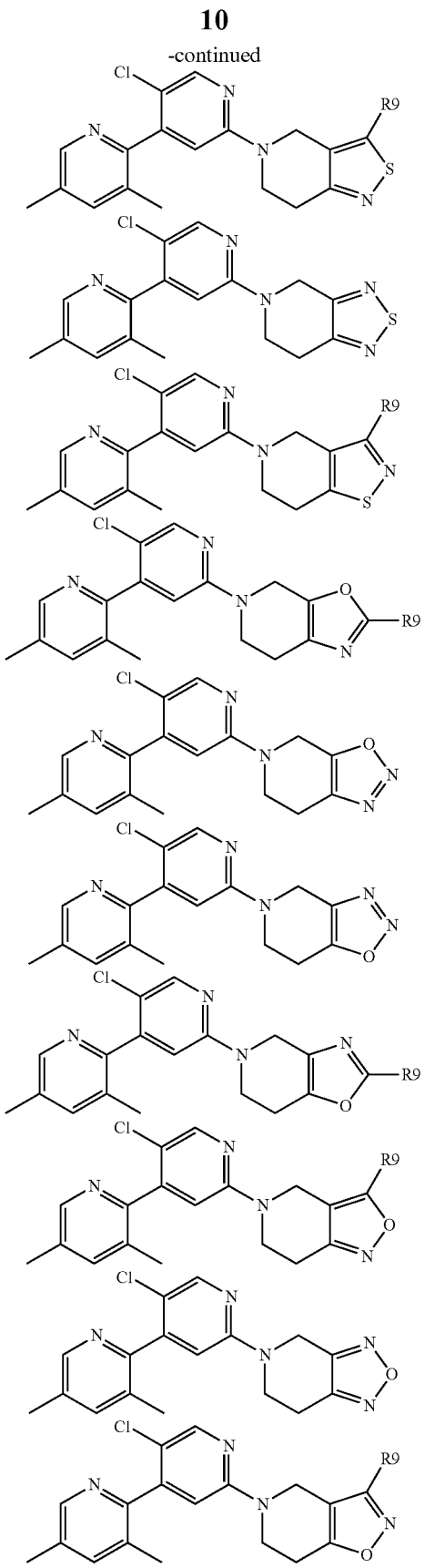
or pharmaceutically acceptable salts, or solvates thereof, wherein $R^9$ are independently selected from the group consisting of hydrogen, halogen, haloalkyl, alkyl, CN, cyanoalkyl, alkoxy, alkenyl, alkynyl, amino, hydroxyl, acyloxy, acylamino, urea, carbamoyloxy, thiourea, sulfone, sulfoxide, sulfonamide, azido, alkylalkenyl, alkylalkynyl, alkylamino, alkylacyloxy, alkylsulfonyl, alkylsulfinyl, alkylsulfonamide, azidoalkyl, cycloalkyl, cycloalkenyl, 3-12 membered heterocycle, aryl, 5-12 membered heteroaryl; and

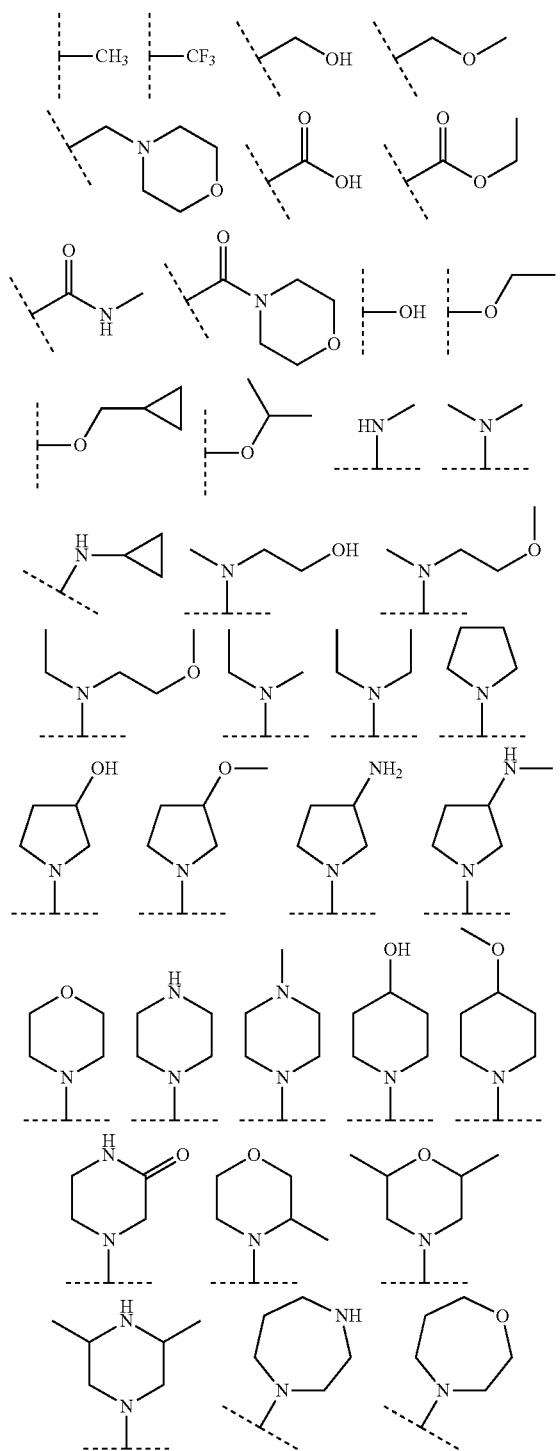
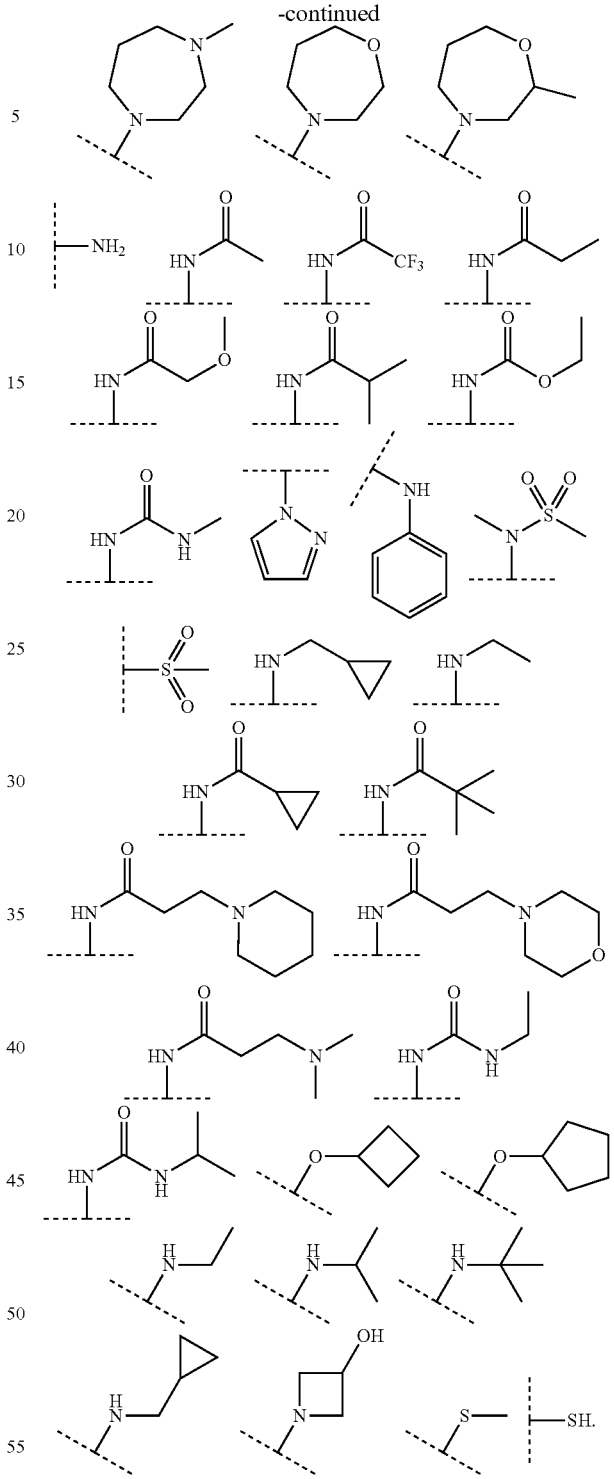

In another aspect, the present invention provides a pharmaceutical composition comprising a compound of formula I and a pharmaceutically acceptable carrier.

In still another aspect, A method for inhibiting activation of a hedgehog-patched pathway in a patient diagnosed with a hyper-proliferative disorder, comprising administering to the patient a composition comprising a hedgehog pathway inhibitor in an effective amount to reduce the activation of the hedgehog-patched pathway in a cell of the patient, wherein the hedgehog pathway inhibitor is a compound of formula I described above ([0009]).

Figure 1:
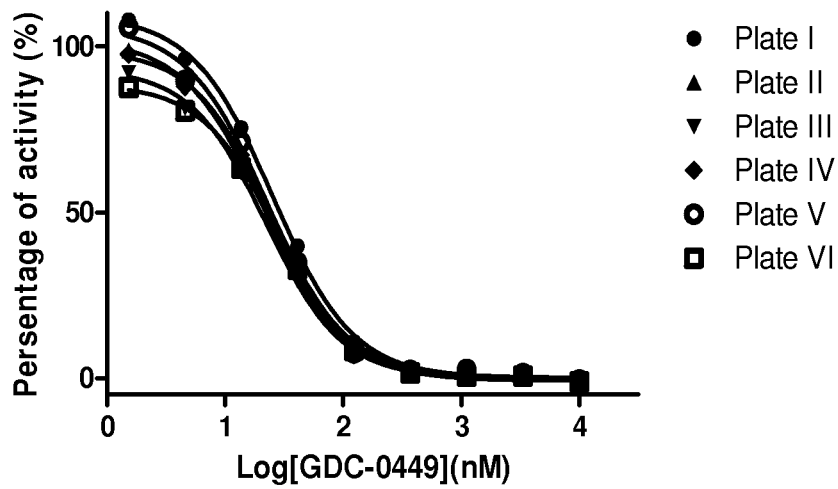
FIG. 1 depicts the IC50 curves of the standard compound A in the primary assay.

Before proceeding with the detailed description, it is to be appreciated that the following detailed description is merely exemplary in nature and is not intended to limit the invention or the application and uses thereof. Hence, although the present disclosure is, for convenience of explanation, depicted and described as shown in certain illustrative embodiments, it will be appreciated that it can be implemented in various other types of embodiments and equivalents, and in various other systems and environments. Furthermore, there is no intention to be bound by any theory presented in the preceding background or the following detailed description.

DETAILED DESCRIPTION OF THE INVENTION

Definitions

Compounds are generally described herein using standard nomenclature. For compounds having asymmetric centers, it should be understood that (unless otherwise specified) all of the optical isomers and mixtures thereof are encompassed. In addition, compounds with carbon-carbon double bonds may occur in Z- and E-forms, with all isomeric forms of the compounds being included in the present invention unless otherwise specified. Where a compound exists in various tautomeric forms, a recited compound is not limited to any one specific tautomer, but rather is intended to encompass all tautomeric forms.

As used herein, the term "alkyl" refers to a straight or branched chain saturated aliphatic hydrocarbon. Alkyl groups include groups having from 1 to 8 carbon atoms ($C_{1-8}$ alkyl), from 1 to 6 carbon atoms ($C_{1-6}$ alkyl) and from 1 to 4 carbon atoms ($C_{14}$ alkyl), including, for example, methyl, ethyl, propyl, isopropyl, n-butyl, sec-butyl, tert-butyl, pentyl, 2-pentyl, isopentyl, neopentyl, hexyl, 2-hexyl, 3-hexyl and 3-methylpentyl. In some instances, a substituent of an alkyl group is specifically indicated. For example, "cyanoalkyl" refers to an alkyl group substituted with at least one cyano substituent.

"Alkenyl" refers to straight or branched chain alkene groups, which comprise at least one unsaturated carbon-carbon double bond. Alkenyl groups include $C_{2-8}$ alkenyl, $C_{2-6}$ alkenyl and $C_{24}$ alkenyl groups, which have from 2 to 8, 2 to 6 or 2 to 4 carbon atoms, respectively, including, for example, ethenyl, allyl or isopropenyl. "Alkynyl" refers to straight or branched chain alkyne groups, which have one or more unsaturated carbon-carbon bonds, at least one of which is a triple bond. Alkynyl groups include $C_{2-8}$ alkynyl, $C_{2-6}$ alkynyl and $C_{24}$ alkynyl groups, which have from 2 to 8, 2 to 6 or 2 to 4 carbon atoms, respectively.

A "cycloalkyl" is a group that comprises one or more saturated rings in which all ring members are carbon, including, for example, cyclopropyl, cyclobutyl, cyclopentyl, cyclohexyl, cycloheptyl, cyclooctyl, adamantyl. Cycloalkyl groups do not comprise an aromatic ring or a heterocyclic ring. Certain cycloalkyl groups are $C_{3-7}$ cycloalkyl, in which the cycloalkyl group contains a single ring having from 3 to 7 ring members, all of which are carbon. A "cycloalkenyl" is a group that comprises one or more unsaturated rings in which all ring members are carbon.

"Alkoxy" is meant an alkyl group as described above attached via an oxygen bridge. Alkoxy groups include $C_{1-6}$ alkoxy and $C_{14}$ groups, which have from 1 to 6 or from 1 to 4 carbon atoms, respectively. Methoxy, ethoxy, propoxy, isopropoxy, n-butoxy, sec-butoxy, tert-butoxy, n-pentoxy, 2-pentoxy, 3-pentoxy, isopentoxy, neopentoxy, hexoxy, 2-hexoxy, 3-hexoxy, and 3-methylpentoxy are representative alkoxy groups.

"Alkylamino" refers to a secondary or tertiary amine that has the general structure —NH-alkyl or —N(alkyl)(alkyl), wherein each alkyl is selected independently from alkyl, cycloalkyl and (cycloalkyl)alkyl groups. Such groups include, for example, mono- and di-($C_{1-6}$ alkyl)amino groups, in which each $C_{1-6}$ alkyl may be the same or different. It will be apparent that the definition of "alkyl" as used in the term "alkylamino" differs from the definition of "alkyl" used for all other alkyl-containing groups, in the inclusion of cycloalkyl and (cycloalkyl)alkyl groups.

"Halogen" means fluorine, chlorine, bromine, and iodine. A "haloalkyl" is an alkyl group that is substituted with 1 or more independently chosen halogens (e.g., "$C_{1-6}$ haloalkyl" groups have from 1 to 6 carbon atoms and at least one halogen). Examples of haloalkyl groups include, but are not limited to, mono-, di- or tri-fluoromethyl; mono-, di- or tri-chloromethyl; mono-, di-, tri-, tetra- or penta-fluoroethyl; mono-, di-, tri-, tetra- or penta-chloroethyl; and 1,2,2,2-tetrafluoro-1-trifluoromethyl-ethyl.

A "heteroaryl" is an aromatic group in which at least one aromatic ring comprises at least one heteroatom selected from N, O and S. Heteroaryls include, for example, 5-12 membered heteroaryls. Examples included but are not limited to imidazole, furan, furazan, isothiazole, isoxazole, oxadiazole, oxazole, pyrazine, pyrazole, pyridazine, pyridine, pyrimidine, tetrazole, thiazole and thiophene.

The term "heterocyclic" refers to a ring structure containing 3-12 ring atoms, in which at least one ring atom is carbon and at least one ring atom is heteroatom selected from N, O, and S. A heterocyclic group may be aromatic or non-aromatic. Piperidine and oxetane are non-limiting examples of non-aromatic heterocycles. Thiazole and pyridine are non-limiting examples of aromatic heterocycles.

A "substituent" and "substituted," as used herein, denote that a molecular moiety is covalently bonded to an atom within a molecule of interest. For example, a ring substituent may be a moiety such as a halogen, alkyl group, haloalkyl group or other group that is covalently bonded to an atom (preferably a carbon or nitrogen atom) that is a ring member. Substituents of aromatic groups are generally covalently bonded to a ring carbon atom.

The term "pharmaceutically acceptable" when used with reference to a compound of formula I is intended to refer to a form of the compound that is safe for administration to a subject. For example, a free base, a salt form, a solvate, a hydrate, a prodrug or derivative form of a compound of formula I, which has been approved for mammalian use, via oral ingestion or any other route of administration, by a governing authority or regulatory agency, such as the Food and Drug Administration (FDA) of the United States, is pharmaceutically acceptable.

Included in the compounds of formula I are the pharmaceutically acceptable salt forms of the free-base compounds. The term "pharmaceutically-acceptable salts" embraces salts, commonly used to form alkali metal salts and to form addition salts of free acids or free bases, which have been approved by a regulatory agency. Salts are formed from ionic associations, charge-charge interactions, covalent bonding, complexation, coordination, etc. The nature of the salt is not critical, provided that it is pharmaceutically acceptable.

In some embodiments, the compound(s) of formula I is used to treat a subject by administering the compound(s) as a pharmaceutical composition. To this end, the compound(s), in one embodiment, is combined with one or more pharmaceutically acceptable excipients, including carriers, diluents or adjuvants, to form a suitable composition, which is described in more detail herein.

The term "excipient", as used herein, denotes any pharmaceutically acceptable additive, carrier, adjuvant, or other suitable ingredient, other than the active pharmaceutical ingredient (API), which is typically included for formulation and/or administration purposes. "Diluent" and "adjuvant" are defined hereinafter.

The terms "treat", "treating," "treatment," and "therapy" as used herein refer to therapy, including without limitation, curative therapy, prophylactic therapy, and preventative therapy. Prophylactic treatment generally constitutes either preventing the onset of disorders altogether or delaying the onset of a pre-clinically evident stage of disorders in individuals.

The phrase "effective amount" is intended to quantify the amount of each agent, which will achieve the goal of improvement in disorder severity and the frequency of incidence over treatment of each agent by itself, while avoiding adverse side effects typically associated with alternative therapies. The effective amount, in one embodiment, is administered in a single dosage form or in multiple dosage forms.

Regardless of the route of administration selected, the compounds of the present invention, which may be used in a suitable hydrated form, and/or the pharmaceutical compositions of the present invention, are formulated into pharmaceutically acceptable dosage forms or by other conventional methods known to those of skill in the art.

Actual dosage levels of the active ingredients in the pharmaceutical compositions of the present invention may be varied so as to obtain an effective amount of the active ingredient to achieve the desired therapeutic response for a particular patient, composition, and mode of administration, without being toxic to the patient.

The selected dosage level will depend upon a variety of factors including the activity of the particular compound of the present invention employed, the route of administration, the time of administration, the rate of excretion of the particular compound being employed, the duration of the treatment, other drugs, compounds and/or materials used in combination with the particular hedgehog inhibitor employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient will range from about 0.0001 to about 100 mg per kilogram of body weight per day. The mode of administration can have a large effect on dosage. Higher doses may be used for localized routes of delivery.

If desired, the effective daily dose of the active compound may be administered as two, three, four, five, six or more sub-doses administered separately at appropriate intervals throughout the day, optionally, in unit dosage forms. Those of skill in the art will readily appreciate that dose levels can vary as a function of the specific compound, the severity of the symptoms and the susceptibility of the subject to side effects. Dosages for a given compound disclosed herein are readily determinable by those of skill in the art by a variety of means.

Pharmaceutical Compositions/Formulations

One embodiment provides a pharmaceutical composition comprising a compound of formula I, or a stereoisomer, tautomer, hydrate, solvate or pharmaceutically acceptable salt thereof, and at least one pharmaceutically acceptable excipient.

In some embodiments, the present invention provides methods for regulating the hedgehog pathway. The method comprises administrating to a mammalian subject a therapeutically effective amount of at least one compound of formula I. The method comprises treating or preventing liver carcinoma, lung carcinoma, cervical carcinoma, pancreas carcinoma, breast carcinoma, stomach carcinoma, oral carcinoma, esophageal carcinoma, nasopharyngeal carcinoma, dermal carcinoma, osteocarcinoma, kidney cancer, and leukemia.

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that can be used pharmaceutically. Proper formulation is dependent upon the route of administration chosen. A summary of pharmaceutical compositions described herein can be found, for example, in *Remington: The Science and Practice of Pharmacy*, Nineteenth Ed., Easton, Pa.: Mack Publishing Company (1995); Hoover, John E., *Remington's Pharmaceutical Sciences*, Mack Publishing Co., Easton, Pa. (1975); Liberman, H. A. and Lachman, L., Eds., *Pharmaceutical Dosage Forms*, Marcel Decker, New York, N.Y. (1980); and *Pharmaceutical Dosage Forms and Drug Delivery Systems*, Seventh Ed., Lippincott Williams & Wilkins (1999), herein incorporated by reference for such disclosure.

A pharmaceutical composition, as used herein, refers to a mixture of a compound of formula I with other chemical components (i.e. pharmaceutically acceptable inactive ingredients), such as carriers, excipients, binders, filling agents, suspending agents, flavoring agents, sweetening agents, disintegrating agents, dispersing agents, surfactants, lubricants, colorants, diluents, solubilizers, moistening agents, plasticizers, stabilizers, penetration enhancers, wetting agents, anti-foaming agents, antioxidants, preservatives, or one or more combination thereof. The pharmaceutical composition facilitates administration of the compound to an organism. In practicing the methods of treatment or use provided herein, therapeutically effective amounts of compounds described herein are administered in a pharmaceutical composition to a mammal having a disease, disorder, or condition to be treated. In some embodiments, the mammal is a human. A therapeutically effective amount can vary widely depending on the severity of the disease, the age and relative health of the subject, the potency of the compound used and other factors. The compounds can be used singly or in combination with one or more therapeutic agents as components of mixtures.

The pharmaceutical formulations described herein are administered to a subject by appropriate administration routes, including but not limited to, oral, parenteral (e.g., intravenous, subcutaneous, intramuscular), intranasal, buccal, topical, rectal, or transdermal administration routes. The pharmaceutical formulations described herein include, but are not limited to, aqueous liquid dispersions, self-emulsifying dispersions, solid solutions, liposomal dispersions, aerosols, solid dosage forms, powders, immediate release formulations, controlled release formulations, fast melt formulations, tablets, capsules, pills, delayed release formulations, extended release formulations, pulsatile release formulations, multiparticulate formulations, and mixed immediate and controlled release formulations.

All formulations for oral administration are in dosages suitable for such administration. Examples of such dosage units are tablets or capsules. In some embodiments, these contain an amount of active ingredient from about 1 to 2000 mg, advantageously from about 1 to 500 mg, and typically from about 5 to 150 mg. A suitable daily dose for a human or other mammal vary widely depending on the condition of the patient and other factors, but, once again, can be determined using routine methods and practices.

Conventional formulation techniques include, e.g., one or a combination of methods: (1) dry mixing, (2) direct compression, (3) milling, (4) dry or non-aqueous granulation, (5) wet granulation, or (6) fusion. Other methods include, e.g., spray drying, pan coating, melt granulation, granulation, fluidized bed spray drying or coating (e.g., wurster coating), tangential coating, top spraying, tableting, extruding and the like.

Suitable carriers for use in the solid dosage forms described herein include, but are not limited to, acacia, gelatin, colloidal silicon dioxide, calcium glycerophosphate, calcium lactate, maltodextrin, glycerine, magnesium silicate, sodium caseinate, soy lecithin, sodium chloride, tricalcium phosphate, dipotassium phosphate, sodium stearoyl lactylate, carrageenan, monoglyceride, diglyceride, pregelatinized starch, hydroxypropyl-methylcellulose, hydroxypropylmethylcellulose acetate stearate, sucrose, microcrystalline cellulose, lactose, mannitol and the like.

Suitable filling agents for use in the solid dosage forms described herein include, but are not limited to, lactose, calcium carbonate, calcium phosphate, dibasic calcium phosphate, calcium sulfate, microcrystalline cellulose, cellulose powder, dextrose, dextrates, dextran, starches, pregelatinized starch, hydroxypropylmethylcellulose (HPMC), hydroxypropyl-methylcellulose phthalate, hydroxypropylmethylcellulose acetate stearate (HPMCAS), sucrose, xylitol, lactitol, mannitol, sorbitol, sodium chloride, polyethylene glycol, and the like.

Suitable disintegrants for use in the solid dosage forms described herein include, but are not limited to, natural starch such as corn starch or potato starch, a pregelatinized starch, or sodium starch glycolate, a cellulose such as methylcrystalline cellulose, methylcellulose, microcrystalline cellulose, croscarmellose, or a cross-linked cellulose, such as cross-linked sodium carboxymethylcellulose, cross-linked carboxymethylcellulose, or cross-linked croscarmellose, a cross-linked starch such as sodium starch glycolate, a cross-linked polymer such as crospovidone, a cross-linked polyvinylpyrrolidone, alginate such as alginic acid or a salt of alginic acid such as sodium alginate, a gum such as agar, guar, locust bean, Karaya, pectin, or tragacanth, sodium starch glycolate, bentonite, sodium lauryl sulfate, sodium lauryl sulfate in combination starch, and the like.

Binders impart cohesiveness to solid oral dosage form formulations: for powder filled capsule formulation, they aid in plug formation that can be filled into soft or hard shell capsules and for tablet formulation, they ensure the tablet remaining intact after compression and help assure blend uniformity prior to a compression or fill step. Materials suitable for use as binders in the solid dosage forms described herein include, but are not limited to, carboxymethylcellulose, methylcellulose, hydroxypropylmethylcellulose, hydroxypropylmethylcellulose acetate stearate, hydroxyethylcellulose, hydroxypropylcellulose, ethylcellulose, and microcrystalline cellulose, microcrystalline dextrose, amylose, magnesium aluminum silicate, polysaccharide acids, bentonites, gelatin, polyvinylpyrrolidone/vinyl acetate copolymer, crospovidone, povidone, starch, pregelatinized starch, tragacanth, dextrin, a sugar, such as sucrose, glucose, dextrose, molasses, mannitol, sorbitol, xylitol, lactose, a natural or synthetic gum such as acacia, tragacanth, ghatti gum, mucilage of isapol husks, starch, polyvinylpyrrolidone, larch arabogalactan, polyethylene glycol, waxes, sodium alginate, and the like.

In general, binder levels of 20-70% are used in powderfilled gelatin capsule formulations. Binder usage level in tablet formulations varies whether direct compression, wet granulation, roller compaction, or usage of other excipients such as fillers which itself can act as moderate binder. Binder levels of up to 70% in tablet formulations are common.

Suitable lubricants or glidants for use in the solid dosage forms described herein include, but are not limited to, stearic acid, calcium hydroxide, talc, corn starch, sodium stearyl fumarate, alkali-metal and alkaline earth metal salts, such as aluminum, calcium, magnesium, zinc, stearic acid, sodium stearates, magnesium stearate, zinc stearate, waxes, Stearowet®, boric acid, sodium benzoate, sodium acetate, sodium chloride, leucine, a polyethylene glycol or a methoxypolyethylene glycol such as Carbowax™, PEG 4000, PEG 5000, PEG 6000, propylene glycol, sodium oleate, glyceryl behenate, glyceryl palmitostearate, glyceryl benzoate, magnesium or sodium lauryl sulfate, and the like.

Suitable diluents for use in the solid dosage forms described herein include, but are not limited to, sugars (including lactose, sucrose, and dextrose), polysaccharides (including dextrates and maltodextrin), polyols (including mannitol, xylitol, and sorbitol), cyclodextrins and the like.

Suitable wetting agents for use in the solid dosage forms described herein include, for example, oleic acid, glyceryl monostearate, sorbitan monooleate, sorbitan monolaurate, triethanolamine oleate, polyoxyethylene sorbitan monooleate, polyoxyethylene sorbitan monolaurate, quaternary ammonium compounds (e.g., Polyquat 10®), sodium oleate, sodium lauryl sulfate, magnesium stearate, sodium docusate, triacetin, vitamin E TPGS and the like.

Suitable surfactants for use in the solid dosage forms described herein include, for example, sodium lauryl sulfate, sorbitan monooleate, polyoxyethylene sorbitan monooleate, polysorbates, polaxomers, bile salts, glyceryl monostearate, copolymers of ethylene oxide and propylene oxide, e.g., Pluronic® (BASF), and the like.

Suitable suspending agents for use in the solid dosage forms described here include, but are not limited to, polyvinylpyrrolidone, e.g., polyvinylpyrrolidone K12, polyvinylpyrrolidone K17, polyvinylpyrrolidone K25, or polyvinylpyrrolidone K30, polyethylene glycol, e.g., the polyethylene glycol can have a molecular weight of about 300 to about 6000, or about 3350 to about 4000, or about 7000 to about 5400, vinyl pyrrolidone/vinyl acetate copolymer (S630), sodium carboxymethylcellulose, methylcellulose, hydroxypropyl-methylcellulose, polysorbate-80, hydroxyethylcellulose, sodium alginate, gums, such as, e.g., gum tragacanth and gum acacia, guar gum, xanthans, including xanthan gum, sugars, cellulosics, such as, e.g., sodium carboxymethylcellulose, methylcellulose, sodium carboxymethylcellulose, hydroxypropylmethylcellulose, hydroxyethylcellulose, polysorbate-80, sodium alginate, polyethoxylated sorbitan monolaurate, polyethoxylated sorbitan monolaurate, povidone and the like.

Methods of the present invention include the use of at least one compound of formula I, which inhibits hedgehog signaling in the regulation of repair and/or functional performance of a wide range of cells, tissues and organs, and have therapeutic and cosmetic applications ranging from regulation of neural tissues, bone and cartilage formation and repair, regulation of spermatogenesis, regulation of smooth muscle, regulation of lung, liver and other organs arising from the primitive gut, regulation of hematopoietic function, regulation of skin and hair growth, etc. Accordingly, the methods and compositions of the present invention include the use of the subject inhibitors for all such uses as inhibitors of hedgehog proteins may be implicated. Moreover, the subject methods can be performed on cells which are provided in culture (in vitro), or on cells in a whole animal (in vivo).

The examples and preparations provided below illustrated and exemplify the compounds described herein and methods of preparing such compounds. In general, the compounds described herein may be prepared by processes known in the general chemical arts.

The compounds of the present invention can be prepared using various synthetic routes, including those described by METHEODS A-R below, starting from commercially available materials. Starting materials of the invention, are either known, commercially available, or can be synthesized in analogy to or according to methods that are known in the art. Many starting materials may be prepared according to known processes and, in particular, can be prepared using processes described in the examples. In synthesizing starting materials, functional groups in some cases are protected with suitable protecting groups when necessary. Functional groups may be removed according to known procedures in the art.

Methods A, B, C:

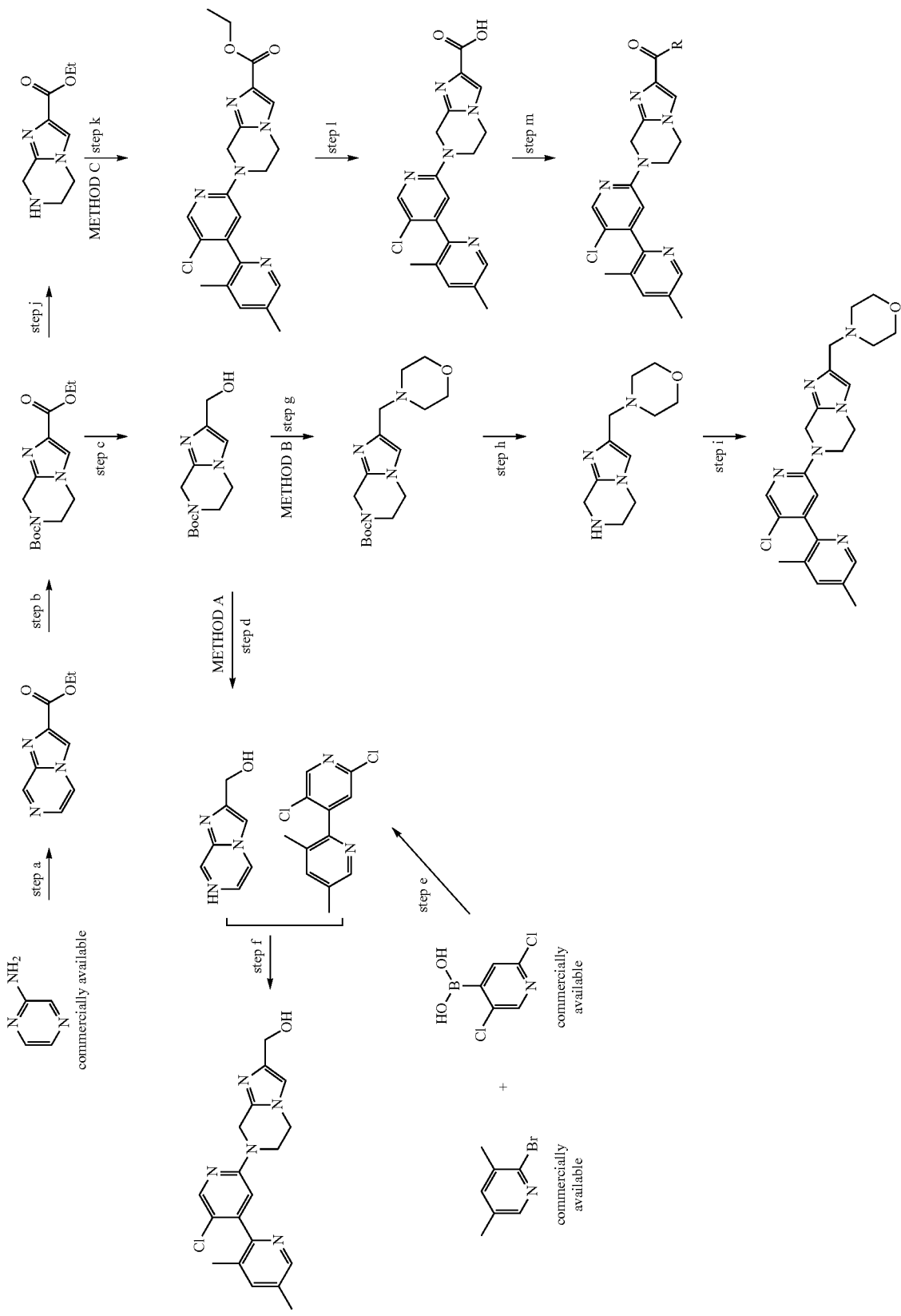

23                                                                                                                                      24
Methods D, E:
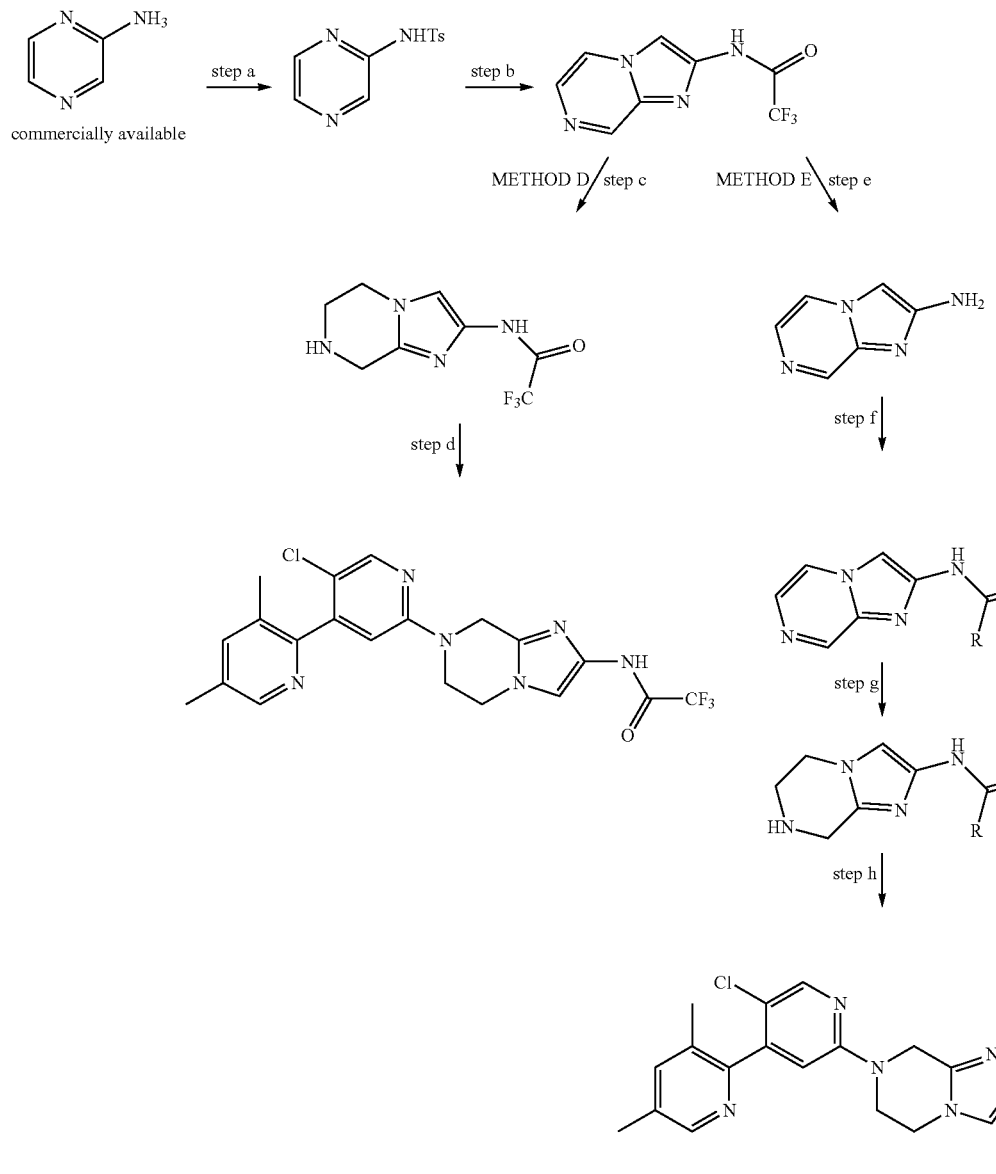
Methods F, G:
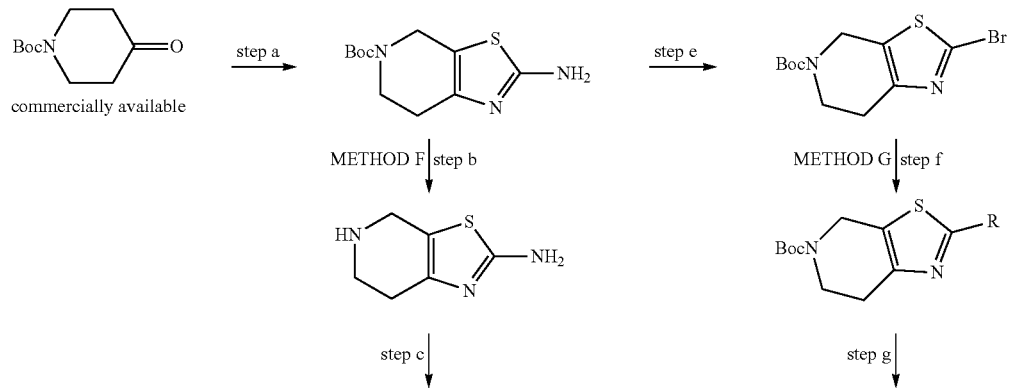

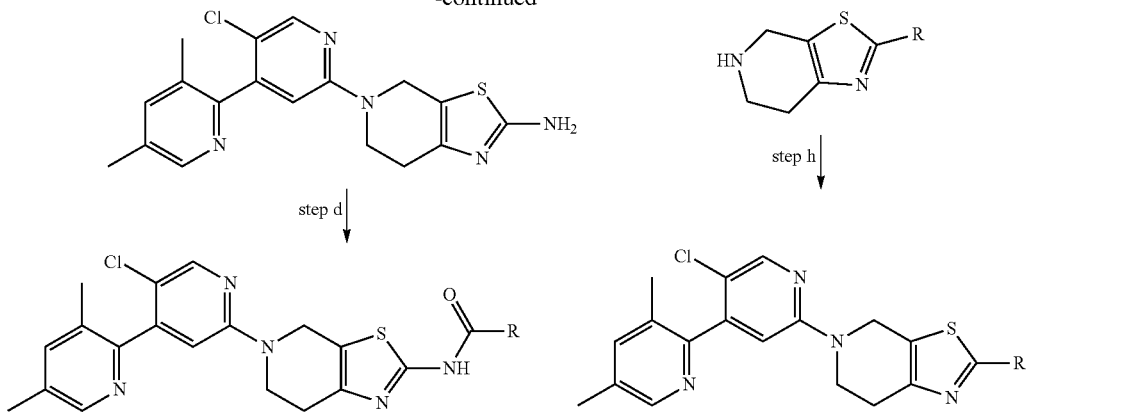
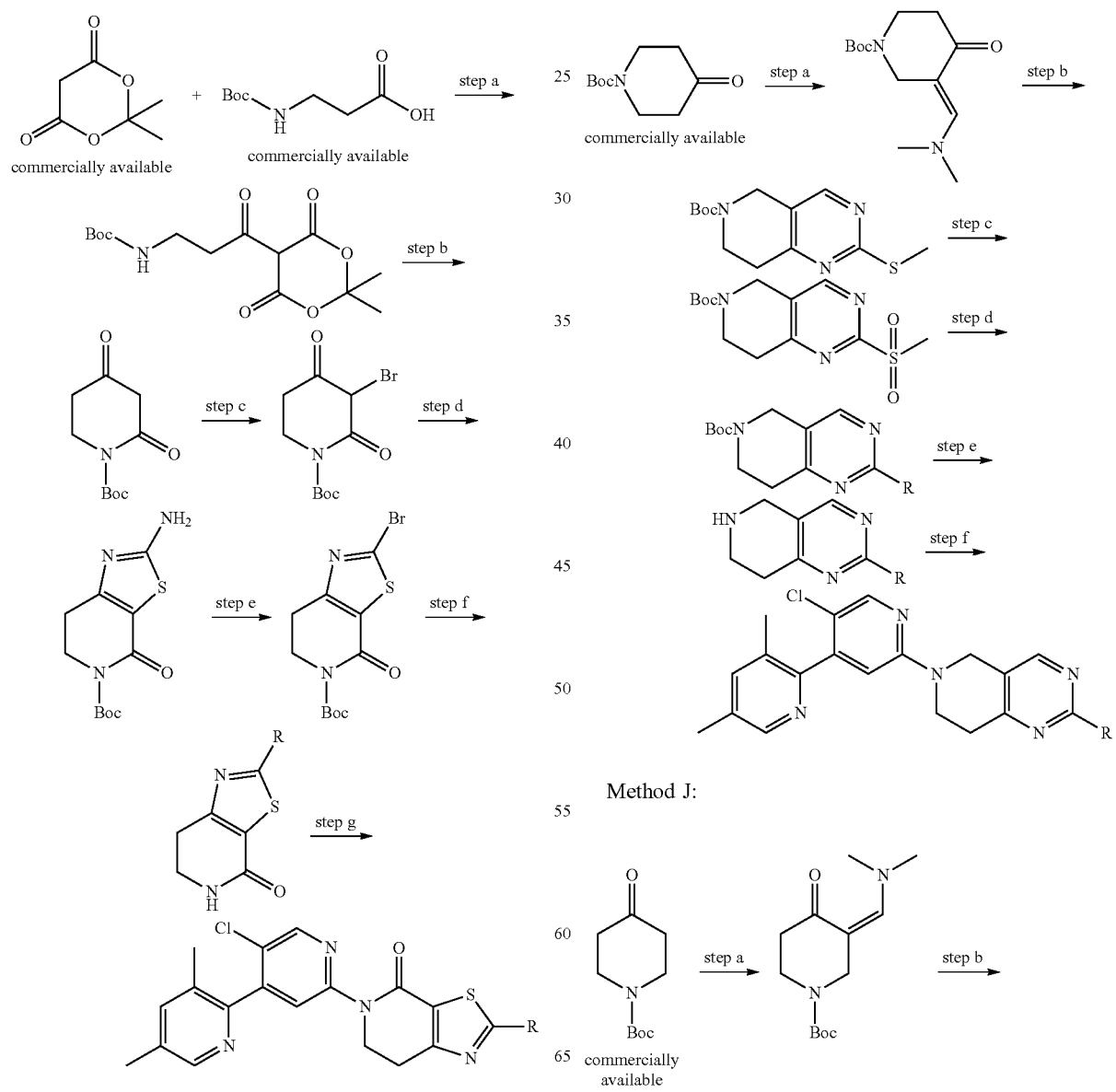

27
-continued
28
-continued
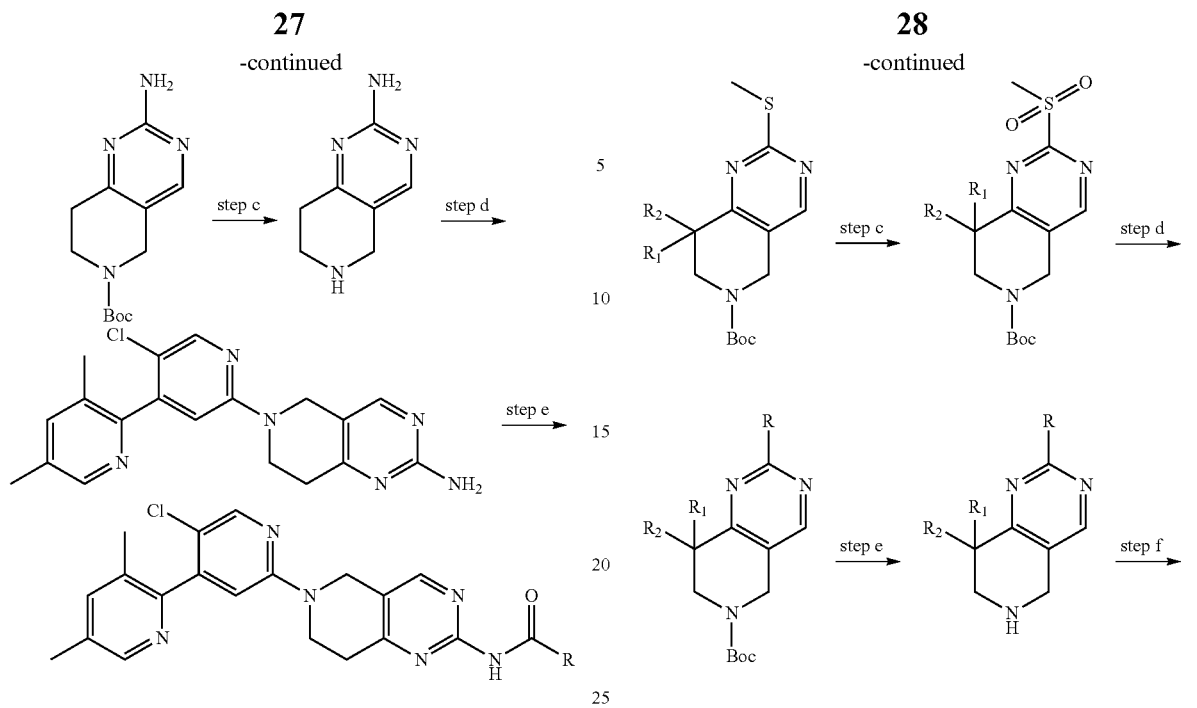
Method K:
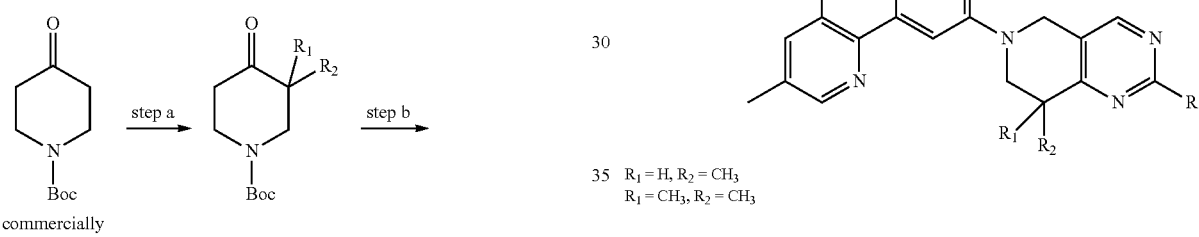
$R_1 = H, R_2 = CH_3$
$R_1 = CH_3, R_2 = CH_3$
Methods L, M, N:
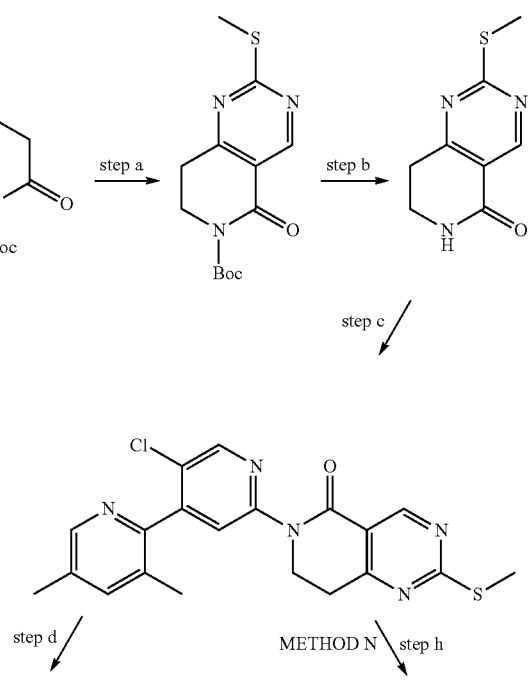

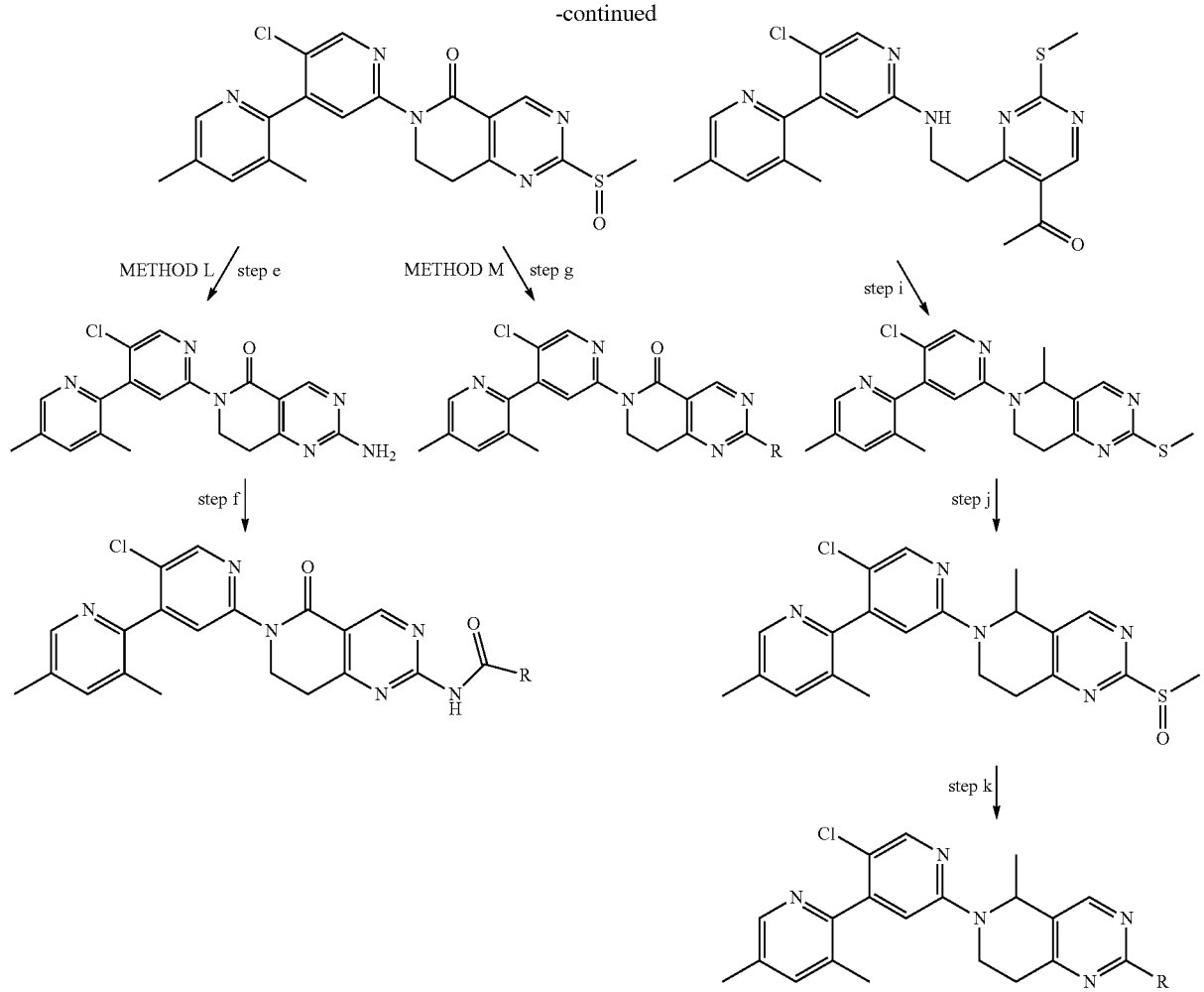
Method O:
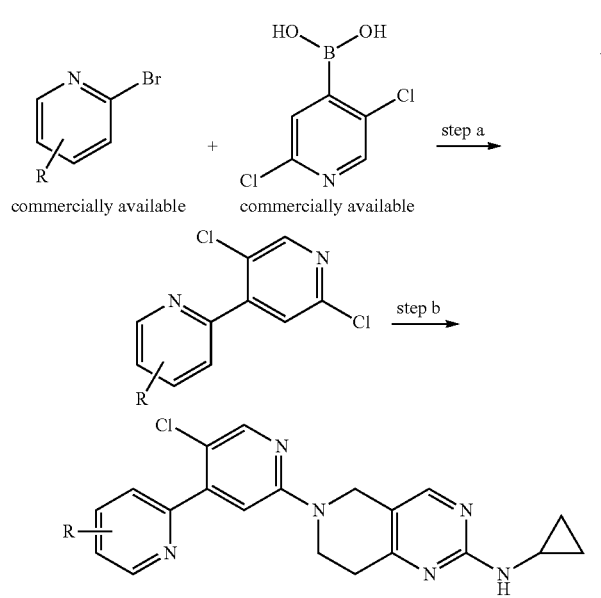
Method P:
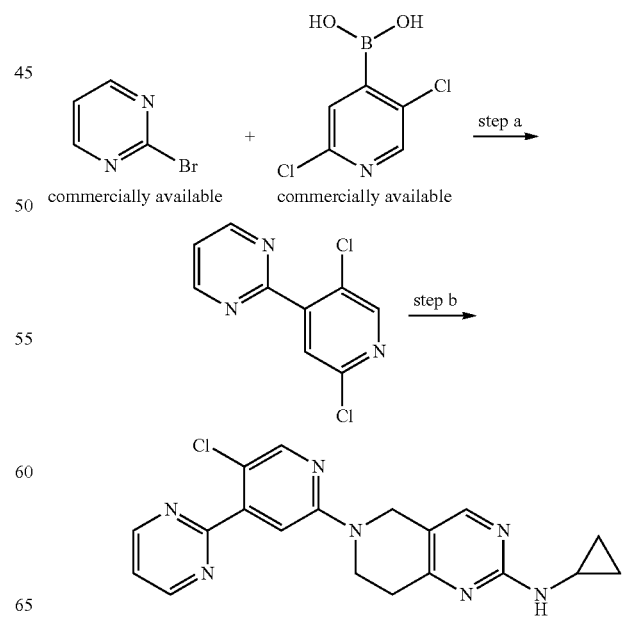

Method Q:

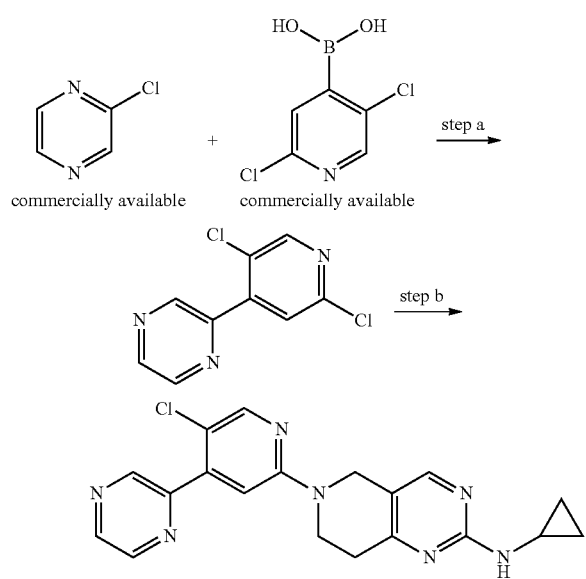

Method R:

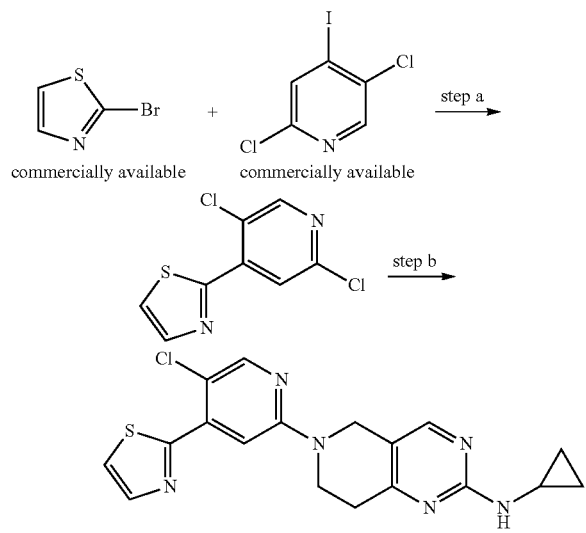

Materials and Methods

All reagents and solvents were obtained commercially. When required, all reagents and solvents were purified by standard techniques: tetrahydrofuran was purified by distillation from sodium. All thin-layer chromatography (TLC) analyses were performed on silica gel (Qingdao Haiyang Chemical Co. Ltd.) and spots revealed by UV visualization at 254 nm and $I_2$ vapor or phosphomolybdic acid. All nuclear magnetic resonance spectra were recorded using a Varian unity INOVA 400NB spectrometer at 400 MHz or a Varian Vnmrs spectrometer at 300 MHz as indicated. LC-MS was run using an Agilent 1100 system using an Agela Durashell C18 3.5 μm 4.6×50 mm column. Gradients were run using 0.1 trifluoroacetic acid/water and acetonitrile with gradient 5/95 to 95/5 in the run time indicated.

SYNTHESIS

Example 1

Preparation of (7-(5'-chloro-3,5-dimethyl-2,4'-bi-pyridin-2'-yl)-5,6,7,8-tetrahydroimidaz[1,2-a]pyrazin-2-yl)methanol (A-10)

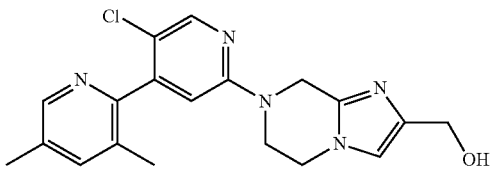 [SMILES: Cc1cnc(-c2cc(N3CCn4cc(CO)nc4C3)ncc2Cl)c(C)c1]

Method A—Step a: Preparation of Ethyl imidazo[1,2-a]pyrazine-2-carboxylate

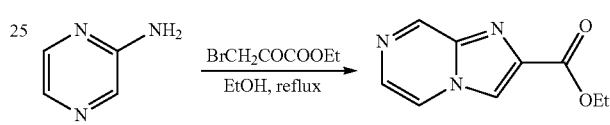

To a stirred solution of 2-aminopyrazine (1.0 g, 10.5 mmol) in dimethoxyethane, ethyl bromopyruvate (2.36 g, 13.0 mmol) was added at room temperature and stirred for 2.5 hours. The reaction mixture was cooled to 0° C. and stirred for 30 min to afford a pale brown precipitate. The precipitate was filtered and washed with ethyl acetate to give a pale brown solid. The precipitate was suspended in 50 mL ethyl alcohol and heated at reflux temperature to turn to a clear solution. After refluxing for 2 hours, the reaction mixture was concentrated under reduced pressure and then mixed with $CH_2Cl_2$ and saturated aqueous $NaHCO_3$ solution. The mixture was filtered through a pad of Celite, and the separated organic layer was dried by $Na_2SO_4$ and filtered. The residue was applied to silica gel column chromatography, and the column was eluted with ($CH_2Cl_2$:MeOH=99:1 to 97:3), and the collected fractions were concentrated under reduced pressure. The title compound was obtained as pale yellow crystals (0.546 g, 27%). $^1$H NMR (400 MHz, $CDCl_3$) δ 9.21 (s, 1H), 8.26 (s, 1H), 8.09 (dd, J=4.7, 1.6 Hz, 1H), 7.96 (d, J=4.7 Hz, 1H), 4.49 (q, J=7.1 Hz, 2H), 1.45 (t, J=7.1 Hz, 3H).

Method A—Step b: Preparation of 7-tert-butyl-2-ethyl-5,6-dihydroimidazo[1,2-a]pyrazine-2,7(8H)-dicarboxylate

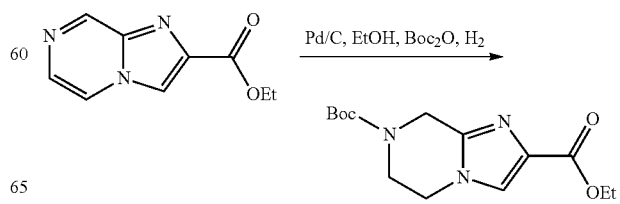

To a solution of ethyl imidazo[1,2-a]pyrazine-2-carboxylate (1 g, 5.2 mmol) in 500 mL ethyl alcohol was added Boc$_2$O (3.0 g, 18 mmol) and 200 mg 10% Pd—C (50% wet) under hydrogen atmosphere, then the mixture was stirred at room temperature for 24 hours. The reaction mixture was filtered, the filtrate was concentrated under reduced pressure. The residue was applied to silica gel column chromatography and eluted with (CH$_2$Cl$_2$:MeOH=50:1). The title compound was obtained as a yellow oil (0.973 g, 63%). $^1$H NMR (400 MHz, CDCl$_3$) δ 7.51 (s, 1H), 4.68 (s, 2H), 4.30 (q, J=7.1 Hz, 2H), 4.00 (t, J=5.2 Hz, 2H), 3.82 (t, J=5.2 Hz, 2H), 1.43 (s, 9H), 1.21 (t, J=7.1 Hz, 3H).

Method A—Step c: Preparation of tert-butyl 2-(hydroxymethyl)-5,6-dihydroimidazo[1,2-a]pyrazine-7(8H)-carboxylate

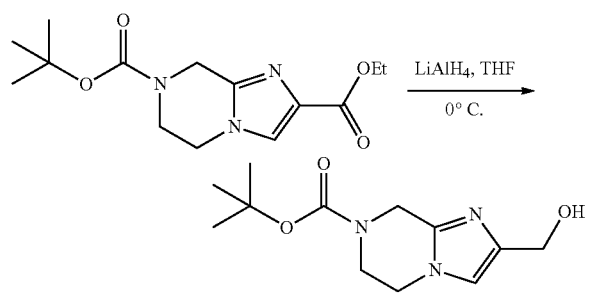

To a stirred solution of 7-tert-butyl 2-ethyl 5,6-dihydroimidazo[1,2-a]pyrazine-2,7(8H)-dicarboxylate (50 mg, 0.17 mmol) in anhydrous THF (2 mL) was added LiAlH$_4$ (13 mg, 0.34 mmol) batches at 0° C. The mixture was stirred at the same temperature for 30 minutes. TLC showed that the reaction was complete. The reaction was quenched with Na$_2$SO$_4$.10H$_2$O. The mixture was dried over anhydrous Na$_2$SO$_4$, filtered and concentrated in vacuo. The residue was purified by silica gel column chromatography (CH$_2$Cl$_2$:MeOH=50:1) to give a colorless oil (30 mg, 69.8%). $^1$H NMR (400 MHz, CDCl$_3$) δ 6.81 (s, 1H), 4.67 (s, 2H), 4.57 (s, 2H), 3.95 (d, J=5.2 Hz, 2H), 3.84 (s, 2H), 1.48 (s, 9H).

Method A—Step d: Preparation of (5,6,7,8-tetrahydroimidazo[1,2-a]pyrazin2-yl)methanol

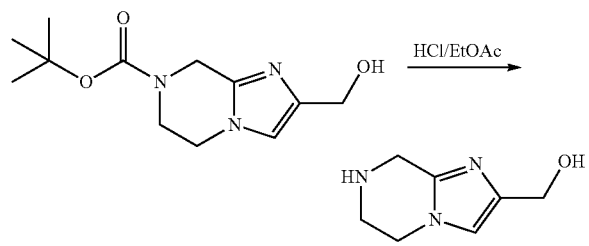

Tert-butyl 2-(hydroxymethyl)-5,6-dihydroimidazo[1,2-a]pyrazine-7(8H)-carboxylate (200 mg, 0.79 mmol) was dissolved in 3M HCl/ethyl acetate (3 mL). The mixture was stirred at room temperature for 4 hours, then the solvent was removed under vacuum. The residue was applied to silica gel column chromatography (CH$_2$Cl$_2$:MeOH:NH$_3$—H$_2$O=100:10:1) to give a yellow oil (100 mg, 82.6%). $^1$H NMR (400 MHz, CDCl$_3$) δ 6.77 (s, 1H), 4.57 (s, 2H), 4.09 (s, 2H), 3.94 (t, J=5.4 Hz, 2H), 3.24 (t, J=5.2 Hz, 2H).

Method A—Step e: Preparation of 2',5'-dichloro-3,5-dimethyl-2,4'-bipyridine

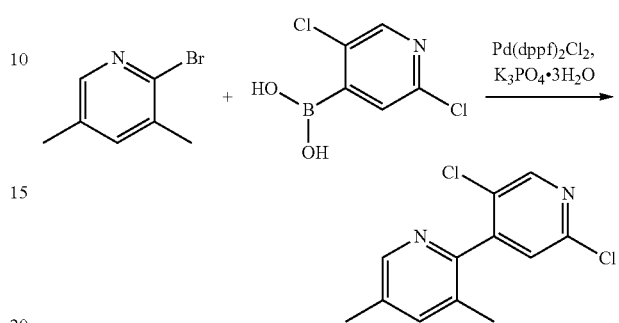

To a solution of 2,5-dichloropyridin-4-ylboronic acid (7.56 g, 40 mmol), 2-bromo-3,5-dimethylpyridine (5.62 g, 30 mol) in dioxane (60 mL) and H$_2$O (12 mL) were added Pd(dppf)Cl$_2$ (1.35 g, 1.7 mmol) and K$_3$PO$_4$.3H$_2$O (16.2 g, 60 mmol), the mixture was stirred at reflux under N$_2$ atmosphere overnight. TLC showed the reaction was complete, After cooling to room temperature, the mixture was filtered. Water (50 mL) was then added to the filtrate. The mixture was extracted with dichloromethane (150 mL×3). The combined organic layers were washed with brine (300 mL), dried over Na$_2$SO$_4$, filtered and concentrated. The residue was purified by silica gel column chromatography (petroleum ether/EtOAc=20:1 to 10:1) to give title compound (3.1 g, 41%) as a white solid. $^1$H NMR (400 MHz, CDCl$_3$): δ 8.46 (s, 1H), 8.37 (s, H), 7.47 (s, 1H), 7.33 (s, 1H), 2.39 (s, 3H), 2.16 (s, 3H).

Method A—Step f: Preparation of (7-(5'-chloro-3,5-dimethyl-2,4'-bipyridin-2'-yl)-5,6,7,8-tetrahydroimidazo[1,2-a]pyrazin-2-yl)methanol

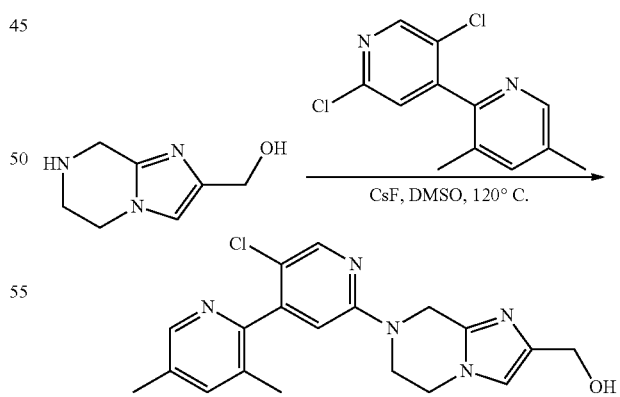

2',5'-Dichloro-3,5-dimethyl-2,4'-bipyridine (41 mg, 0.162 mmol) was dissolved in DMSO (2 mL) followed by addition of CsF (50 mg, 0.329 mmol) and (5,6,7,8-tetrahydroimidazo[1,2-a]pyrazin-2-yl)methanol (46 mg, 0.3 mmol). The mixture was stirred at 120° C. for 48 hours. Then the mixture was portioned between ethyl acetate (10 mL) and water (5 mL), the organic phase washed with brine (5 mL). The organic layer was concentrated under reduced pressure, purified by silica gel column chromatography (CH$_2$Cl$_2$:MeOH=40:1) to give a white solid (20 mg, 33.37%). $^1$H NMR (400 MHz, CDCl$_3$) δ 8.35 (s, 1H), 8.24 (s, 1H), 7.44 (s, 1H), 6.84 (s, 1H), 6.65 (s, 1H), 4.70 (s, 2H), 4.58 (s, 2H), 4.15 (s, 2H), 4.09 (s, 2H), 2.38 (s, 3H), 2.16 (s, 3H). ESI-MS (m/z): 370.1[M+1]$^+$.

Example 2

Preparation of 4-((7-(5'-chloro-3,5-dimethyl-2,4'-bipyridin-2'-yl)-5,6,7,8-tetrahydroimidazo[1,2-a]pyrazin-2-yl)methyl)morpholine (A-11)

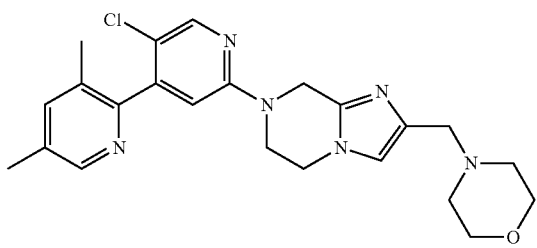 [SMILES: Cc1cnc(-c2cc(N3CCn4cc(CN5CCOCC5)nc4C3)ncc2Cl)c(C)c1]

Method B—Step g: Preparation of tert-butyl 2-(morpholinomethyl)-5,6-dihydroimidazo[1,2-a]pyrazine-7(8H)-carboxylate

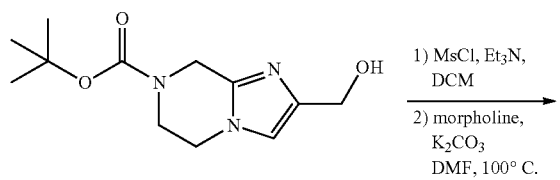

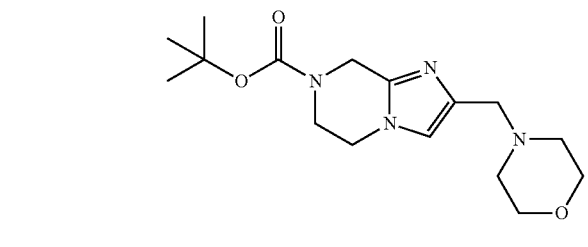

To a solution of tert-butyl 2-(hydroxymethyl)-5,6-dihydroimidazo[1,2-a]pyrazine-7(8H)-carboxylate (400 mg, 1.579 mmol) and triethylamine (320 mg, 3.158 mmol) in CH$_2$Cl$_2$ (4 mL) was added methanesulfonyl chloride (199 mg, 1.737 mmol) dropwise at 0° C. The mixture was stirred at room temperature for 30 minutes. TLC showed the reaction was complete. The reaction mixture was poured into 10 mL of ethyl acetate and washed with water (3 mL) twice. The organic layer was dried over Na$_2$SO$_4$ and concentrated in vacuo, then dissolved in DMF (8 mL) with K$_2$CO$_3$ (395 mg, 3.98 mmol), then morpholine (347 mg, 3.98 mmol) was added. The mixture was stirred at 100° C. for 2 hours. TLC showed that the reaction was complete. The reaction mixture was portioned between ethyl acetate (20 mL) and water (5 mL), washed with brine (5 mL×3). The organic layer was concentrated under reduced pressure, purified by silica gel column chromatography (CH$_2$Cl$_2$:MeOH=50:1) to give a brown oil (220 mg, 51.43%). $^1$H NMR (400 MHz, CDCl$_3$) δ 6.75 (s, 1H), 4.67 (s, 2H), 3.94 (d, J=2.6 Hz, 2H), 3.83 (s, 2H), 3.74 (m, J=4.4 Hz, 4H), 3.45 (s, 2H), 2.53 (s, 4H), 1.48 (s, 9H).

Method B—Step h: Preparation of 4-((5,6,7,8-tetrahydroimidazo[1,2-a]pyrazin-2-yl)methyl)morpholine

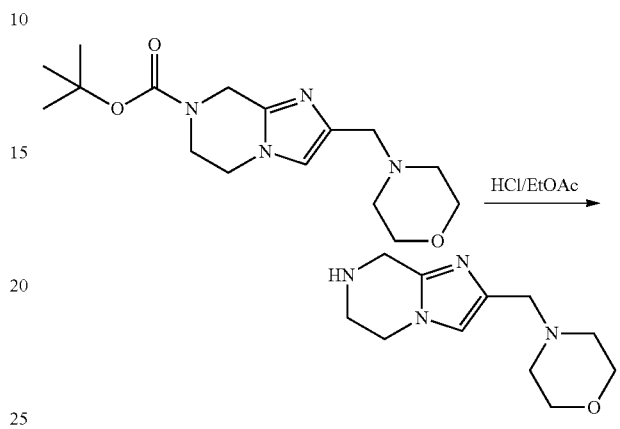

Tert-butyl2-(morpholinomethyl)-5,6-dihydroimidazo[1,2-a]pyrazine-7(8H)-carboxylate (170 mg, 0.527 mmol) was added to 3M HCl/ethyl acetate (3 mL). The mixture was stirred at room temperature for 2 hours, then the solvent was removed under vacuum. The residue was applied to flash chromatography (CH$_2$Cl$_2$:MeOH:NH$_3$—H$_2$O=100:10:1) to give a compound as a yellow oil (110 mg, 94.87%). $^1$H NMR (400 MHz, CDCl$_3$) δ 6.72 (s, 1H), 4.08 (s, 2H), 3.92 (s, 2H), 3.74 (s, 4H), 3.45 (s, 2H), 3.23 (s, 2H), 2.53 (s, 4H).

Method B—Step i: Preparation of 4-((7-(5'-chloro-3,5-dimethyl-2,4'-bipyridin-2'-yl)-5,6,7,8-tetrahydroimidazo[1,2-a]pyrazin-2-yl)methyl)morpholine

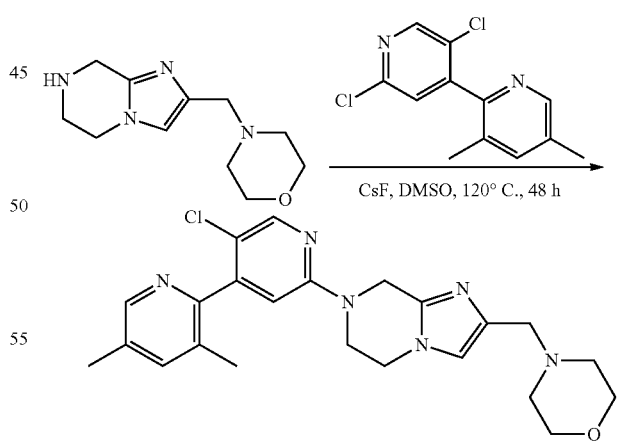

2',5'-Dichloro-3,5-dimethyl-2,4'-bipyridine (40 mg, 0.158 mmol) was dissolved in DMSO (1 mL) followed by addition of CsF (50 mg, 0.329 mmol) and 4-((5,6,7,8-tetrahydroimidazo[1,2-a]pyrazin-2-yl)methyl)morpholine (46 mg, 0.3 mmol). The mixture was stirred at 120° C. for 48 hours. Then it was portioned between ethyl acetate (10 mL) and water (5 mL), washed with brine (5 mL). The organic layer was concentrated under reduced pressure, purified by silica gel column chromatography (CH$_2$Cl$_2$:MeOH=25:1) to give a green oil (11 mg, 15.82%). $^1$H NMR (400 MHz, CDCl$_3$) δ 8.34 (s, 1H), 8.24 (s, 1H), 7.43 (s, 1H), 7.00 (s, 1H), 6.63 (s, 1H), 4.68 (s, 2H), 4.14 (s, 2H), 4.08 (s, 2H), 3.83 (s, 4H), 3.66 (s, 2H), 2.73 (s, 4H), 2.38 (s, 3H), 2.16 (s, 3H). ESI-MS (m/z): 438.8[M+1]$^+$.

Example 3

Preparation of (7-(5'-chloro-3,5-dimethyl-2,4'-bipyridin-2'-yl)-5,6,7,8-tetrahydroimidazo[1,2-a]pyrazin-2-yl)(pyrrolidin-1-yl)methanone (A-3)

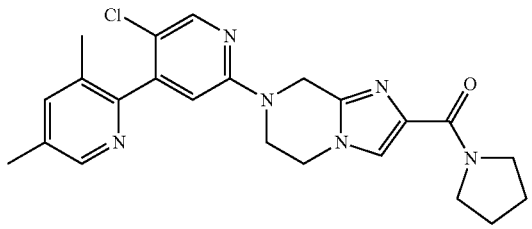 [SMILES: Cc1cnc(-c2cc(N3CCn4cc(C(=O)N5CCCC5)nc4C3)ncc2Cl)c(C)c1]

Method C—Step j: Preparation of ethyl 5,6,7,8-tetrahydroimidazo[1,2-a]pyrazine-2-carboxylate

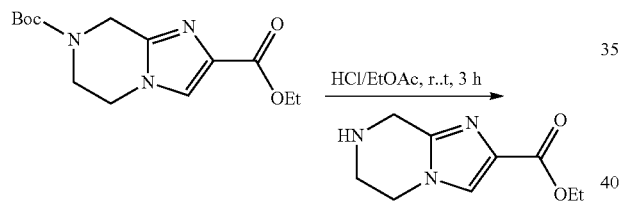

7-Tert-butyl 2-ethyl 5,6-dihydroimidazo[1,2-a]pyrazine-2,7(8H)-dicarboxylate (50 mg, 0.17 mmol) was dissolved in 3 mL of 3M HCl in ethyl acetate. The mixture was stirred at room temperature for 3 hours. The reaction mixture was filtered and washed with ethyl acetate. The solid was dissolved in water and added saturated NaHCO$_3$ aqueous solution until pH=7. The solution was applied to reverse phase chromatography to afford the final compound as a white solid (27.53 mg, 83%).

Method C—Step k: Preparation of ethyl 7-(5'-chloro-3,5-dimethyl-2,4'-bipyridin-2'-yl)-5,6,7,8-tetrahydroimidazo[1,2-a]pyrazine-2-carboxylate

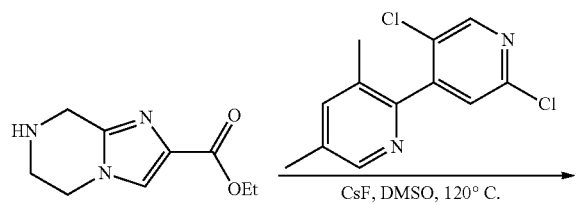

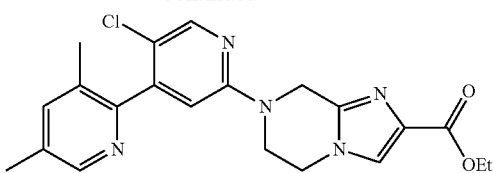

Ethyl 5,6,7,8-tetrahydroimidazo[1,2-a]pyrazine-2-carboxylate (385 mg, 4.0 mmol) was added to the solution of 2',5'-dichloro-3,5-dimethyl-2,4'-bipyridine (500 mg, 1.98 mmol) and CsF (300 mg, 4.0 mmol) in DMSO (1 mL). The mixture was stirred at 120° C. for 24 hours. The reaction mixture was diluted with 30 mL ethyl acetate and washed with brine (10 mL) for three times. The organic layer was dried over Na$_2$SO$_4$ and concentrated in vacuo. The residue was purified by silica gel column chromatography (CH$_2$Cl$_2$:MeOH=50:1) to give a white solid (0.7 g, 85%). 1H NMR (400 MHz, CDCl$_3$) δ 8.37 (s, 1H), 8.26 (s, 1H), 7.58 (s, 1H), 7.47 (s, 1H), 6.65 (s, 1H), 4.75 (s, 2H), 4.36 (q, J=7.2 Hz, 2H), 4.34 (br s, 4H), 2.62 (s, 3H), 2.20 (s, 3H), 1.39 (t, J=7.1 Hz, 3H). ESI-MS (m/z): 411.8[M+1]+.

Method C—Step l: Preparation of 7-(5'-chloro-3,5-dimethyl-2,4'-bipyridin-2'-yl)-5,6,7,8-tetrahydroimidazo[1,2-a]pyrazine-2-carboxylic acid

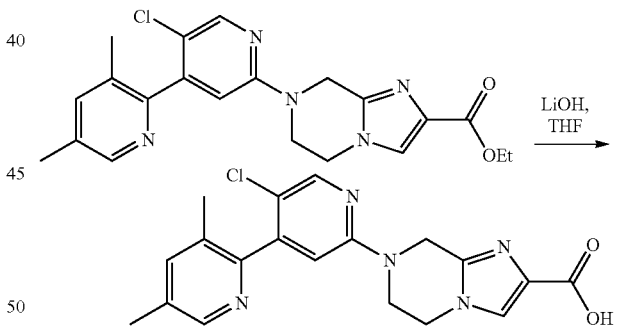

Ethyl 7-(5'-chloro-3,5-dimethyl-2,4'-bipyridin-2'-yl)-5,6,7,8-tetrahydroimidazo[1,2-a]pyrazine-2-carboxylate (700 mg, 1.7 mmol) was dissolved in the mixture solution of THF (10 mL) and 2 M LiOH aqueous solution (10 mL), the mixture was stirred at room temperature for 16 hours. TLC (CH$_2$Cl$_2$:MeOH=20:1) showed the reaction was complete, adjusted PH=7.0 with 1 M HCl solution and purified by reverse phase chromatography (H$_2$O:MeOH=55:45) to give desired compound (450 mg, 70%) as a white solid. 1H NMR (400 MHz, CDCl$_3$): δ 8.40 (s, 1H), 8.21 (s, 1H), 7.49 (s, 1H), 7.44 (s, 1H), 6.68 (s, 1H), 4.69 (s, 2H), 4.11 (br, 4H), 2.37 (s, 3H), 2.17 (s, 3H). ESI-MS (m/z): 383.8[M+1]+.

Method C—Step m: Preparation of (7-(5'-chloro-3, 5-dimethyl-2,4'-bipyridin-2'-yl)-5,6,7,8-tetrahydroimidazo[1,2-a]pyrazin-2-yl)(pyrrolidin-1-yl)methanone

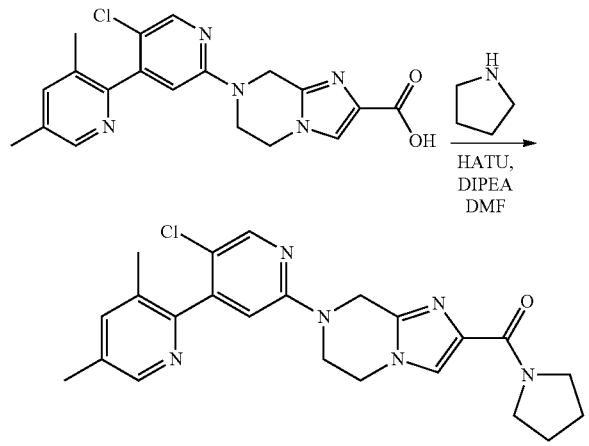

To a solution of 7-(5'-chloro-3,5-dimethyl-2,4'-bipyridin-2'-yl)-5,6,7,8-tetrahydroimidazo[1,2-a]pyrazine-2-carboxylic acid (50 mg, 0.13 mmol), HATU (55 mg, 0.14 mmol) and DIPEA (18.5 mg, 0.14 mmol) in DMF (1 mL) was added pyrrolidine (10 mg, 0.14 mmol), the mixture was stirred at room temperature for 16 hours. TLC showed the reaction was complete, diluted with EtOAc (10 mL) and the organic phase was washed with water (5 mL) and brine (5 mL). The organic layer was dried over $Na_2SO_4$, and the residue was purified by silica gel column chromatography ($CH_2Cl_2$:MeOH=50:1) to offer the tittle compound (15 mg, 26%) as a colorless oil; 1H NMR (400 MHz, $CDCl_3$): δ 8.36 (s, 1H), 8.24 (s, 1H), 7.53 (s, 1H), 7.44 (s, 1H), 6.68 (s, 1H), 4.72 (s, 2H), 4.15 (br, 4H), 3.95 (t, J=6.4 Hz, 2H), 3.63 (t, J=6.4 Hz, 2H), 2.39 (s, 3H), 2.18 (s, 3H) 1.93-1.87 (m, 4H). ESI-MS (m/z): 436.8[M+1]+.

Example 4

Preparation of N-(7-(5'-chloro-3,5-dimethyl-2,4'-bipyridin-2'-yl)-5,6,7,8-tetrahydroimidazo[1,2-a]pyrazin-2-yl)-2,2,2-trifluoroacetamide (A-12)

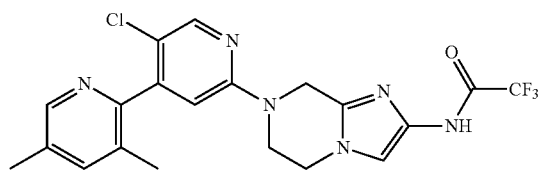 [SMILES: Cc1cnc(-c2cc(N3CCn4cc(NC(=O)C(F)(F)F)nc4C3)ncc2Cl)c(C)c1]

Method D—Step a: Preparation of 4-methyl-N-(pyrazin-2-yl)benzenesulfonamide

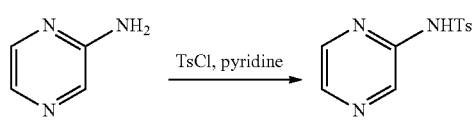

To a solution of pyrazin-2-amine (10 g, 105 mmol) in 80 mL of pyridine, paratoluensulfonyl chloride (22 g, 115.4 mmol) was added. The mixture was stirred at room temperature for 80 minutes. The solvent was removed, $H_2O$ (1 L) was added to the residue. The mixture was stirred at room temperature for 1 hour and filtered, the solid was washed with $H_2O$ (100 mL) and diethyl ether (200 mL) to obtain the title compound (19 g, 72.4%). 1H NMR (400 MHz, $CDCl_3$) δ 8.74 (s, 1H), 8.29 (d, J=5.6 Hz, 2H), 7.80 (d, J=7.6 Hz, 2H), 7.27 (d, J=7.6 Hz, 2H), 2.40 (s, 3H).

Method D—Step b: Preparation of 2,2,2-trifluoro-N-(imidazo[1,2-a]pyrazin-2-yl)acetamide

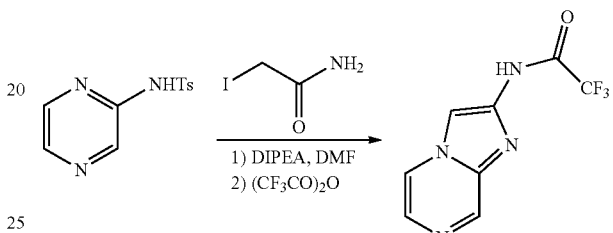

To a solution of 4-methyl-N-(pyrazin-2-yl)benzenesulfonamide (8.6 g, 34.5 mmol) in DMF (60 mL) were added iodoacetamide (7 g, 37.8 mmol) and DIPEA (6.6 mL, 37.9 mmol). The mixture was stirred at room temperature for 28 hours, 40 mL of $H_2O$ was added and stirred at room temperature for 100 minutes, filtered. The solid was washed with 200 mL of $H_2O$ and 100 mL of diethyl ether to obtain a gray solid which dissolved in the mixture of dichloromethane (110 mL) and trifluoroacetic anhydride (110 mL), the mixture was refluxed for 2 hours. After the mixture was concentrated, the residue was added to ethyl acetate (220 mL) to give a precipitate. The precipitate was washed with ethyl acetate to obtain a gray solid (5.2 g, 65%). 1H NMR (400 MHz, DMSO-d6) δ 12.71 (s, 1H), 8.98 (s, 1H), 8.63 (d, J=4.8 Hz, 1H), 8.40 (s, 1H), 7.93 (d, J=4.4 Hz, 1H).

Method D—Step c: Preparation of 2,2,2-trifluoro-N-(5,6,7,8-tetrahydroimidazo[1,2-a]pyrazin-2-yl)acetamide

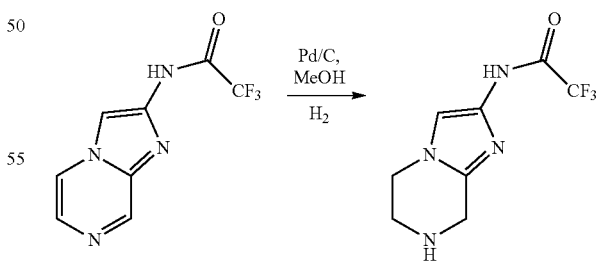

To a solution of 2,2,2-trifluoro-N-(imidazo[1,2-a]pyrazin-2-yl)acetamide (5.2 g, 22.61 mmol) in 130 mL of methanol was added 780 mg of Pd/C (50% wet), the mixture was stirred under hydrogen atmosphere for 10 hours. The reaction mixture was filtered through a pad of Celite, washed with methanol, and the filtrate was concentrated under reduced pressure. The residue was purified by silica gel column chromatography (CH₂Cl₂:MeOH=30:1) to provide the title compound as a white solid (1.3 g, 24.6%). 1H NMR (400 MHz, CDCl3) δ 9.74 (s, 1H), 7.29 (s, 1H), 4.02 (s, 2H), 3.96 (t, J=5.4 Hz, 2H), 3.27 (t, J=5.4 Hz, 2H).

Method D—Step d: Preparation of N-(7-(5'-chloro-3,5-dimethyl-2,4'-bipyridin-2'-yl)-5,6,7,8-tetrahydroimidazo[1,2-a]pyrazin-2-yl)-2,2,2-trifluoroacetamide

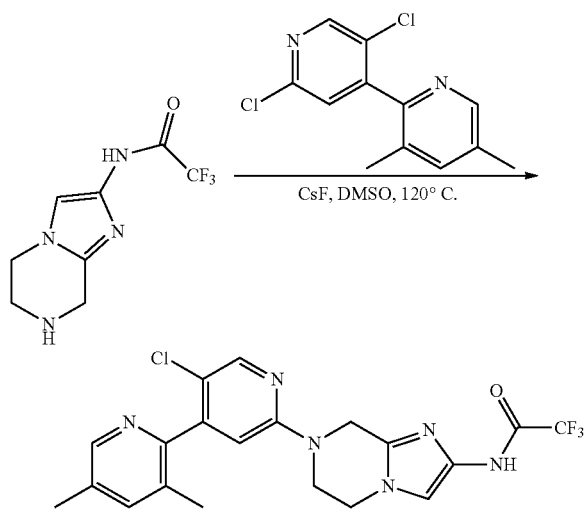

2,2,2-Trifluoro-N-(5,6,7,8-tetrahydroimidazo[1,2-a]pyrazin-2-yl)acetamide (800 mg, 3.1 mmol), CsF (2 g, 12.8 mmol) and 2',5'-dichloro-3,5-dimethyl-2,4'-bipyridine (500 mg, 2.1 mmol) were dissolved in DMSO (6 mL), the mixture was heated at 120° C. for 48 hours. Then the reaction mixture was cooled down and partitioned between ethyl acetate (100 mL) and H₂O (50 mL), the organic layer was washed with brine, dried over magnesium sulfate and concentrated. The residue was purified by chromatography (CH₂Cl₂:CH₃OH=50:1) to provide the title compound as a yellow solid (250 mg, 26%); 1H NMR (400 MHz, CDCl3) δ 10.76 (s, 1H), 8.34 (s, 1H), 8.25 (d, J=2.8 Hz, 1H), 7.43 (s, 1H), 7.36 (d, J=2.4 Hz, 1H), 6.64 (s, 1H), 4.63 (s, 2H), 4.11 (s, 4H), 2.37 (s, 3H), 2.16 (s, 3H). ESI-MS (m/z): 450.7[M+1]+.

Example 5

Preparation of N-(7-(5'-chloro-3,5-dimethyl-2,4'-bipyridin-2'-yl)-5,6,7,8-tetrahydroimidazo[1,2-a]pyrazin-2-yl)propionamide (A-13)

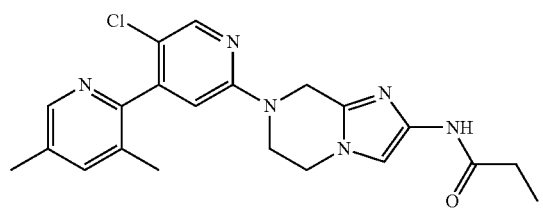 [SMILES: CCC(=O)Nc1cn2c(n1)CN(c1cc(-c3ncc(C)cc3C)c(Cl)cn1)CC2]

Method E—Step e: Preparation of imidazo[1,2-a]pyrazin-2-amine

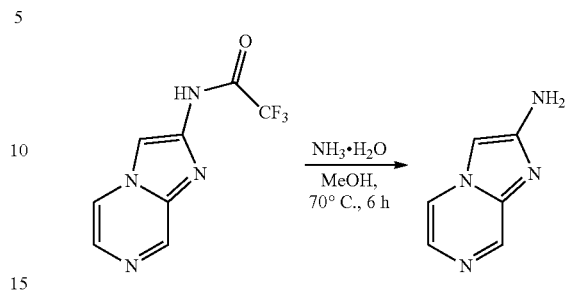

To a solution of 2,2,2-trifluoro-N-(imidazo[1,2-a]pyrazin-2-yl)acetamide (4.2 g, 18.26 mmol) in methanol (50 mL) was added NH₃—H₂O (20 mL), the mixture was stirred at 70° C. for 6 hours. The reaction mixture was cooled to room temperature and concentrated. The residue was purified by silica gel column chromatography (CH₂Cl₂:MeOH=30:1) to provide the title compound as a yellow solid (1.2 g, 44%). ¹H NMR (400 MHz, CDCl₃) δ 8.74 (s, 1H), 7.88 (d, J=4.8 Hz, 1H), 7.79 (d, J=4.4 Hz, 1H), 7.01 (s, 1H), 4.20 (s, 2H).

Method E—Step f: Preparation of N-(imidazo[1,2-a]pyrazin-2-yl)propionamide

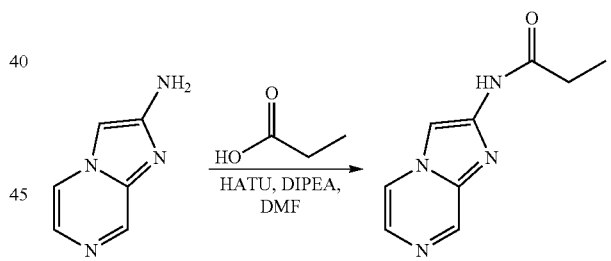

To a solution of imidazo[1,2-a]pyrazin-2-amine (300 mg, 2.238 mmol), propionic acid (216 mg, 2.91 mmol) in DMF (5 mL) were added HATU (1.1 g, 2.91 mmol) and DIPEA (774 mg, 6 mmol). The solution was stirred at room temperature for 24 hours. The mixture was partitioned between ethyl acetate (150 mL) and H₂O (40 mL), the organic layer was washed with brine (40 mL), dried over magnesium sulfate and concentrated. The residue was purified by silica gel column chromatography (CH₂Cl₂:MeOH=60:1) to provide the title compound (200 mg, 47%). ¹H NMR (400 MHz, CDCl₃) δ 8.90 (s, 1H), 8.57 (s, 1H), 8.21 (s, 1H), 8.05 (d, J=4.8 Hz, 1H), 7.91 (d, J=4.4 Hz, 1H), 2.50 (q, J=7.6 Hz, 2H), 1.28 (t, J=7.6 Hz, 3H).

Method E—Step g: Preparation of N-(5,6,7,8-tetra-hydroimidazo[1,2-a]pyrazin-2-yl)propionamide

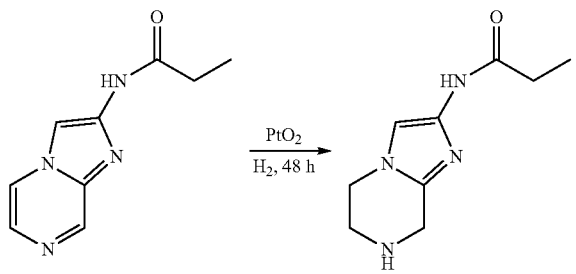

To a solution of N-(imidazo[1,2-a]pyrazin-2-yl)propionamide (150 mg, 0.79 mmol) in methanol (10 mL), PtO$_2$ (15 mg) was added. The mixture was stirred under hydrogen atmosphere at room temperature for 48 hours. The reaction mixture was filtered, washed with methanol. The filtrate was concentrated, the residue was purified by silica gel column chromatography (CH$_2$Cl$_2$:MeOH=30:1) to provide the title compound as a white solid (110 mg, 73%).

Method E—Step h: Preparation of N-(7-(5'-chloro-3,5-dimethyl-2,4'-bipyridin-2'-yl)-5,6,7,8-tetrahydroimidazo[1,2-a]pyrazin-2-yl)propionamide

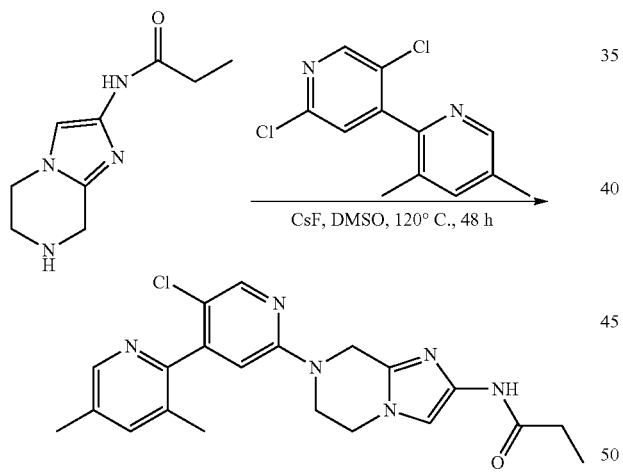

To a solution of N-(5,6,7,8-tetrahydroimidazo[1,2-a]pyrazin-2-yl)propionamide (40 mg, 0.206 mmol) and 2',5'-dichloro-3,5-dimethyl-2,4'-bipyridine (104 mg, 0.412 mmol) in DMSO (1.5 mL) was added CsF (188 mg, 1.236 mmol). The mixture was stirred at 120° C. for 48 hours. The reaction mixture was cooled down and partitioned between ethyl acetate (30 mL) and H$_2$O (5 mL), the organic layer was washed with brine (5 mL), dried with Na$_2$SO$_4$ and concentrated. The residue was purified by silica gel column chromatography (CH$_2$Cl$_2$:MeOH=60:1) to provide the title compound as a green solid (20 mg, 23.6%). $^1$H NMR (400 MHz, CDCl$_3$) δ 8.35 (s, 1H), 8.25 (s, 1H), 8.22 (s, 1H), 7.44 (s, 1H), 7.25 (s, 1H), 6.65 (s, 1H), 4.63 (s, 2H), 4.12 (s, 2H), 4.07 (d, J=4.0 Hz, 2H), 2.38-2.35 (m, 5H), 2.17 (s, 3H), 1.22 (t, J=7.8 Hz, 3H). ESI-MS (m/z): 410.9[M+1]$^+$.

Example 6

Preparation of N-(5-(5'-chloro-3,5-dimethyl-[2,4'-bipyridin]-2'-yl)-4,5,6,7-tetrahydrothiazolo[5,4-c]pyridin-2-yl)acetamide (A-23)

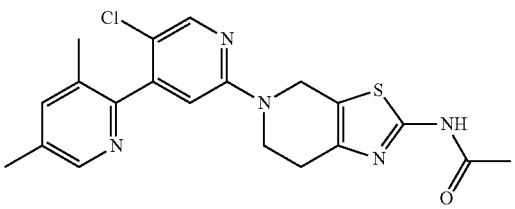 [SMILES: CC(=O)Nc1nc2c(s1)CN(c1cc(-c3ncc(C)cc3C)c(Cl)cn1)CC2]

Method F—Step a: Tert-butyl 2-amino-6,7-dihydrothiazolo[5,4-c]pyridine-5(4H)-carboxylate

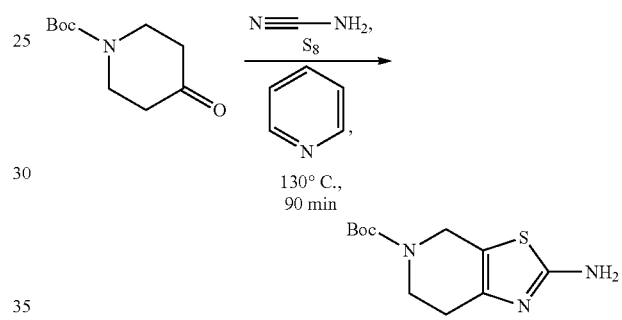

Tert-butyl 4-oxopiperidine-1-carboxylate (20 g, 101 mmol) was added to 100 mL of pyridine followed by addition of cyanamide (8.7 g, 201 mmol) and sublimed sulfur (6.4 g, 200 mmol). The mixture was stirred at 130° C. for 90 minutes and cooled down to room temperature. Filtered and washed with diethyl ether (100 mL) twice to give a pale yellow solid (19 g, 74.2%). $^1$H NMR (400 MHz, DMSO-d6) δ 6.83 (s, 2H), 4.29 (s, 2H), 3.56 (s, 2H), 2.43 (s, 2H), 1.41 (s, 9H).

Method F—Step b: 4,5,6,7-tetrahydrothiazolo[5,4-c]pyridin-2-amine

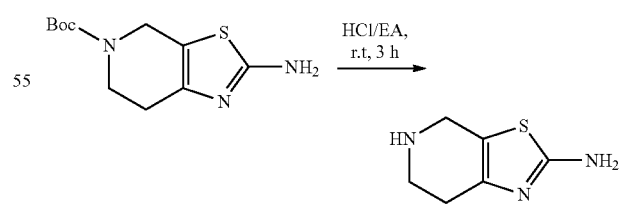

Tert-butyl 2-amino-6,7-dihydrothiazolo[5,4-c]pyridine-5(4H)-carboxylate (200 mg, 0.78 mmol) was dissolved in 3M HCl/ethyl acetate (3 mL). The mixture was stirred at room temperature for 3 hours, then the solvent was removed by vacuum, and the residue was portioned between CH$_2$Cl$_2$ (20 mL) and saturated aqueous sodium bicarbonate (5 mL), the organic layer was separated, dried over Na₂SO₄ and concentrated to give a white solid (105 mg, 87%).

Method F—Step c: 5-(5'-chloro-3,5-dimethyl-[2,4'-bipyridin]-2'-yl)-4,5,6,7-tetrahydrothiazolo[5,4-c]pyridin-2-amine

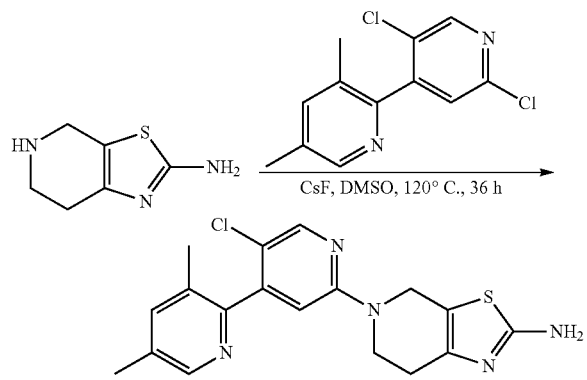

2',5'-Dichloro-3,5-dimethyl-2,4'-bipyridine (180 mg, 0.7 mmol) was dissolved in DMSO (1 mL) followed by addition of CsF (152 mg, 1 mmol) and 4,5,6,7-tetrahydrothiazolo[5,4-c]pyridin-2-amine (55 mg, 0.35 mmol). The mixture was stirred at 120° C. for 36 hours. Then the mixture was portioned between ethyl acetate (10 mL) and water (5 mL), washed with brine (5 mL). The organic layer was dried over Na₂SO₄ and concentrated under reduced pressure, purified by silica gel column chromatography (MeOH:CH₂Cl₂=1:100) to give a yellow oil (50 mg, 37.8%). $^1$H NMR (400 MHz, CDCl₃) δ 8.35 (s, 1H), 8.21 (s, 1H), 7.44 (s, 1H), 6.65 (s, 1H), 4.56 (s, 2H), 3.86 (s, 2H), 2.75 (s, 2H), 2.38 (s, 3H), 2.17 (s, 3H). ESI-MS (m/z): 371.8[M+1]⁺.

Method F—Step d: Preparation of N-(5-(5'-chloro-3,5-dimethyl-[2,4'-bipyridin]-2'-yl)-4,5,6,7-tetrahydrothiazolo[5,4-c]pyridin-2-yl)acetamide

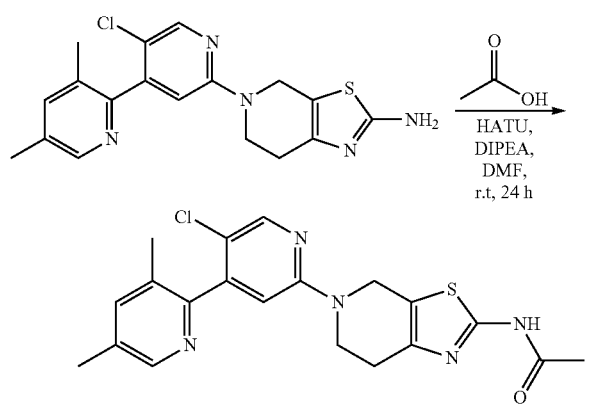

5-(5'-Chloro-3,5-dimethyl-[2,4'-bipyridin]-2'-yl)-4,5,6,7-tetrahydrothiazolo[5,4-c]pyridin-2-amine (40 mg, 0.11 mmol), acetic acid (9 mg, 0.14 mmol) and DIPEA (28 mg, 0.22 mmol) were dissolved in DMF (1.5 mL), and HATU (53 mg, 0.14 mmol) was added to the solution. The mixture was stirred at room temperature for 24 hours. The mixture was added to ethyl acetate (40 mL) and the solution was washed with brine (15 mL×3). The organic layer was dried over Na₂SO₄ and concentrated. The residue was purified by silica gel column chromatography (CH₂Cl₂:MeOH=70:1) to give title compound (20 mg, 45%) as a yellow solid. $^1$H NMR (400 MHz, CDCl₃) δ 9.55 (s, 1H), 8.35 (s, 1H), 8.22 (s, 1H), 7.43 (s, 1H), 6.66 (s, 1H), 4.68 (s, 2H), 3.96 (t, J=5.6 Hz, 2H), 2.83 (t, J=5.4 Hz, 2H), 2.38 (s, 3H), 2.23 (s, 3H), 2.17 (s, 3H). ESI-MS (m/z): 413.8[M+1]⁺.

Example 7

Preparation of 4-(5-(5'-chloro-3,5-dimethyl-[2,4'-bipyridin]-2'-yl)-4,5,6,7-tetrahydrothiazolo[5,4-c]pyridin-2-yl)morpholine (A-29)

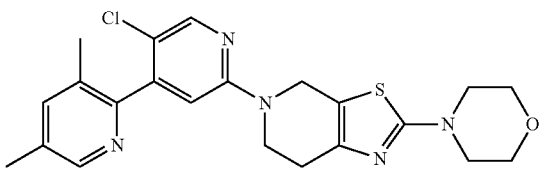 [SMILES: Cc1cnc(-c2cc(N3CCc4nc(N5CCOCC5)sc4C3)ncc2Cl)c(C)c1]

Method G—Step e: Tert-butyl 2-bromo-6,7-dihydrothiazolo[5,4-c]pyridine-5(4H)-carboxylate

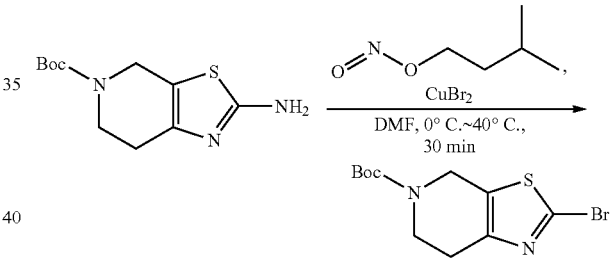

To a solution of isopentyl nitrite (8.8 mL, 62.8 mmol) and CuBr₂ (10.7 g, 48 mmol) in 100 mL of DMF was added tert-butyl 2-amino-6,7-dihydrothiazolo[5,4-c]pyridine-5(4H)-carboxylate (10 g, 39.2 mmol) at 0° C. The mixture was stirred at 40° C. for 30 min and evaporated. It was added to 50 mL of H₂O and extracted with CH₂Cl₂ (100 mL×2). The combined organics were washed with brine (30 mL×2) and dried over Na₂SO₄. Concentrated and purified by silica gel column chromatography (CH₂Cl₂) to give title compound (5.3 g, 42.4%) as a yellow solid.

Method G—Step f: Tert-butyl 2-morpholino-6,7-dihydrothiazolo[5,4-c]pyridine-5(4H)-carboxylate

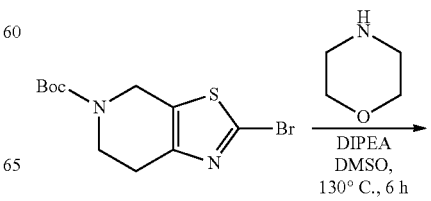

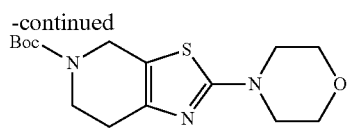

To a solution of tert-butyl 2-bromo-6,7-dihydrothiazolo[5,4-c]pyridine-5(4H)-carboxylate (200 mg, 0.629 mmol) and DIPEA (428 mg, 3.32 mmol) in 2 mL of DMSO was added morpholine (231 mg, 2.656 mmol). The mixture was stirred at 130° C. for 6 h. It was added to 40 mL of ethyl acetate and washed with brine (15 mL×3). The organic layer was dried over Na₂SO₄ and concentrated. It was purified by silica gel column chromatography (petroleum ether/EtOAc=4:1) to give title compound (130 mg, 63.7%) as a white solid.

Method G—Step g: 4-(4,5,6,7-tetrahydrothiazolo[5,4-c]pyridin-2-yl)morpholine

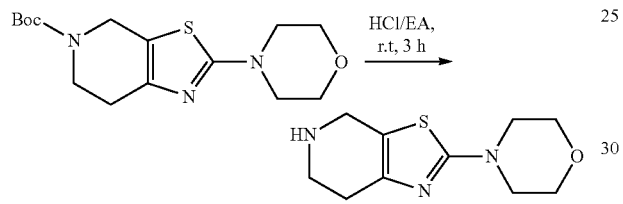

Tert-butyl 2-morpholino-6,7-dihydrothiazolo[5,4-c]pyridine-5(4H)-carboxylate (130 mg, 0.4 mmol) was added to 3M HCl/ethyl acetate (3 mL). The mixture was stirred at room temperature for 3 h, then the solvent was removed by vacuum, and the residue was portioned between CH₂Cl₂ (20 mL) and saturated aqueous sodium bicarbonate (5 mL), the organic layer was separated, dried over Na₂SO₄ and concentrated to give a white solid (50 mg, 55.5%).

Method G—Step h: 4-(5-(5'-chloro-3,5-dimethyl-[2,4'-bipyridin]-2'-yl)-4,5,6,7-tetrahydrothiazolo[5,4-c]pyridin-2-yl)morpholine

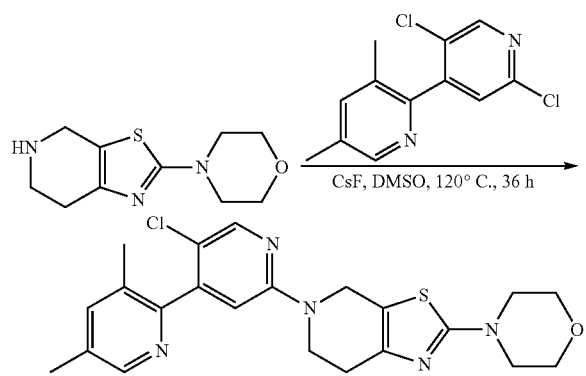

2',5'-Dichloro-3,5-dimethyl-2,4'-bipyridine (111 mg, 0.44 mmol) was dissolved in DMSO (1 mL) followed by addition of CsF (100 mg, 0.66 mmol) and 4-(4,5,6,7-tetrahydrothiazolo[5,4-c]pyridin-2-yl)morpholine (50 mg, 0.22 mmol). The mixture was stirred at 120° C. for 36 h. Then it was portioned between ethyl acetate (10 mL) and water (5 mL), washed with brine (5 mL). The organic layer was dried over Na₂SO₄ and concentrated under reduced pressure, purified by silica gel column chromatography (MeOH:CH₂Cl₂=1:70) to give a white solid (33 mg, 33.6%). ¹H NMR (400 MHz, CDCl₃) δ 8.38 (s, 1H), 8.24 (s, 1H), 7.45 (s, 1H), 6.68 (s, 1H), 4.63 (s, 2H), 3.93 (t, J=5.7 Hz, 2H), 3.82 (t, J=4.8 Hz, 4H), 3.44 (t, J=4.8 Hz, 4H), 2.80 (t, J=5.4 Hz, 2H), 2.40 (s, 3H), 2.19 (s, 3H). ESI-MS (m/z): 441.8[M+1]⁺.

Example 8

Preparation of 5-(5'-chloro-3,5-dimethyl-[2,4'-bipyridin]-2'-yl)-2-(pyrrolidin-1-yl)-6,7-dihydrothiazolo[5,4-c]pyridin-4(5H)-one (A-49)

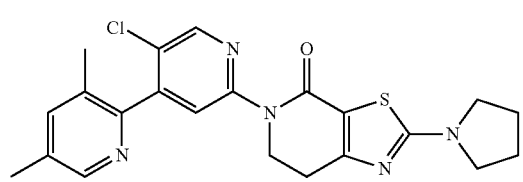 [SMILES: Cc1cnc(-c2cc(N3CCc4nc(N5CCCC5)sc4C3=O)ncc2Cl)c(C)c1]

Method H—Step a: Tert-butyl (3-(2,2-dimethyl-4,6-dioxo-1,3-dioxan-5-yl)-3-oxo-propyl)carbamate

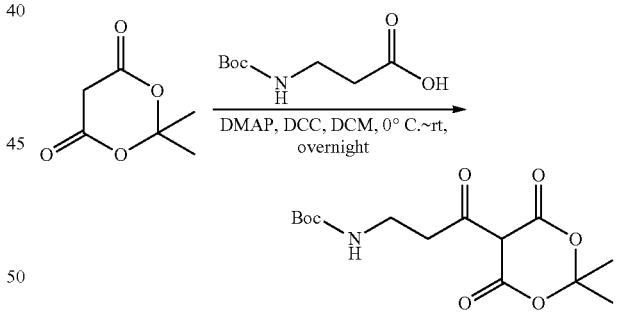

To a solution of DMAP (5.8 g, 47.36 mmol), 2,2-dimethyl-1,3-dioxane-4,6-dione (5 g, 34.72 mmol) and 3-((tert-butoxycarbonyl)amino)propanoic acid (5.96 g, 31.57 mmol) in 40 mL of CH₂Cl₂ was added the solution of DCC (7.8 g, 37.88 mmol) in 20 mL of CH₂Cl₂ dropwise at 0° C. The mixture was stirred at room temperature overnight. Filtered and the filtrate was washed with the solution of citric acid (5 g, 26 mmol) in 100 mL of water twice and water (100 mL). The organic layer was dried over Na₂SO₄ and concentrated under reduced pressure to obtain the crude compound (11 g) as a yellow solid that was used without further purification in the subsequent step.

Method H—Step b: Tert-butyl 2,4-dioxopiperidine-1-carboxylate

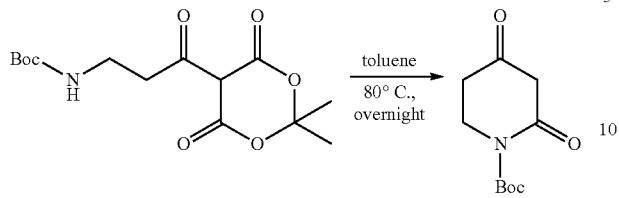

Tert-butyl (3-(2,2-dimethyl-4,6-dioxo-1,3-dioxan-5-yl)-3-oxopropyl)carbamate (11 g, 34.9 mmol) was dissolved in 200 mL of toluene and the solution was stirred at 80° C. overnight. Evaporated and purified by column chromatography (CH$_2$Cl$_2$:MeOH=100:1) to give a white solid (2.5 g, 33.7% for two steps). $^1$H NMR (400 MHz, CDCl$_3$) δ 4.13 (t, J=6.0 Hz, 2H), 3.54 (s, 2H), 2.65 (t, J=6.0 Hz, 2H), 1.58 (s, 9H).

Method H—Step c: Tert-butyl 3-bromo-2,4-dioxopiperidine-1-carboxylate

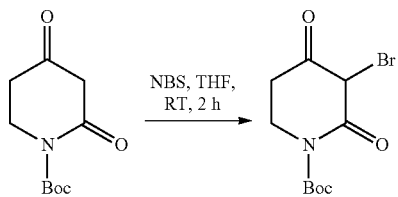 [SMILES: CC(C)(C)OC(=O)N1CCC(=O)CC1=O ; CC(C)(C)OC(=O)N1CCC(=O)C(Br)C1=O]

To a mixture of tert-butyl 2,4-dioxopiperidine-1-carboxylate (213 mg, 1 mmol) in THF (4 mL) was added N-bromosuccinimide (178 mg, 1 mmol) portionwise at 0° C. The mixture was further stirred at room temperature for 2 hours. The reaction mixture was treated with brine (5 mL) and extracted with ethyl acetate (10 mL). The organic layer was dried over Na$_2$SO$_4$ and concentrated under reduced pressure to obtain the crude compound (292 mg) as a white solid that was used without further purification in the subsequent step.

Method H—Step d: Tert-butyl 2-amino-4-oxo-6,7-dihydrothiazolo[5,4-c]pyridine-5(4H)-carboxylate

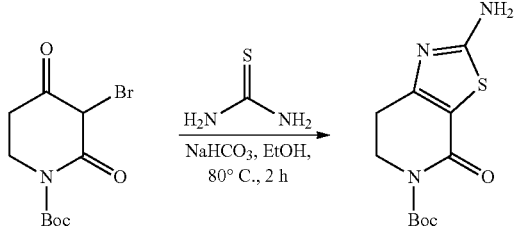

A mixture of tert-butyl 3-bromo-2,4-dioxopiperidine-1-carboxylate (292 mg, 1 mmol), thiourea (76 mg, 1 mmol) and NaHCO$_3$ (84 mg, 1 mmol) in ethanol (4 mL) was heated at 80° C. for 2 hours. The reaction mixture was then cooled to room temperature and the solids were filtered off. The filtrate was evaporated in vacuo to give a residue that was crystallized from EtOH. The white crystals thus obtained were filtered off and dried to yield 200 mg (74.3% for two steps). $^1$H NMR (400 MHz, DMSO-d6) δ 8.08 (s, 2H), 3.89 (t, J=6.4 Hz, 2H), 2.75 (t, J=6.4 Hz, 2H), 1.44 (s, 9H).

Method H—Step e: Tert-butyl 2-bromo-4-oxo-6,7-dihydrothiazolo[5,4-c]pyridine-5(4H)-carboxylate

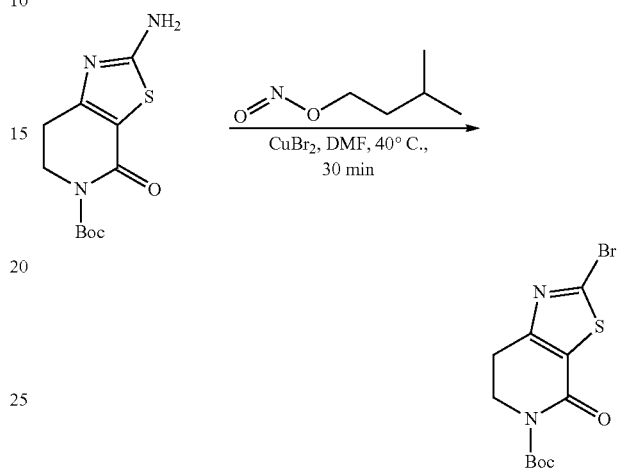

To a solution of isopentyl nitrite (176 mg, 1.5 mmol) and CuBr$_2$ (268 mg, 1.2 mmol) in 2.5 mL of DMF was added tert-butyl 2-amino-4-oxo-6,7-dihydrothiazolo[5,4-c]pyridine-5(4H)-carboxylate (269 mg, 1 mmol) at 0° C. The mixture was stirred at 40° C. for 30 min. It was added to 20 mL of brine and extracted with ethyl acetate (30 mL×2). The combined organics were washed with brine (10 mL×2) and dried over Na$_2$SO$_4$. Concentrated and purified by silica gel column chromatography (petroleum ether:EtOAc=20:1) to give the title compound (150 mg, 45%) as a white solid. $^1$H NMR (400 MHz, CDCl$_3$) δ 4.12 (t, J=6.4 Hz, 2H), 3.10 (t, J=6.4 Hz, 2H), 1.56 (s, 9H).

Method H—Step f: 2-(pyrrolidin-1-yl)-6,7-dihydrothiazolo[5,4-c]pyridin-4(5H)-one

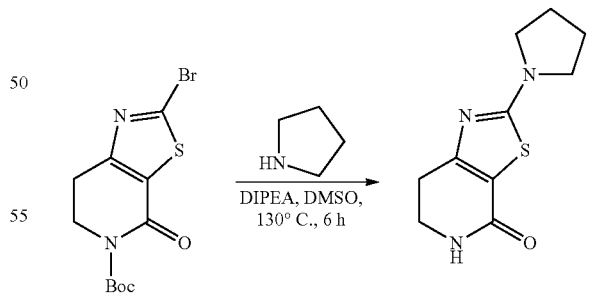

To a solution of tert-butyl 2-bromo-4-oxo-6,7-dihydrothiazolo[5,4-c]pyridine-5(4H)-carboxylate (111 mg, 0.333 mmol) and DIPEA (156 mg, 1.2 mmol) in 2 mL of DMSO was added pyrrolidine (71 mg, 1 mmol). The mixture was stirred at 130° C. for 6 h. It was added to 20 mL of brine and extracted with CH$_2$Cl$_2$ (20 mL×3). The combined organics was washed with brine (15 mL×2). The organic layer was dried over Na$_2$SO$_4$ and concentrated. It was purified by chromatography on silica gel (CH$_2$Cl$_2$:MeOH=60:1) to give the title compound (70 mg, 94%) as a yellow solid. $^1$H NMR (400 MHz, CDCl$_3$) δ 5.61 (s, 1H), 3.59-3.55 (m, 2H), 3.51 (s, 4H), 2.89 (t, J=7 Hz, 2H), 2.09-2.06 (m, 4H).

Method H—Step g: 5-(5'-chloro-3,5-dimethyl-[2,4'-bipyridin]-2'-yl)-2-(pyrrolidin-1-yl)-6,7-dihydrothiazolo[5,4-c]pyridin-4(5H)-one

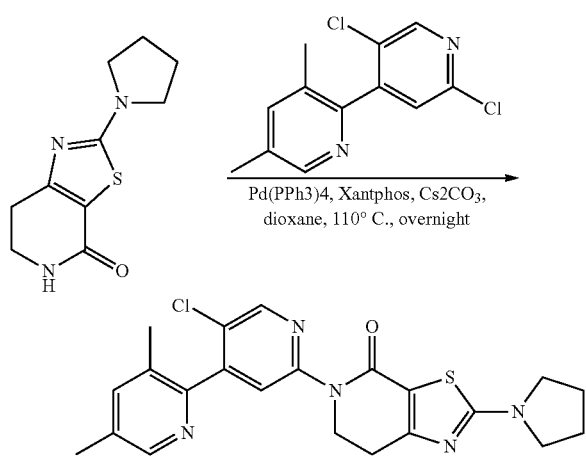

Pd(PPh$_3$)$_4$ (4 mg, 0.0034 mmol), Xantphos (4 mg, 0.0068 mmol), Cs$_2$CO$_3$ (40 mg, 0.123 mmol), 2-(pyrrolidin-1-yl)-6,7-dihydrothiazolo[5,4-c]pyridin-4(5H)-one (20 mg, 0.096 mmol) and 2',5'-dichloro-3,5-dimethyl-2,4'-bipyridine (20 mg, 0.079 mmol) were added to 4 mL of dioxane under nitrogen atmosphere. The mixture was stirred at 110° C. overnight. After cooling, the reaction mixture was evaporated and purified by chromatography on silica gel (petroleum ether:EtOAc=4:1) to give the title compound (16 mg, 47.6%) as a yellow solid. $^1$H NMR (400 MHz, CDCl$_3$) δ 8.43 (s, 1H), 8.33 (s, 1H), 7.93 (s, 1H), 7.42 (s, 1H), 4.37 (t, J=6.6 Hz, 2H), 3.53 (s, 4H), 3.01 (t, J=6.6 Hz, 2H), 2.36 (s, 3H), 2.22 (s, 3H), 2.10-2.07 (m, 4H). ESI-MS (m/z): 440.3 [M+1]$^+$.

Example 9

Preparation of 6-(5'-chloro-3,5-dimethyl-2,4'-bipyridin-2'-yl)-N-cyclopropyl-5,6,7,8-tetrahydropyrido[4,3-d]pyrimidin-2-amine (A-52)

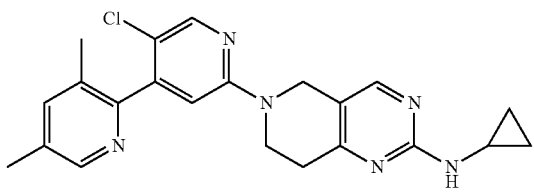

Method I—Step a: Tert-butyl 3-((dimethylamino)methylene)-4-oxopiperidine-1-carboxylate

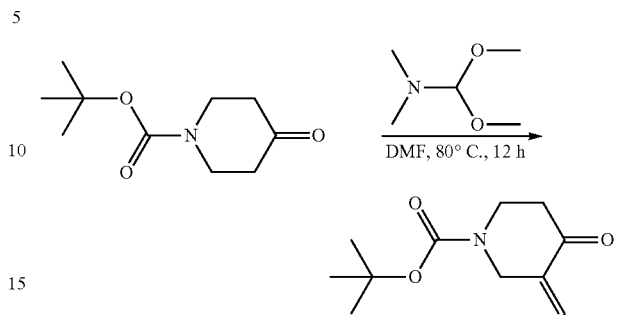

A solution of tert-butyl 4-oxopiperidine-1-carboxylate (10 g, 50.25 mmol) and 1,1-dimethoxy-N,N-dimethylmethanamine (6 g, 50 mmol) in 40 mL of dry N,N-dimethylacetamide was heated at 80° C. for 12 hours. The solution was cooled down and concentrated under reduced pressure, and the residue was portioned between ethyl acetate (150 mL) and water (50 mL). The organic layer was washed with brine (50 mL×2), dried over anhydrous sodium sulfate and concentrated under reduced pressure to afford an orange oil for next step without further purification (13 g).

Method I—Step b: Tert-butyl 2-(methylthio)-7,8-dihydropyrido[4,3-d]pyrimidine-6(5H)-carboxylate

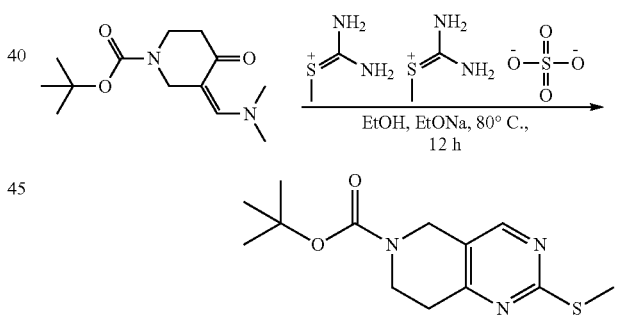

2-Methylthiouronium sulfate (6.98 g, 25.10 mmol) in 40 mL of ethanol was treated with sodium ethoxide (3.28 g, 40 mmol). After 30 min, a solution of the tert-butyl 3-((dimethylamino)methylene)-4-oxopiperidine-1-carboxylate (13 g) in 20 mL ethanol was added, and the mixture was stirred at 80° C. for 12 hours. The dark solution was cooled down to room temperature, concentrated under reduced pressure, and the residue was portioned between ethyl acetate (200 mL) and water (100 mL). The organic layer was washed with brine (100 mL), dried over sodium sulfate, and concentrated. Purification by column chromatography (CH$_2$Cl$_2$:EtOAc=25:1) afforded the compound as an orange oil (7.38 g, 52.3%). $^1$H NMR (400 MHz, CDCl$_3$) δ 8.24 (s, 1H), 4.50 (s, 2H), 3.69 (t, J=5.9 Hz, 2H), 2.86 (t, J=5.8 Hz, 2H), 2.52 (s, 3H), 1.47 (s, 9H).

Method I—Step c: Tert-butyl 2-(methylsulfonyl)-7, 8-dihydropyrido[4,3-d]pyrimidine-6(5H)-carboxylate

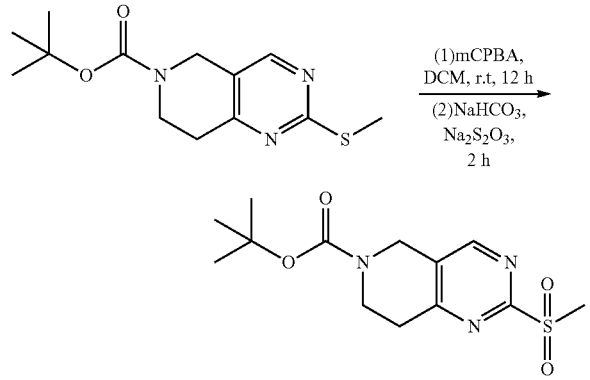

Tert-butyl 2-(methylthio)-7,8-dihydropyrido[4,3-d]pyrimidine-6(5H)-carboxylate (7.38 g, 26.26 mmol) was dissolved in 50 mL $CH_2Cl_2$ followed by addition of 3-chlorobenzoperoxoic acid (75%, 12.5 g, 54.50 mmol) slowly at 0° C. The mixture was stirred at r.t for 12 h. Then saturated $NaHCO_3$ solution (10 mL) and saturated $Na_2S_2O_3$ solution (10 mL) were added, stirred at r.t for 2 h. The organic layer was separated and concentrated under reduced pressure. Purification by silica gel column chromatography (petroleum ether:EtOAc=3:1) to afforded a white solid (5.5 g, 66.9%). $^1H$ NMR (400 MHz, $CDCl_3$) δ 8.63 (s, 1H), 4.70 (s, 2H), 3.79 (t, J=5.9 Hz, 2H), 3.33 (s, 3H), 3.09 (t, J=5.8 Hz, 2H), 1.49 (s, 9H).

Method I—Step d: Tert-butyl 2-(cyclopropylamino)-7,8-dihydropyrido[4,3-d]pyrimidine-6(5H)-carboxylate

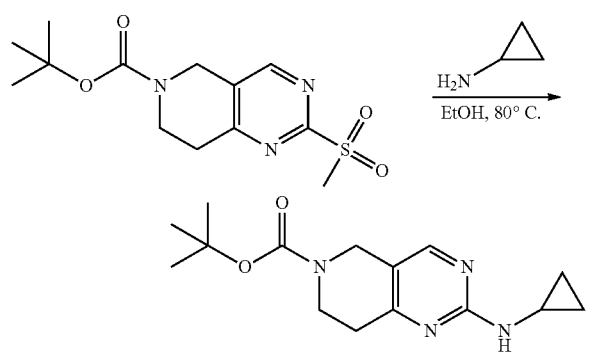

Tert-butyl 2-(methylsulfonyl)-7,8-dihydropyrido[4,3-d]pyrimidine-6(5H)-carboxylate (1 g, 3.195 mmol) was dissolved in was dissolved in 10 mL of ethanol followed by addition of cyclopropylamine (300 mg, 5.263 mmol). The mixture was stirred at 80° C. for 12 hours. The solvent was removed by vacuum, and the residue was purified by column chromatography (petroleum ether:EtOAc=4:1) to give a white solid (460 mg, 50.4%).

Method I—Step e: N-Cyclopropyl-5,6,7,8-tetrahydropyrido[4,3-d]pyrimidin-2-amine

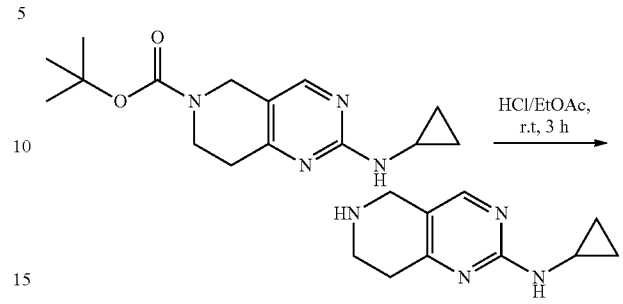

Tert-butyl 2-(cyclopropylamino)-7,8-dihydropyrido[4,3-d]pyrimidine-6(5H)-carboxylate (460 mg, 1.586 mmol) was dissolved in 3M HCl/EtOAc (3 mL). The mixture was stirred at room temperature for 3 hours, then the solvent was removed by vacuum, and the residue was portioned between $CH_2Cl_2$ (20 mL) and saturated aqueous sodium bicarbonate (5 mL), the organic layer was separated, dried over $Na_2SO_4$ and concentrated to give a white solid (270 mg, 89.6%).

Method I—Step f: 6-(5'-Chloro-3,5-dimethyl-2,4'-bipyridin-2'-yl)-N-cyclopropyl-5,6,7,8-tetrahydropyrido[4,3-d]pyrimidin-2-amine

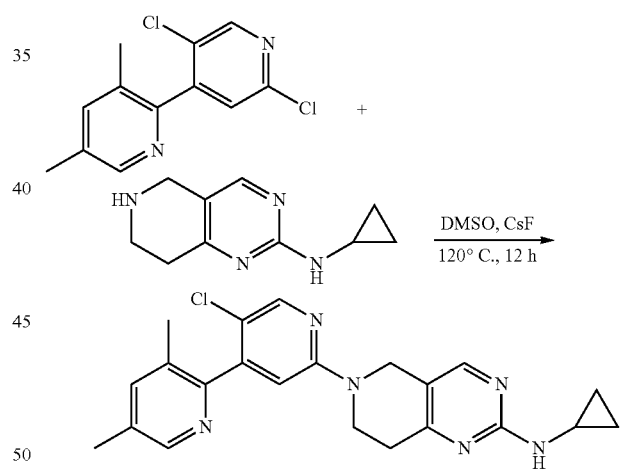

2',5'-Dichloro-3,5-dimethyl-2,4'-bipyridine (50 mg, 0.20 mmol) was dissolved in DMSO (1 mL) followed by addition of CsF (50 mg, 0.33 mmol) and N-cyclopropyl-5,6,7,8-tetrahydropyrido[4,3-d]pyrimidin-2-amine (100 mg, 0.53 mmol). The mixture was stirred at 120° C. for 12 hours. Then the mixture was portioned between ethyl acetate (10 mL) and water (5 mL), washed with brine (5 mL). The organic layer was concentrated under reduced pressure, purified by silica gel column chromatography ($CH_2Cl_2$:MeOH=100:1) to give a white solid (30 mg, 40%). $^1H$ NMR (400 MHz, $CDCl_3$) δ 8.39 (s, 1H), 8.23 (s, 1H), 8.17 (s, 1H), 7.42 (s, 1H), 6.65 (s, 1H), 4.55 (s, 2H), 3.90 (t, J=5.6 Hz, 2H), 2.88 (t, J=5.8 Hz, 2H), 2.77 (m, 1H), 2.42 (s, 3H), 2.21 (s, 3H), 1.29 (s, 1H), 0.87-079 (m, 2H), 0.62-0.55 (m, 2H). ESI-MS (m/z): 406.9[M+1]$^+$.

Example 10

Preparation of ethyl 6-(5'-chloro-3,5-dimethyl-2,4'-bipyridin-2'-yl)-5,6,7,8-tetrahydropyrido[4,3-d]pyrimidin-2-ylcarbamate (A-90)

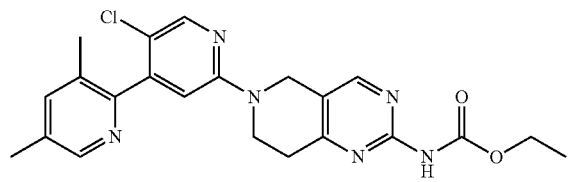 [SMILES: CCOC(=O)Nc1ncc2c(n1)CCN(c1cc(-c3ncc(C)cc3C)c(Cl)cn1)C2]

Method J—Step a: Tert-butyl 3-((dimethylamino)methylene)-4-oxopiperidine-1-carboxylate

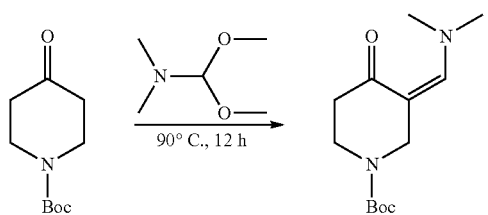

A solution of tert-butyl 4-oxopiperidine-1-carboxylate (2 g, 10.1 mmol) and 1,1-dimethoxy-N,N-dimethylmethanamine (18 g, 151.5 mmol) was heated at 90° C. for 12 hours. The reaction mixture was cooled to room temperature, and the solvent was removed. The residue was portioned between EtOAc and water. The organic layer was washed with brine, dried over anhydrous sodium sulfate and concentrated under reduced pressure to afford an orange oil for next step without further purification (3.10 g).

Method J—Step b: Tert-butyl 2-amino-7,8-dihydropyrido[4,3-d]pyrimidine-6(5H)-carboxylate

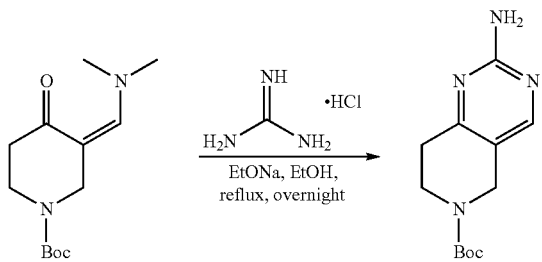

The mixture of guanidine hydrochloride (1.9 g, 20 mmol) and sodium ethylate (1.36 g, 20 mmol) in ethanol (20 mL) was stirred at room temperature for 0.5 hour, then tert-butyl 3-((dimethylamino)methylene)-4-oxopiperidine-1-carboxylate (3.10 g, 12.2 mmol) was added. The mixture was refluxed overnight. After the mixture was cooled down and concentrated, the residue was diluted with EtOAc (20 mL) and washed with brine (10 mL×3). The organic layer was dried over anhydrous sodium sulfate and concentrated. The residue was purified by chromatography on silica gel (EtOAc:Petroleum ether=2:1) to give an orange oil (750 mg, 25%). $^1$H NMR (400 MHz, CDCl$_3$) δ 8.05 (s, 1H), 4.95 (s, 2H), 4.44 (s, 2H), 3.69 (t, J=5.8 Hz, 2H), 2.75 (t, J=5.4 Hz, 2H), 1.49 (s, 9H).

Method J—Step c: 5,6,7,8-tetrahydropyrido[4,3-d]pyrimidin-2-amine

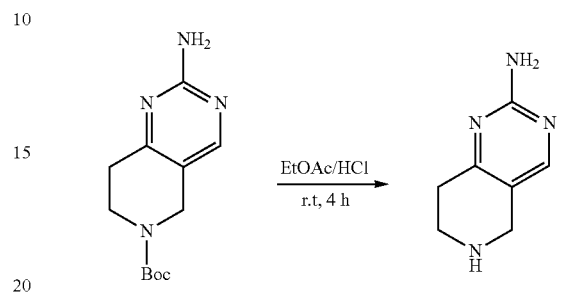

Tert-butyl 2-amino-7,8-dihydropyrido[4,3-d]pyrimidine-6(5H)-carboxylate (750 mg, 3.0 mmol) was added to 3M HCl/EtOAc (5 mL). The mixture was stirred at room temperature for 3 hours, then the solvent was removed by vacuum, and the residue was portioned between CH$_2$Cl$_2$ (20 mL) and saturated aqueous sodium bicarbonate (5 mL), the organic layer was separated, dried over anhydrous sodium sulfate and concentrated to give a white solid (350 mg, 78%).

Method J—Step d: 6-(5'-chloro-3,5-dimethyl-2,4'-bipyridin-2'-yl)-5,6,7,8-tetrahydropyrido[4,3-d]pyrimidin-2-amine

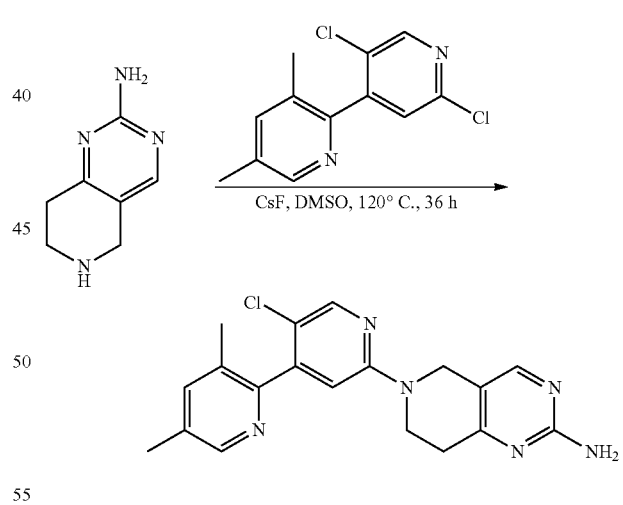

5,6,7,8-Tetrahydropyrido[4,3-d]pyrimidin-2-amine (50 mg, 0.3 mmol) was dissolved in DMSO (1 mL) followed by addition of CsF (125 mg, 0.8 mmol) and 4,5,6,7-tetrahydrothiazolo[5,4-c]pyridin-2-amine (127 mg, 0.5 mmol). The mixture was stirred at 120° C. for 36 hours, then portioned between EtOAc (20 mL) and water (10 mL), washed with brine (10 mL). The organic layer was dried over anhydrous sodium sulfate and concentrated under reduced pressure, purified by silica gel column chromatography (MeOH:CH$_2$Cl$_2$=1:50) to give a yellow solid (80 mg, 66%). $^1$H NMR (400 MHz, CDCl$_3$) δ 8.35 (s, 1H), 8.23 (s, 1H), 8.10 (s, 1H), 7.43 (s, 1H), 6.65 (s, 1H), 4.94 (s, 2H), 4.56 (s, 2H), 3.90 (t, J=5.8 Hz, 2H), 2.87 (t, J=5.8 Hz, 2H), 2.37 (s, 3H), 2.17 (s, 3H). ESI-MS (m/z): 367.1[M+1]+.

Method J—Step e: Ethyl6-(5'-chloro-3,5-dimethyl-2,4'-bipyridin-2'-yl)-5,6,7,8-tetrahydropyrido[4,3-d]pyrimidin-2-ylcarbamate

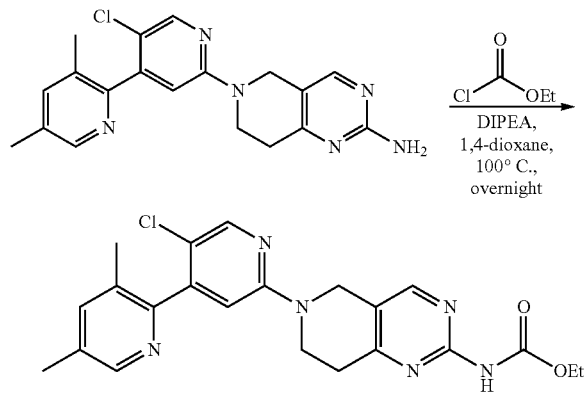

To a solution of 6-(5'-chloro-3,5-dimethyl-2,4'-bipyridin-2'-yl)-5,6,7,8-tetrahydropyrido[4,3-d]pyrimidin-2-amine (50 mg, 0.1 mmol) and DIPEA (53 mg, 0.4 mmol) in 1 mL of 1,4-dioxane was added ethyl carbonochloridate (18 mg, 0.2 mmol). The mixture was stirred at 100° C. overnight, then cooled down and added to 20 mL of CH$_2$Cl$_2$ and washed with brine (10 mL×3). The organic layer was dried over anhydrous sodium sulfate and concentrated. The residue was purified by silica gel column chromatography (EtOAc: Petroleum ether=1:1 to EtOAc) to give the title compound (20 mg, 33%) as a yellow solid. $^1$H NMR (400 MHz, CDCl$_3$) δ 8.40 (s, 1H), 8.35 (s, 1H), 8.24 (s, 1H), 7.60 (s, 1H), 7.43 (s, 1H), 6.68 (s, 1H), 4.66 (s, 2H), 4.27 (q, J=7.2 Hz, 2H), 3.93 (s, 2H), 3.02 (s, 2H), 2.38 (s, 3H), 2.17 (s, 3H), 1.32 (t, J=7.0 Hz, 3H). ESI-MS (m/z): 439.0[M+1]+.

Example 11

Preparation of 6-(5'-chloro-3,5-dimethyl-2,4'-bipyridin-2'-yl)-8-methyl-2-(pyrrolidin-1-yl)-5,6,7,8-tetrahydropyrido[4,3-d]pyrimidine (A-77)

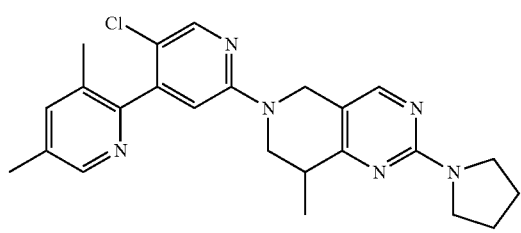 [SMILES: Cc1cnc(-c2cc(N3Cc4cnc(N5CCCC5)nc4C(C)C3)ncc2Cl)c(C)c1]

Method K—Step a: Tert-butyl 3-methyl-4-oxopiperidine-1-carboxylate

To a solution of tert-butyl 3-methyl-4-oxopiperidine-1-carboxylate (1.0 g, 5.00 mmol) in anhydrous THF (10 mL) was added LDA (3 mL, 6.0 mmol) dropwise at −78° C. under nitrogen atmosphere. After 30 minutes, MeI (852 mg, 6.0 mmol) was added to the above solution at the same temperature, then the mixture was stirred at room temperature for another 3 hours. The mixture was quenched with saturated NH$_4$Cl solution and was portioned between EtOAc (40 mL) and water (20 mL). The organic layer was washed with brine (10 mL), dried over sodium sulfate, and concentrated to give an orange oil. The residue was purified by silica gel column chromatography (petroleum ether:EtOAc=20:1) to afford the compound as a colorless oil (500 mg, 45%). $^1$H NMR (400 MHz, CDCl$_3$) δ 4.11 (m, 1H), 3.71 (m, 1H), 3.23 (m, 1H), 2.81 (br s, 1H), 2.47 (m, 3H), 1.47 (s, 9H), 1.03 (d, J=6.8 Hz, 3H).

Method K—Step b: Tert-butyl 8-methyl-2-(methylthio)-7,8-dihydropyrido[4,3-d]pyrimidine-6(5H)-carboxylate A solution of tert-butyl 4-oxopiperidine-1-carboxylate (0.94 mmol) was added into 1,1-dimethoxy-N,N-dimethylmethanamine (2 mL), the mixture was heated at 80° C. for 12 hours. The solution was cooled down and concentrated under reduced pressure to an orange oil for next step. 2-methylthiouronium sulfate (88 mg, 0.47 mmol) in 4 mL of EtOH was treated with sodium ethoxide (64 mg, 0.47 mmol). After 30 min, a solution of the orange oil above in EtOH (1 mL) was added, and the mixture was stirred at 80° C. for 12 hours. The reaction solution was cooled down to room temperature, concentrated under reduced pressure, and the residue was portioned between EtOAc (20 mL) and water (10 mL). The organic layer was washed with brine (10 mL), dried over sodium sulfate, and concentrated to give an orange oil. The residue was purified by silica gel column chromatography (petroleum ether:EtOAc=5:1) to afford the desired compound as an orange oil (100 mg, 36%). $^1$H NMR (400 MHz, CDCl₃) δ 8.25 (s, 1H), 3.75-3.70 (m, 3H), 3.49 (m, 1H), 2.94 (m, 1H), 2.56 (s, 3H), 1.41 (s, 9H), 1.26 (t, J=7.2 Hz, 3H).

Method K—Step c: Tert-butyl 8-methyl-2-(methylsulfonyl)-7,8-dihydropyrido[4,3-d]pyrimidine-6(5H)-carboxylate

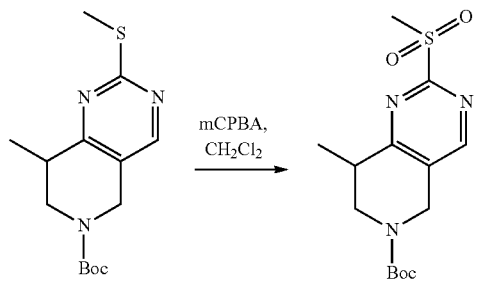 [SMILES: CSc1ncc2c(n1)C(C)CN(C(=O)OC(C)(C)C)C2 ; CC1CN(C(=O)OC(C)(C)C)Cc2cnc(S(C)(=O)=O)nc21]

To a solution of tert-butyl 8-methyl-2-(methylthio)-7,8-Dihydropyrido[4,3-d]pyrimidine-6(5H)-carboxylate (2.0 g, 6.8 mmol) in dichloromethane (20 mL) was added 3-chlorobenzoperoxoic acid (75%, 3.16 g, 13.6 mmol) slowly at 0° C. The mixture was stirred at room temperature for 12 hours. Then saturated NaHCO₃ solution (5 mL) and saturated Na₂S₂O₃ solution (5 mL) were added and stirred at room temperature for 30 minutes. The organic layer was separated and concentrated under reduced pressure. The residue was purified by silica gel column chromatography (petroleum ether:EtOAc=3:1) afforded a white solid (1.5 g, 67%).

Method K—Step d: Tert-butyl 8-methyl-2-(pyrrolidin-1-yl)-7,8-dihydropyrido[4,3-d]pyrimidine-6(5H)-carboxylate

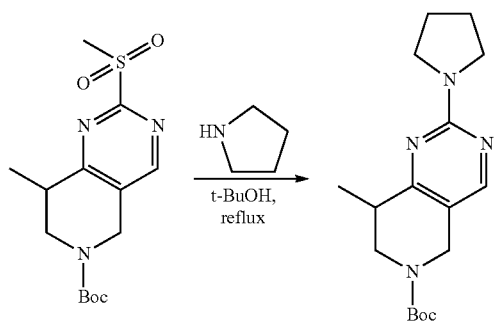 [SMILES: CC1CN(C(=O)OC(C)(C)C)Cc2cnc(S(C)(=O)=O)nc21 ; C1CCNC1 ; CC1CN(C(=O)OC(C)(C)C)Cc2cnc(N3CCCC3)nc21]

To a solution of tert-butyl 8-methyl-2-(methylsulfonyl)-7,8-dihydropyrido[4,3-d]pyrimidine-6(5H)-carboxylate (250 mg, 0.76 mmol) in t-butanol (2 mL) was added pyrrolidine (216 mg, 3.04 mmol), the mixture was heated to reflux for 12 hours. The reaction solution was cooled down and the solvent was removed by vacuum, the residue was purified by silica gel column chromatography (petroleum ether:EtOAc=4:1) afford a white solid (190 mg, 78%).

Method K—Step e: Tert-butyl 8-methyl-2-(pyrrolidin-1-yl)-7,8-dihydropyrido[4,3-d]pyrimidine-6(5H)-carboxylate

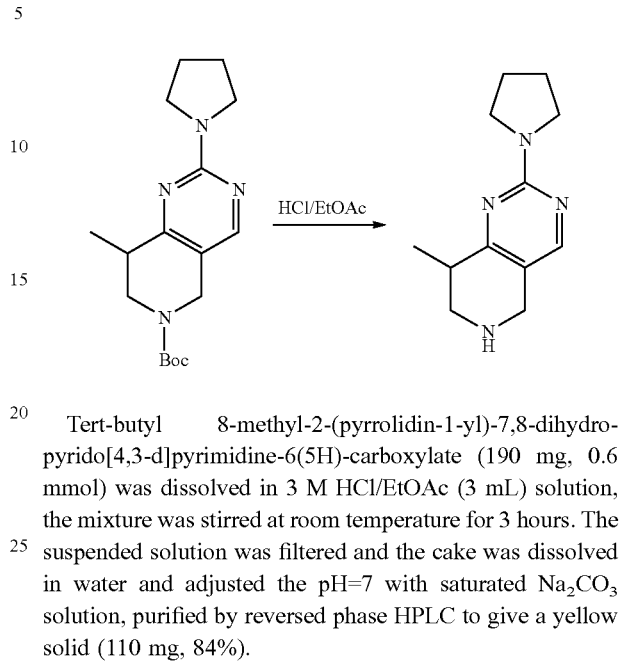

Tert-butyl 8-methyl-2-(pyrrolidin-1-yl)-7,8-dihydropyrido[4,3-d]pyrimidine-6(5H)-carboxylate (190 mg, 0.6 mmol) was dissolved in 3 M HCl/EtOAc (3 mL) solution, the mixture was stirred at room temperature for 3 hours. The suspended solution was filtered and the cake was dissolved in water and adjusted the pH=7 with saturated Na₂CO₃ solution, purified by reversed phase HPLC to give a yellow solid (110 mg, 84%).

Method K—Step f: 6-(5'-chloro-3,5-dimethyl-2,4'-bipyridin-2'-yl)-8-methyl-2-(pyrrolidin-1-yl)-5,6,7,8-tetrahydropyrido[4,3-d]pyrimidine

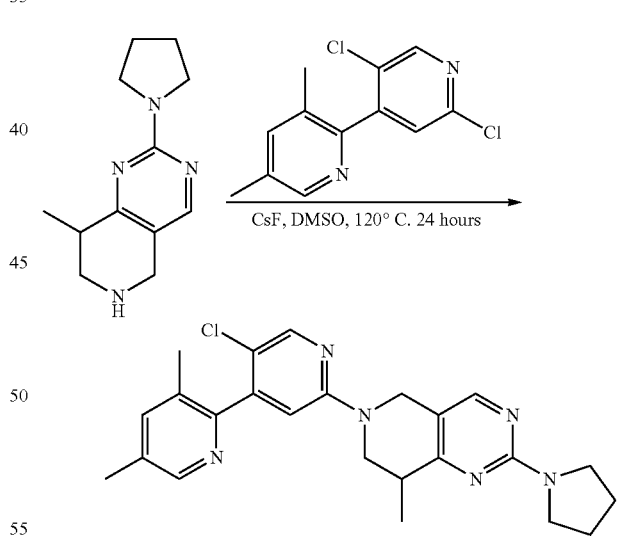

To a solution of 8-methyl-2-(pyrrolidin-1-yl)-5,6,7,8-tetrahydropyrido[4,3-d]pyrimidine (67 mg, 0.31 mmol), 2',5'-dichloro-3,5-dimethyl-2,4'-bipyridine (78 mg, 0.31 mmol) in dry dimethyl sulfoxide (1 mL) was added CsF (96 mg, 0.63 mmol), the suspended solution was heated 120° C. for 24 hours. Then the mixture was cooled down and portioned between EtOAc (10 mL) and water (5 mL), washed with brine (5 mL). The organic layer was concentrated under reduced pressure and purified by silica gel column chromatography (CH₂Cl₂:MeOH=1:100) to give a white solid (50 mg, 37%). ¹H NMR (400 MHz, CDCl₃) δ 8.39 (s, 1H), 8.26 (s, 1H), 8.15 (s, 1H), 7.46 (s, 1H), 6.66 (s, 1H), 4.54 (s, 2H), 4.02 (m, 1H), 3.61-3.58 (m, 5H), 3.05 (m, 1H), 2.41 (s, 3H), 2.11 (s, 3H), 2.01-1.99 (m, 4H), 1.37 (d, J=6.8 Hz, 3H). ESI-MS (m/z): 434.9[M+1]⁺.

Example 12

Preparation of N-(6-(5'-chloro-3,5-dimethyl-[2,4'-bipyridin]-2'-yl)-5-oxo-5,6,7,8-tetrahydropyrido[4,3-d]pyrimidin-2-yl)isobutyramide (A-108)

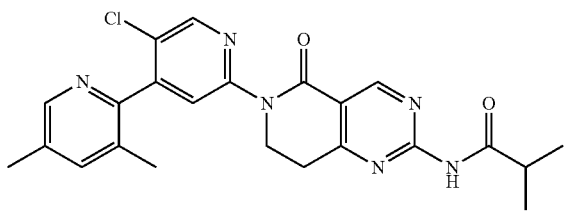 [SMILES: Cc1cnc(-c2cc(N3CCc4nc(NC(=O)C(C)C)ncc4C3=O)ncc2Cl)c(C)c1]

Method L—Step a: Tert-butyl 2-(methylthio)-5-oxo-7,8-dihydropyrido[4,3-d]pyrimidine-6(5H)-carboxylate

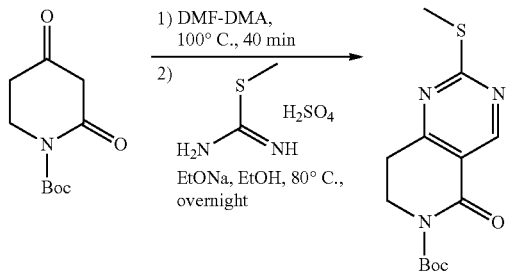

Tert-butyl 2,4-dioxopiperidine-1-carboxylate (2.45 g, 11.5 mmol) was dissolved in 10 mL of DMF-DMA. The mixture was stirred at 100° C. for 40 min. After cooling, the mixture was evaporated and added to the solution of 2-methyl-2-thiopeudourea sulfate (2.6 g, 13.8 mmol) and sodium ethanolate (1.88 g, 27.6 mmol) in 30 mL of ethanol. The reaction mixture was stirred at room temperature for 0.5 h and then heated to 80° C. overnight. After the mixture was evaporated, the residue was diluted with brine (30 mL) and extracted with ethyl acetate (30 mL×2). The combined organics were dried over Na₂SO₄ and concentrated to obtain the crude compound (2.5 g) as a brown oil that was used without further purification in the subsequent step. ¹H NMR (300 MHz, CDCl₃) δ 9.09 (s, 1H), 4.04 (t, J=6.4 Hz, 2H), 3.07 (t, J=6.4 Hz, 2H), 2.61 (s, 3H), 1.58 (s, 9H).

Method L—Step b: 2-(Methylthio)-7,8-dihydropyrido[4,3-d]pyrimidin-5(6H)-one

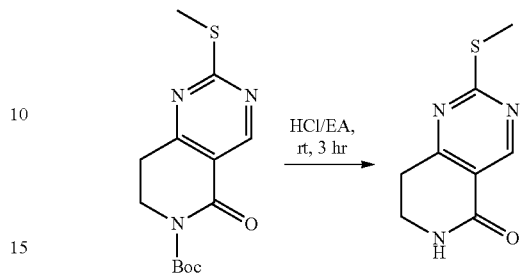

Tert-butyl 2-(methylthio)-5-oxo-7,8-dihydropyrido[4,3-d]pyrimidine-6(5H)-carboxylate (2.5 g, 8.47 mmol) was added to 3M HCl/EA (10 mL). The mixture was stirred at room temperature for 3 hours, then the product was filtered and washed with ethyl acetate (10 mL×2) and water (10 mL×2). Dried to give a yellow solid (1.4 g, 62.5% for two steps). ¹H NMR (300 MHz, CDCl₃) δ 9.01 (s, 1H), 5.99 (s, 1H), 3.65 (m, 2H), 3.08 (t, J=6.7 Hz, 2H), 2.61 (s, 3H).

Method L—Step c: 7-(5'-chloro-3,5-dimethyl-[2,4'-bipyridin]-2'-yl)-3-(methylthio)-6,7-dihydropyrido[4,3-d]pyrimidin-8 (5H)-one

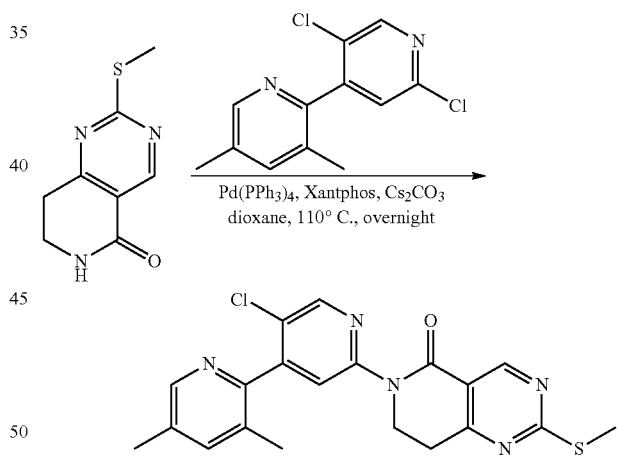

Pd(PPh₃)₄ (46 mg, 0.04 mmol), Xantphos (46 mg, 0.08 mmol), Cs₂CO₃ (489 mg, 1.5 mmol), 2-(pyrrolidin-1-yl)-6,7-dihydrothiazolo[5,4-c]pyridin-4(5H)-one (195 mg, 1 mmol) and 2',5'-dichloro-3,5-dimethyl-2,4'-bipyridine (303 mg, 1.2 mmol) were added to 15 mL of dioxane under nitrogen atmosphere. The mixture was stirred at 110° C. overnight. After cooling, the reaction mixture was filtered. The filtrate was evaporated and purified by silica gel column chromatography (petroleum ether:EtOAc=4:1) to give the title compound (257 mg, 62.3%) as a white solid. ¹H NMR (400 MHz, CDCl₃) δ 9.07 (s, 1H), 8.49 (s, 1H), 8.35 (s, 1H), 8.04 (s, 1H), 7.45 (s, 1H), 4.40 (t, J=6.4 Hz, 2H), 3.20 (t, J=6.4 Hz, 2H), 2.63 (s, 3H), 2.38 (s, 3H), 2.23 (s, 3H). ESI-MS (m/z): 411.8[M+1]⁺.

Method L—Step d: 7-(5'-chloro-3,5-dimethyl-[2,4'-bipyridin]-2'-yl)-3-(methylsulfinyl)-6,7-dihydropyrido[4,3-d]pyrimidin-8(5H)-one

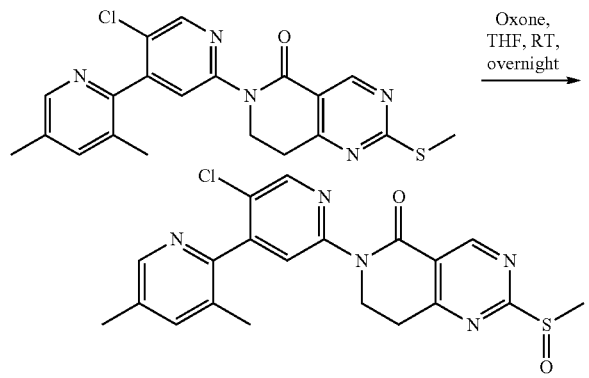

To a solution of 7-(5'-chloro-3,5-dimethyl-[2,4'-bipyridin]-2'-yl)-3-(methylthio)-6,7-dihydropyrido[4,3-d]pyrimidin-8(5H)-one (257 mg, 0.624 mmol) in 5 mL of THF was added the solution of oxone (287 mg, 0.935 mmol) in H$_2$O (1 mL) dropwise. The mixture was stirred at room temperature overnight and treated with brine (20 mL). The water layer was extracted with CH$_2$Cl$_2$ (20 mL×3). The combined organic layers were dried over Na$_2$SO$_4$ and concentrated to obtain the crude compound (240 mg) as a yellow solid that was used without further purification in the subsequent step.

Method L—Step e: 2-Amino-6-(5'-chloro-3,5-dimethyl-[2,4'-bipyridin]-2'-yl)-7,8-dihydropyrido[4,3-d]pyrimidin-5(6H)-one

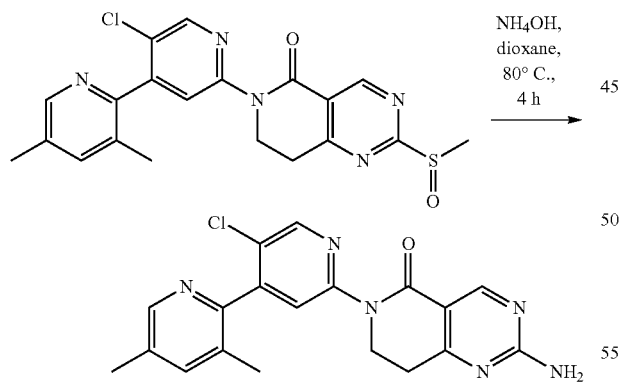

7-(5'-Chloro-3,5-dimethyl-[2,4'-bipyridin]-2'-yl)-3-(methylsulfinyl)-6,7-dihydropyrido[4,3-d]pyrimidin-8(5H)-one (360 mg, 0.843 mmol) and NH$_4$OH (28%, 9 mL) were added to 18 mL of dioxane. The mixture was stirred at 80° C. in a sealed tube for 4 hours. The mixture was evaporate and purified by silica gel column chromatography (petroleum ether:EtOAc=1:1) to give a yellow solid (100 mg, 31.1%). $^1$H NMR (400 MHz, CDCl$_3$) δ 8.94 (s, 1H), 8.50 (s, 1H), 8.37 (s, 1H), 8.03 (s, 1H), 7.47 (s, 1H), 5.57 (s, 2H), 4.37 (t, J=6.6 Hz, 2H), 3.07 (t, J=6.6 Hz, 2H), 2.40 (s, 3H), 2.25 (s, 3H).

Method L—Step f: N-(6-(5'-chloro-3,5-dimethyl-[2,4'-bipyridin]-2'-yl)-5-oxo-5,6,7,8-tetrahydropyrido[4,3-d]pyrimidin-2-yl)isobutyramide

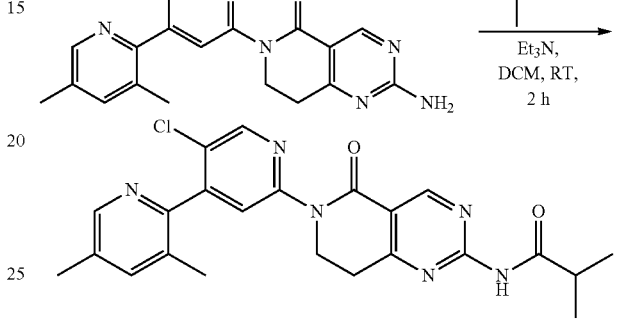

To a solution of 2-amino-6-(5'-chloro-3,5-dimethyl-[2,4'-bipyridin]-2'-yl)-7,8-dihydropyrido[4,3-d]pyrimidin-5(6H)-one (60 mg, 0.158 mmol) and Et$_3$N (96 mg, 0.948 mmol) in 10 mL of CH$_2$Cl$_2$ was added the solution of isobutyryl chloride (84 mg, 0.789 mmol) in 1 mL of CH$_2$Cl$_2$ dropwise. The mixture was stirred at room temperature for 2 hours. The reaction mixture was washed with brine (5 mL). The organic layer was dried over Na$_2$SO$_4$ and concentrated under reduced pressure, the residue was purified by column chromatography (petroleum ether:EtOAc=2:1) to give a white solid (17 mg, 23.9%). $^1$H NMR (400 MHz, CDCl$_3$) δ 9.17 (s, 1H), 8.71 (s, 1H), 8.49 (s, 1H), 8.35 (s, 1H), 8.05 (s, 1H), 7.46 (s, 1H), 4.40 (t, J=6.6 Hz, 2H), 3.24 (t, J=6.6 Hz, 2H), 3.06 (m, 1H), 2.38 (s, 3H), 2.23 (s, 3H), 1.28 (d, J=6.8 Hz, 6H). ESI-MS (m/z): 451.1[M+1]$^+$.

Example 13

Preparation of 7-(5'-chloro-3,5-dimethyl-[2,4'-bipyridin]-2'-yl)-3-(4-hydroxypiperidin-1-yl)-6,7-dihydropyrido[4,3-d]pyrimidin-8(5H)-one (A-97)

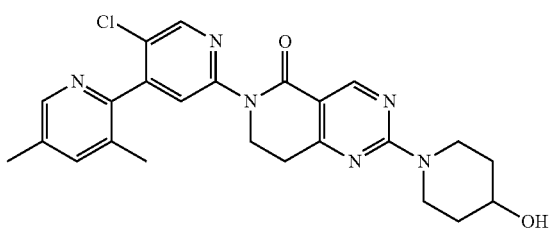 [SMILES: Cc1cnc(-c2cc(N3CCc4nc(N5CCC(O)CC5)ncc4C3=O)ncc2Cl)c(C)c1]

Method M—Step g: 7-(5'-chloro-3,5-dimethyl-[2,4'-bipyridin]-2'-yl)-3-(4-hydroxypiperidin-1-yl)-6,7-dihydropyrido[4,3-d]pyrimidin-8(5H)-one

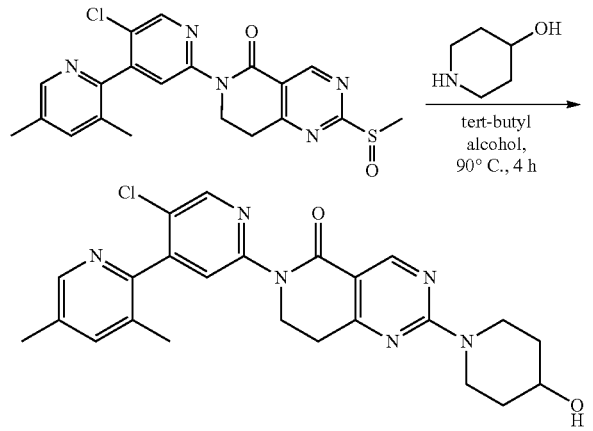

7-(5'-Chloro-3,5-dimethyl-[2,4'-bipyridin]-2'-yl)-3-(methylsulfinyl)-6,7-dihydropyrido[4,3-d]pyrimidin-8(5H)-one (50 mg, 0.117 mmol) and piperidin-4-ol (34 mg, 0.337 mmol) were dissolved in 1.5 mL of tert-butyl alcohol. The mixture was stirred at 90° C. for 4 hours. Evaporated and purified by silica gel column chromatography on silica gel (petroleum ether:EtOAc=1:1 to 1:2) to give the title compound (25 mg, 45.9%) as a white solid. $^1$H NMR (400 MHz, CDCl$_3$) δ 8.89 (s, 1H), 8.46 (s, 1H), 8.34 (s, 1H), 8.02 (s, 1H), 7.44 (s, 1H), 4.51-4.44 (m, 2H), 4.32 (t, J=6.6 Hz, 2H), 4.02 (m, 1H), 3.56-3.49 (m, 2H), 3.02 (t, J=6.2 Hz, 2H), 2.37 (s, 3H), 2.23 (s, 3H), 2.01-1.95 (m, 2H), 1.63-1.61 (m, 2H). ESI-MS (m/z): 464.8[M+1]$^+$.

Example 14

Preparation of 1-(6-(5'-chloro-3,5-dimethyl-2,4'-bipyridin-2'-yl)-5-methyl-5,6,7,8-tetrahydropyrido[4,3-d]pyrimidin-2-yl)pyrrolidin-3-ol (A-84)

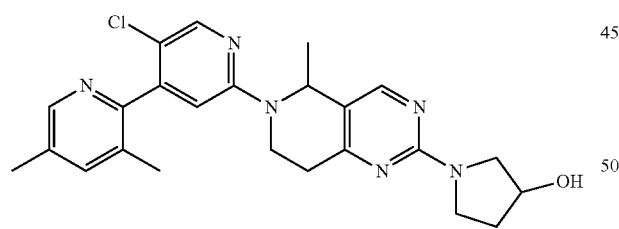

Method N—Step h: 1-(4-(2-(5'-chloro-3,5-dimethyl-2,4'-bipyridin-2'-ylamino)ethyl)-2-(methylthio)pyrimidin-5-yl)ethanone

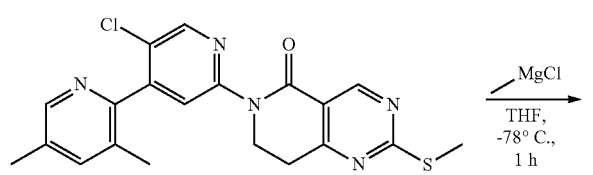

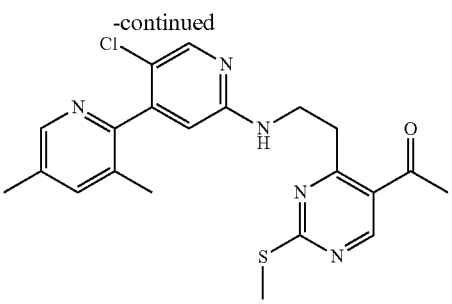

6-(5'-Chloro-3,5-dimethyl-2,4'-bipyridin-2'-yl)-2-(methylthio)-7,8-dihydropyrido[4,3-d]pyrimidin-5(6H)-one (500 mg, 1.21 mmol) was dissolved in anhydrous tetrahydrofuran (10 mL) followed by addition of methylmagnesium chloride (3 M in tetrahydrofuran, 1.62 mL, 4.86 mmol) at −78° C. under the nitrogen atmosphere. The mixture was stirred at −78° C. for 1 hour. Then the reaction was quenched with saturated aqueous NH$_4$Cl solution (1 mL), portioned between EtOAc and water. The organic layer was concentrated by vacuum and the residue was purified by silica gel column chromatography (Petroleum ether:EtOAc=3:1) to give a brown oil (550 mg, 96%). $^1$H NMR (400 MHz, CDCl$_3$) δ 8.82 (s, 1H), 8.32 (s, 1H), 8.08 (s, 1H), 7.40 (s, 1H), 6.34 (s, 1H), 5.29 (s, 1H), 3.75 (q, J=6.0 Hz, 2H), 3.35 (t, J=10.8 Hz, 2H), 2.57 (s, 3H), 2.36 (s, 3H), 2.16 (s, 3H). ESI-MS (m/z): 428.1[M+1]$^+$.

Method N—Step i: 6-(5'-Chloro-3,5-dimethyl-2,4'-bipyridin-2'-yl)-5-methyl-2-(methylthio)-5,6,7,8-tetrahydropyrido[4,3-d]pyrimidine

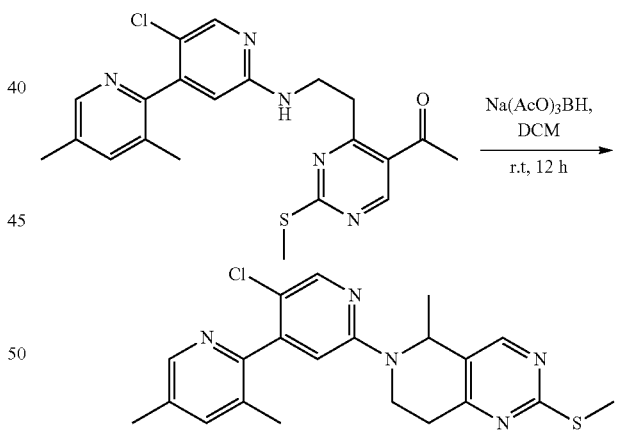

1-(4-(2-(5'-Chloro-3,5-dimethyl-2,4'-bipyridin-2'-ylamino)ethyl)-2-(methylthio)pyrimidin-5-yl)ethanone (500 mg, 1.17 mmol) was dissolved in anhydrous dichloromethane (10 mL) followed by addition of Na(OAc)$_3$BH (990 mg, 4.67 mmol) at room temperature. The mixture was stirred at same temperature for 12 hours. Then the mixture was quenched with saturated aqueous NH$_4$Cl solution, portioned between EtOAc and water. The organic layer was concentrated by vacuum and the residue was purified by silica gel column chromatography (Petroleum ether:EtOAc=3:1) to give a pale oil (400 mg, 83%). $^1$H NMR (400 MHz, CDCl$_3$) δ 8.35 (s, 1H), 8.32 (s, 1H), 8.22 (s, 1H), 7.43 (s, 1H), 6.63 (s, 1H), 5.58-5.49 (m, 1H), 4.41-4.33 (m, 1H), 3.47-3.38 (m, 1H), 3.05-2.99 (m, 1H), 2.98-2.86 (m, 1H), 2.56 (s, 3H), 2.37 (s, 3H), 2.18 (s, 3H), 1.46 (d, J=6.4 Hz, 3H). ESI-MS (m/z): 412.0[M+1]$^+$.

Method N—Step j: 6-(5'-chloro-3,5-dimethyl-2,4'-bipyridin-2'-yl)-5-methyl-2-(methylsulfonyl)-5,6,7,8-tetrahydropyrido[4,3-d]pyrimidine

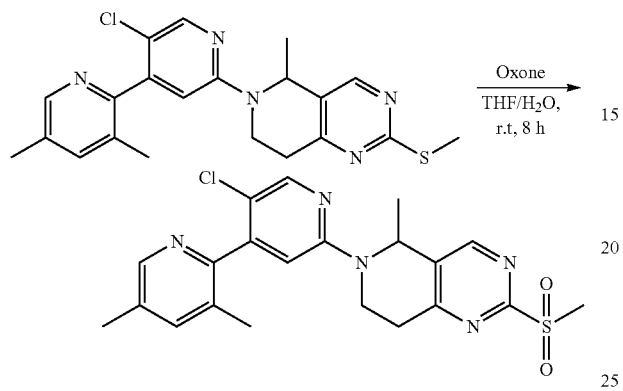

6-(5'-Chloro-3,5-dimethyl-2,4'-bipyridin-2'-yl)-5-methyl-2-(methylthio)-5,6,7,8-tetrahydropyrido[4,3-d]pyrimidine (400 mg, 0.97 mmol) was dissolved in THF/H$_2$O, followed by addition Oxone (660 mg, 2.15 mmol) at 0° C. The mixture was stirred at room temperature for 12 hours. Then the mixture was portioned between EtOAc and water, the organic was dried over anhydrous Na$_2$SO$_4$ and concentrated to give a pale yellow solid without further purification for next step (270 mg).

Method N—Step k: 1-(6-(5'-Chloro-3,5-dimethyl-2,4'-bipyridin-2'-yl)-5-methyl-5,6,7,8-tetrahydropyrido[4,3-d]pyrimidin-2-yl)pyrrolidin-3-ol

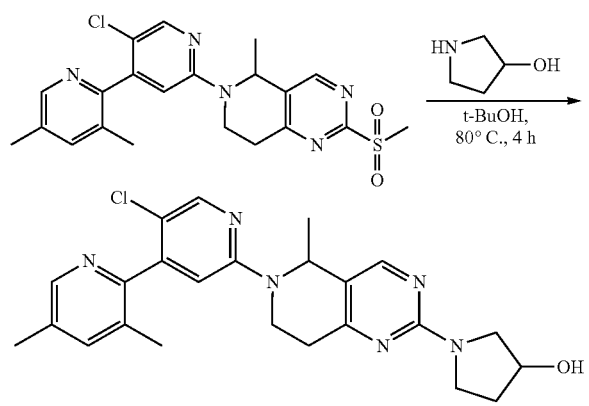

6-(5'-Chloro-3,5-dimethyl-2,4'-bipyridin-2'-yl)-5-methyl-2-(methylsulfonyl)-5,6,7,8-tetrahydropyrido[4,3-d]pyrimidine (40 mg, 0.090 mmol) was dissolved in tert-butanol (1 mL) followed by addition of pyrrolidin-3-ol (40 mg, 0.56 mmol). The mixture was stirred at 80° C. for 4 hours. Then the mixture was portioned between ethyl acetate and water. The organic layer was dried over anhydrous Na$_2$SO$_4$, concentrated, and the residue was purified by column chromatography (MeOH:CH$_2$Cl$_2$=1:50) to give a white solid (12 mg, 29%). $^1$H NMR (400 MHz, CDCl$_3$) δ 8.35 (s, 1H), 8.21 (s, 1H), 8.13 (s, 1H), 7.42 (s, 1H), 6.61 (s, 1H), 5.40-5.33 (m, 1H), 4.63-4.56 (m, 1H), 4.38-4.31 (m, 1H), 3.77-3.63 (m, 4H), 3.46-3.35 (m, 1H), 2.98-2.86 (m, 1H), 2.82-2.73 (m, 1H), 2.37 (s, 3H), 2.18 (s, 3H), 2.15-2.01 (m, 2H), 1.42 (d, J=6.4 Hz, 3H). ESI-MS (m/z): 451.3[M−1]$^+$.

Example 15

Preparation of 6-(5'-chloro-3-methyl-2,4'-bipyridin-2'-yl)-N-cyclopropyl-5,6,7,8-tetrahydropyrido[4,3-d]pyrimidin-2-amine (A-111)

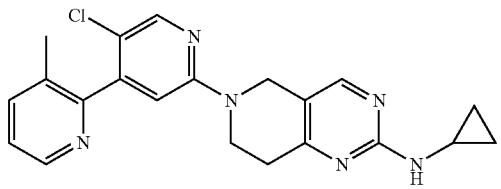 [SMILES: Cc1cccnc1-c1cc(N2CCc3nc(NC4CC4)ncc3C2)ncc1Cl]

Method O—Step a: 2',5'-dichloro-3-methyl-2,4'-bipyridine

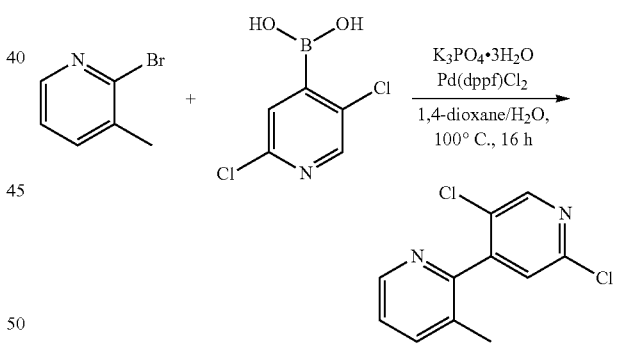

A 25 mL flask which is charged with 2-bromo-3-methylpyridine (500 mg, 2.82 mmol), A1-8 (700 mg, 3.64 mmol), K$_3$PO$_4$.3H$_2$O (1.50 g, 5.64 mmol), Pd(dppf)Cl$_2$ (103 mg, 0.140 mmol) in 1,4-dioxane/H$_2$O (7:1, 10 mL) is evacuated and backfilled with N$_2$ three times. Then the reaction was carried out at 100° C. for 16 hours. The mixture was cooled down and filtered, the filtrate was concentrated and the residue was purified by silica gel column chromatography (Petroleum ether:EtOAc=20:1) to give a white solid (40 mg, 6%). $^1$H NMR (400 MHz, CDCl$_3$) δ 8.55 (d, J=4.4 Hz, 1H), 8.48 (s, 1H), 7.65 (d, J=7.6 Hz, 1H), 7.34 (s, 1H), 7.33-7.31 (m, 1H), 2.20 (s, 3H).

Method O—Step b: 6-(5'-chloro-3-methyl-2,4'-bipyridin-2'-yl)-N-cyclopropyl-5,6,7,8-tetrahydropyrido[4,3-d]pyrimidin-2-amine

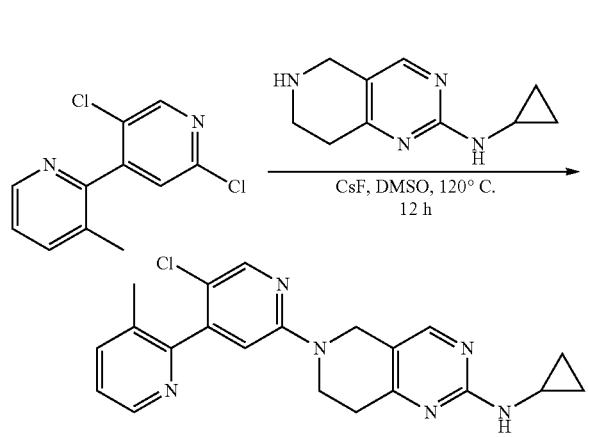

2',5'-Dichloro-3-methyl-2,4'-bipyridine (40 mg, 0.17 mmol) was dissolved in anhydrous DMSO (1 mL) following with N-cyclopropyl-5,6,7,8-tetrahydropyrido[4,3-d]pyrimidin-2-amine (50 mg, 0.26 mmol) and C$_s$F (64 mg, 0.43 mmol). The reaction was stirred at 120° C. for 12 hours. Then the mixture was portioned between EtOAc and water, the organic layer was concentrate and the residue was purified by silica gel column chromatography (Petroleum ether:EtOAc=1:1) to give a yellow solid (2 mg, 3%). $^1$H NMR (400 MHz, CDCl$_3$) δ 8.53 (d, J=4.4 Hz, 1H), 8.25 (s, 1H), 8.17 (s, 1H), 7.62 (d, J=7.6 Hz, 1H), 7.29-7.28 (m, 1H), 5.28 (s, 1H), 4.56 (s, 2H), 3.99-3.83 (m, 2H), 2.89 (t, J=11.2 Hz, 2H), 2.83-2.73 (m, 1H), 2.21 (s, 3H), 0.85-0.78 (m, 2H), 0.59-0.48 (m, 2H). ESI-MS (m/z): 392.9[M+1]$^+$.

Example 16

Preparation of 6-(5-chloro-4-(pyrimidin-2-yl)pyridin-2-yl)-N-cyclopropyl-5,6,7,8-tetrahydropyrido[4,3-d]pyrimidin-2-amine (A-115)

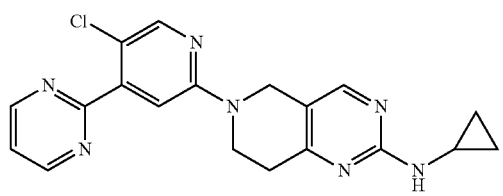

Method P—Step a:
2-(2,5-Dichloropyridin-4-yl)pyrimidine

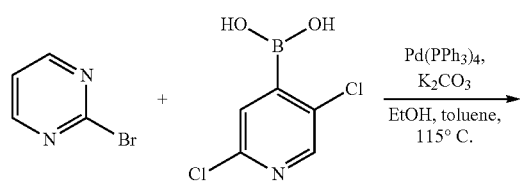

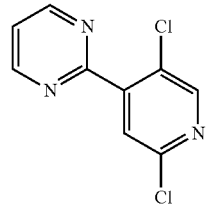

A 25 mL flask which is charged with 2-bromopyrimidine (200 mg, 1.26 mmol), 2,5-dichloropyridin-4-ylboronic acid (290 mg, 1.5 mmol), 2M K$_2$CO$_3$ solution (2 mL), Pd(PPh$_3$)$_4$ (146 mg, 0.13 mmol) in the solution of toluene/EtOH (1:1, 6 mL) is evacuated and backfilled with N$_2$ three times. the reaction was stirred at 115° C. for 16 hours. Then the mixture was cooled down and filtered, the filtrate was concentrated and the residue was purified by silica gel column chromatography (Petroleum ether:EtOAc=25:1) to give a white solid (60 mg, 21%). $^1$H NMR (400 MHz, CDCl$_3$): δ 8.86 (d, J=4.8 Hz, 2H), 8.45 (s, 1H), 7.73 (s, 1H), 7.33 (t, J=4.8 Hz, 1H).

Method P—Step b: 6-(5-Chloro-4-(pyrimidin-2-yl)pyridin-2-yl)-N-cyclopropyl-5,6,7,8-tetrahydropyrido[4,3-d]pyrimidin-2-amine

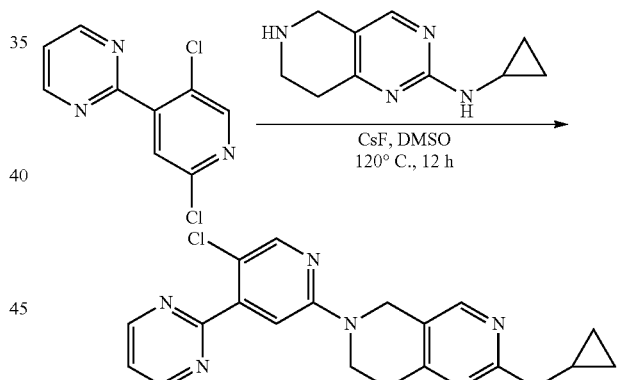

2-(2,5-Dichloropyridin-4-yl)pyrimidine (20 mg, 0.09 mmol) was dissolved in anhydrous DMSO (1 mL) following with N-cyclopropyl-5,6,7,8-tetrahydropyrido[4,3-d]pyrimidin-2-amine (17 mg, 0.09 mmol) and C$_s$F (27 mg, 0.18 mmol). The reaction was stirred at 120° C. for 12 h. Then the mixture was portioned between EtOAc and water, the organic layer was concentrate and the residue was purified by column chromatography (CH$_2$Cl$_2$:MeOH=100:1), to give a yellow solid (7 mg, 20%). $^1$H NMR (400 MHz, CDCl$_3$) δ 8.97 (d, J=4.8 Hz, 2H), 8.31 (s, 1H), 8.20 (s, 1H), 7.37 (t, J=4.8 Hz, 1H), 7.08 (s, 1H), 5.29 (br s, 1H), 4.59 (s, 2H), 3.94 (t, J=6.0 Hz, 2H), 2.90 (t, J=5.6 Hz, 2H), 2.77 (br s, 1H), 0.84-0.80 (m, 2H), 0.54 (s, 2H). ESI-MS (m/z): 380.1 [M+1]$^+$.

Example 17

Preparation of 6-(5-chloro-4-(pyrazin-2-yl)pyridin-2-yl)-N-cyclopropyl-5,6,7,8-tetrahydropyrido[4,3-d]pyrimidin-2-amine (A-116)

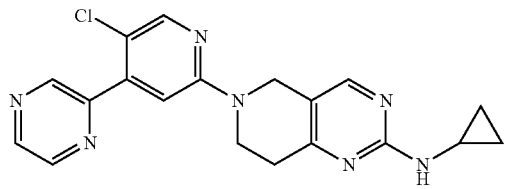 [SMILES: Clc1cnc(N2CCc3nc(NC4CC4)ncc3C2)cc1-c1cnccn1]

Method Q—Step a:
2-(2,5-Dichloropyridin-4-yl)pyrazine

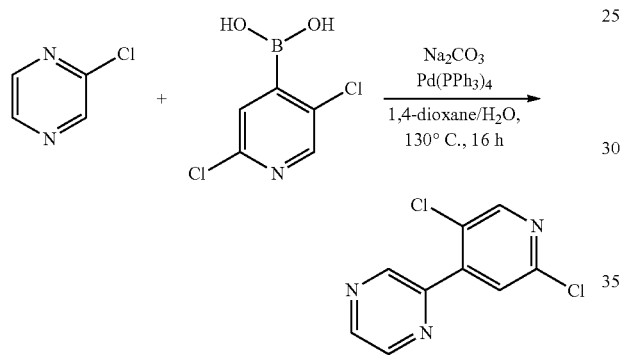

A 25 mL sealed tube which is charged with 2-chloropyrazine (100 mg, 0.87 mmol), A1-8 (340 mg, 1.77 mmol), Na$_2$CO$_3$ (185 mg, 1.74 mmol), Pd(PPh$_3$)$_4$ (170 mg, 0.15 mmol) in 1,4-dioxane/H$_2$O (7:1, 5 mL) is bubbled with N$_2$ 10 minutes. The reaction was carried out at 130° C. for 16 h. Then it was cooled down and filtered, the filtrate was concentrated and the residue was purified by column chromatography (Petroleum ether:CH$_2$Cl$_2$=3:2) to give a white solid (35 mg, 18%). $^1$H NMR (400 MHz, CDCl$_3$) δ 9.09 (s, 1H), 8.78-8.75 (m, 1H), 8.70 (d, J=2.4 Hz, 1H), 8.54 (s, 1H), 7.69 (s, 1H).

Method Q—Step b: 6-(5-Chloro-4-(pyrazin-2-yl)pyridin-2-yl)-N-cyclopropyl-5,6,7,8-tetrahydropyrido[4,3-d]pyrimidin-2-amine

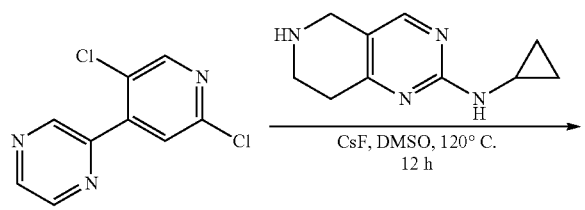

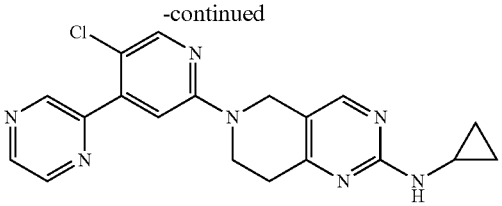

2-(2,5-Dichloropyridin-4-yl)pyrazine (35 mg, 0.15 mmol) was dissolved in anhydrous DMSO (1 mL) following with N-cyclopropyl-5,6,7,8-tetrahydropyrido[4,3-d]pyrimidin-2-amine (40 mg, 0.21 mmol) and C$_s$F (70 mg, 0.47 mmol). The reaction was stirred at 120° C. for 12 hours. Then the mixture was portioned between EtOAc and water, the organic layer was concentrated and the residue was purified by silica gel column chromatography (Petroleum ether:EtOAc=1:1) to give a yellow solid (10 mg, 17%). $^1$H NMR (400 MHz, CDCl$_3$) δ 9.02 (s, 1H), 8.30 (s, 1H), 8.22 (s, 1H), 8.05 (d, J=8.0 Hz, 1H), 7.88 (d, J=8.0 Hz, 1H), 6.98 (s, 1H), 5.88 (br s, 1H), 4.62 (s, 2H), 3.95 (t, J=11.2 Hz, 2H), 296 (t, J=11.2 Hz, 2H), 2.83-2.77 (m, 1H), 0.87-0.83 (m, 2H), 0.60-0.56 (m, 2H). ESI-MS (m/z): 379.9[M+1]$^+$.

Example 18

Preparation of Preparation of 6-(5-chloro-4-(thiazol-2-yl)pyridin-2-yl)-N-cyclopropyl-5,6,7,8-tetrahydropyrido[4,3-d]pyrimidin-2-amine (A-117)

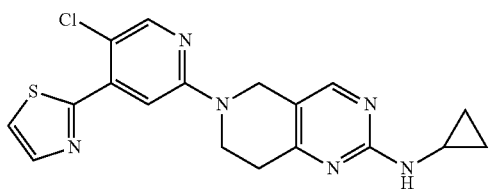 [SMILES: Clc1cnc(N2CCc3nc(NC4CC4)ncc3C2)cc1-c1nccs1]

Method R—Step a:
2-(2,5-Dichloropyridin-4-yl)thiazole

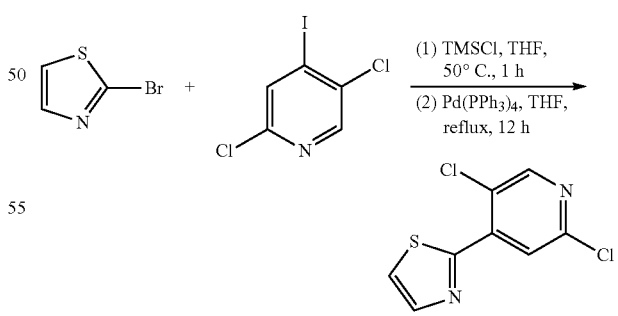

1,2-Diromobutane (40 mg, 0.21 mmol) was added to a suspension of zinc powder (300 mg, 4.61 mmol) in THF (2 mL). The mixture was heated to 50° C. for 5 minutes and then TMSCl (20 mg, 0.18 mmol) was added. Meanwhile, a solution of 2-bromothiazole (200 mg, 1.22 mmol) in THF (1 mL) was added dropwise, and the mixture was stirred at 50° C. for 1 hour. After that, the solution of 2-thiazolyzinc bromide was injected into a solution of 2,5-dichloro-4-iodopyridine (300 mg, 1.09 mmol) and Pd(PPh$_3$)$_4$ (40 mg, 0.034 mmol) in THF (10 mL). The reaction was carried out at reflux for 12 hours under the nitrogen atmosphere. After that, the mixture was filtered and the filtrate was concentrated and the residue was purified by silica gel column chromatography (Petroleum ether:CH$_2$Cl$_2$=3:2), to give a white solid (60 mg, 24%). $^1$H NMR (300 MHz, CDCl$_3$) δ 8.53 (s, 1H), 8.51 (s, 1H), 8.08-8.07 (m, 1H), 7.68-7.67 (m, 1H).

Method R—Step b: 6-(5-Chloro-4-(thiazol-2-yl)pyridin-2-yl)-N-cyclopropyl-5,6,7,8-tetrahydropyrido[4,3-d]pyrimidin-2-amine

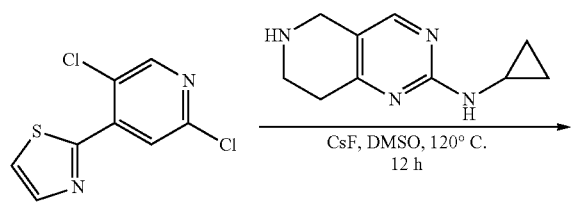

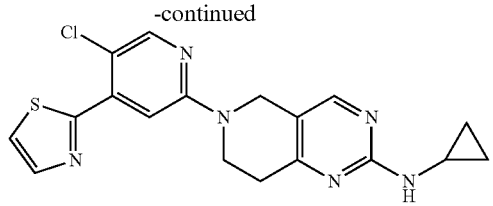

2-(2,5-Dichloropyridin-4-yl)thiazole (50 mg, 0.22 mmol) was dissolved in anhydrous DMSO (1 mL) following with N-cyclopropyl-5,6,7,8-tetrahydropyrido[4,3-d]pyrimidin-2-amine (50 mg, 0.26 mmol) and C$_s$F (130 mg, 0.85 mmol). The reaction was stirred at 120° C. for 12 hours. Then the mixture was portioned between EtOAc and water, the organic layer was concentrate and the residue was purified by silica gel column chromatography (Petroleum ether: EtOAc=1:1) to give a yellow solid (8 mg, 10%). $^1$H NMR (300 MHz, CDCl$_3$) δ 8.31 (s, 1H), 8.24 (s, 1H), 8.02 (d, J=3.0 Hz, 1H), 7.62 (s, 1H), 7.61 (d, J=3 Hz, 1H), 5.70 (br s, 1H), 4.63 (s, 2H), 3.98 (t, J=11.2 Hz, 2H), 2.99-2.93 (m, 2H), 2.83-2.75 (m, 1H), 0.87-0.81 (m, 2H), 0.61-0.50 (m, 2H). ESI-MS (m/z): 384.8[M+1]$^+$.

Table 1 shows a selection of the compounds prepared according to the methods discussed above in detail and indicated in the fourth column of the table:

TABLE 1

Selected compounds (A-1 to A-118) of the present invention.

| Example number | structure | Compound Name | Method | MS m/z (m + 1) | 1H NMR |
|---|---|---|---|---|---|
| A-1 | 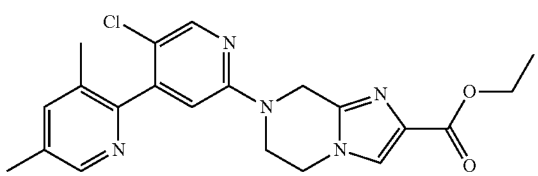 [SMILES: CCOC(=O)c1cn2c(n1)CN(c1cc(-c3ncc(C)cc3C)c(Cl)cn1)CC2] | ethyl 7-(5'-chloro-3,5-dimethyl-2,4'-bipyridin-2'-yl)-5,6,7,8-tetrahydroimidazo[1,2-a]pyrazine-2-carboxylate | C | 411.8 | $^1$H NMR (400 MHz, CDCl$_3$) δ 8.37 (s, 1H), 8.26 (s, 1H), 7.58 (s, 1H), 7.47 (s, 1H), 6.65 (s, 1H), 4.75 (s, 2H), 4.36 (q, J = 7.2 Hz, 2H), 4.34 (br s, 4H), 2.62 (s, 3H), 2.20 (s, 3H), 1.39 (t, J = 7.1 Hz, 7H) |
| A-2 | 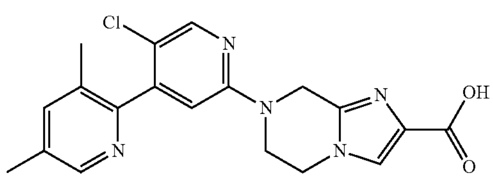 [SMILES: Cc1cnc(-c2cc(N3CCn4cc(C(=O)O)nc4C3)ncc2Cl)c(C)c1] | 7-(5'-chloro-3,5-dimethyl-2,4'-bipyridin-2'-yl)-5,6,7,8-tetrahydroimidazo[1,2-a]pyrazine-2-carboxylic acid | C | 383.8 | $^1$H NMR (400 MHz, CDCl$_3$): δ 8.40 (s, 1H), 8.21 (s, 1H), 7.49 (s, 1H), 7.44 (s, 1H), 6.68 (s, 1H), 4.69 (s, 2H), 4.11 (br, 4H), 2.37 (s, 3H), 2.17 (s, 3H) |
| A-3 | 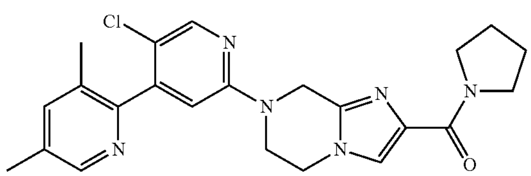 [SMILES: Cc1cnc(-c2cc(N3CCn4cc(C(=O)N5CCCC5)nc4C3)ncc2Cl)c(C)c1] | (7-(5'-chloro-3,5-dimethyl-2,4'-bipyridin-2'-yl)-5,6,7,8-tetrahydroimidazo[1,2-a]pyrazin-2-yl)(pyrrolidin-1-yl)methanone | C | 436.8 | $^1$H NMR (400 MHz, CDCl$_3$): δ 8.36 (s, 1H), 8.24 (s, 1H), 7.53 (s, 1H), 7.44 (s, 1H), 6.68 (s, 1H), 4.72 (s, 2H), 4.15 (br, 4H), 3.95 (t, J = 6.4 Hz, 2H), 3.63 (t, J = 6.4 Hz, 2H), 2.39 (s, 3H), 2.18 (s, 3H) 1.93-1.87 (m, 4H) |

TABLE 1-continued

Selected compounds (A-1 to A-118) of the present invention.

| Example number | structure | Compound Name | Method | MS m/z (m + 1) | 1H NMR |
|---|---|---|---|---|---|
| A-4 | 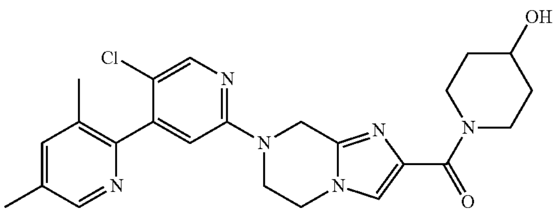 [SMILES: Cc1cnc(-c2cc(N3CCn4cc(C(=O)N5CCC(O)CC5)nc4C3)ncc2Cl)c(C)c1] | (7-(5'-chloro-3,5-dimethyl-2,4'-bipyridin-2'-yl)-5,6,7,8-tetrahydro-imidazo-[1,2-a]pyrazin-2-yl)(4-hydroxy-piperidin-1-yl)methanone | C | 466.8 | $^1$H NMR (400 MHz, CDCl$_3$): δ 8.34 (s, 1 H), 8.24 (s, 1 H), 7.52 (s, 1 H), 7.44 (s, 1H), 6.63 (s, 1H), 4.63 (s, 2H), 4.14 (br, 4H), 3.91 (m, 1H), 3.60 (br, 1H), 3.25 (br, 1H), 2.38 (s, 3H), 2.17 (s, 3H) 1.93 (m, 2H), 1.56 (m, 2H) |
| A-5 | 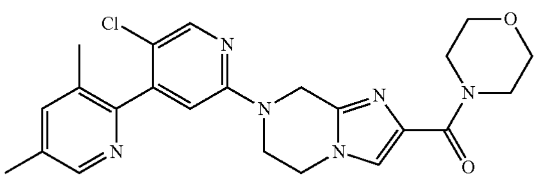 [SMILES: Cc1cnc(-c2cc(N3CCn4cc(C(=O)N5CCOCC5)nc4C3)ncc2Cl)c(C)c1] | (7-(5'-chloro-3,5-dimethyl-2,4'-bipyridin-2'-yl)-5,6,7,8-tetrahydro-imidazo-[1,2-a]pyrazin-2-yl)(morpholino)methanone | C | 452.8 | $^1$H NMR (400 MHz, CDCl$_3$): δ 8.41 (s, 1H), 8.30 (s, 1H), 7.53 (s, 2H), 6.76 (s, 1H), 4.81 (s, 2H), 4.21 (s, 4H), 3.80 (m, 8H), 2.46 (s, 3H), 2.25 (s, 3H) |
| A-6 | 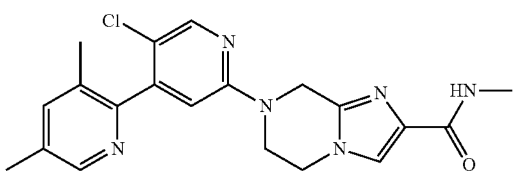 | 7-(5'-chloro-3,5-dimethyl-2,4'-bipyridin-2'-yl)-N-methyl-5,6,7,8-tetrahydro-imidazo-[1,2-a]pyrazine-2-carboxamide | C | 396.8 | $^1$H NMR (400 MHz, CDCl$_3$): δ 8.41 (s, 1H), 8.28 (s, 1H), 7.64 (br s, 1H), 7.54 (s, 1H), 6.74 (s, 1H), 4.89-4.69 (m, 2H), 4.20 (s, 4H), 2.95 (s, 3H), 2.45 (s, 3H), 2.23 (s, 3H) |
| A-7 | 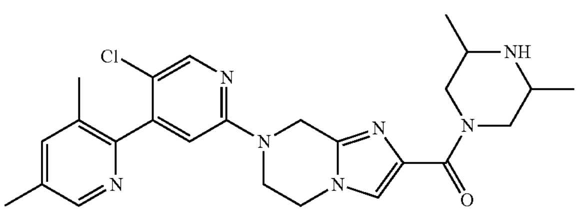 | (7-(5'-chloro-3,5-dimethyl-2,4'-bipyridin-2'-yl)-5,6,7,8-tetrahydro-imidazo-[1,2-a]pyrazin-2-yl)(3,5-dimethyl-piperazin-1-yl)methanone | C | 479.8 | $^1$H NMR (400 MHz, CDCl$_3$): δ 8.32 (s, 1H), 8.30 (s, 1H), 7.72 (s, 1H), 7.60 (s, 1H), 7.02 (s, 1H), 4.77 (s, 2H), 4.12 (d, J = 4.8 Hz, 2H), 4.07 (d, J = 4.0 Hz, 2H), 2.34 (s, 3H), 2.09 (s, 3H), 1.21 (s, 6H) |
| A-8 | 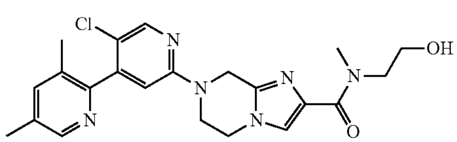 [SMILES: Cc1cnc(-c2cc(N3CCn4cc(C(=O)N(C)CCO)nc4C3)ncc2Cl)c(C)c1] | 7-(5'-chloro-3,5-dimethyl-2,4'-bipyridin-2'-yl)-N-(2-hydroxyethyl)-N-methyl-5,6,7,8-tetrahydro-imidazo-[1,2-a]pyrazine-2-carboxamide | C | 440.8 | $^1$H NMR (400 MHz, CDCl$_3$) δ 8.33-8.30 (m, 1H), 8.29 (s, 1H), 7.59 (s, 2H), 7.07 (s, 1H), 4.77 (s, 2H), 4.14-4.03 (m, 4H), 3.80 (br s, 1H), 3.63-3.49 (m, 4H), 2.99-2.87 (m, 2H), 2.33 (s, 3H), 2.09 (s, 3H) |

TABLE 1-continued

Selected compounds (A-1 to A-118) of the present invention.

| Example number | structure | Compound Name | Method | MS m/z (m + 1) | 1H NMR |
|---|---|---|---|---|---|
| A-9 | 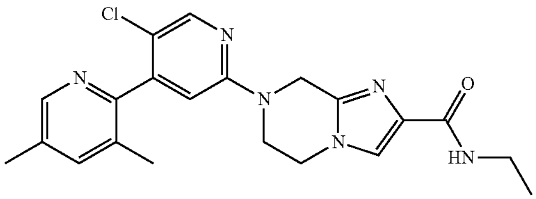 [SMILES: CCNC(=O)c1cn2c(n1)CN(c1cc(-c3ncc(C)cc3C)c(Cl)cn1)CC2] | 7-(5'-chloro-3,5-dimethyl-2,4'-bipyridin-2'-yl)-N-ethyl-5,6,7,8-tetrahydroimidazo-[1,2-a]pyrazine-2-carboxamide | C | 410.8 | ¹H NMR (400 MHz, CDCl₃) δ 8.29 (s, 1H), 8.18 (s, 1H), 7.44 (s, 1H), 7.39 (s, 1H), 7.00 (s, 1H), 6.60 (s, 1H), 4.64 (s, 2H), 4.07 (s, 4H), 3.37 (t, J = 6.4 Hz, 2H), 2.32 (s, 3H), 2.10 (s, 3H), 1.14 (t, J = 6.8 Hz, 3H) |
| A-10 | 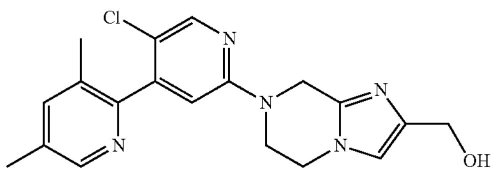 [SMILES: Cc1cnc(-c2cc(N3CCn4cc(CO)nc4C3)ncc2Cl)c(C)c1] | (7-(5'-chloro-3,5-dimethyl-2,4'-bipyridin-2'-yl)-5,6,7,8-tetrahydroimidazo-[1,2-a]pyrazin-2-yl)methanol | A | 370.1 | ¹H NMR (400 MHz, CDCl₃) δ 8.35 (s, 1H), 8.24 (s, 1H), 7.44 (s, 1H), 6.84 (s, 1H), 6.65 (s, 1H), 4.70 (s, 2H), 4.58 (s, 2H), 4.15 (s, 2H), 4.09 (d, J = 4.0 Hz, 2H), 2.38 (s, 3H), 2.16 (s, 3H) |
| A-11 | 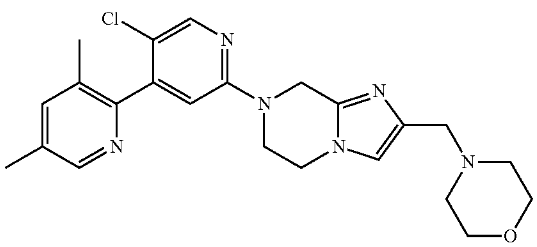 [SMILES: Cc1cnc(-c2cc(N3CCn4cc(CN5CCOCC5)nc4C3)ncc2Cl)c(C)c1] | 4-((7-(5'-chloro-3,5-dimethyl-2,4'-bipyridin-2'-yl)-5,6,7,8-tetrahydroimidazo-[1,2-a]pyrazin-2-yl)methyl)-morpholine | B | 438.8 | ¹H NMR (400 MHz, CDCl₃) δ 8.34 (s, 1H), 8.24 (s, 1H), 7.43 (s, 1H), 7.00 (s, 1H), 6.63 (s, 1H), 4.68 (s, 2H), 4.14 (s, 2H), 4.08 (s, 2H), 3.83 (s, 4H), 3.66 (s, 2H), 2.73 (s, 4H), 2.38 (s, 3H), 2.16 (s, 3H) |
| A-12 | 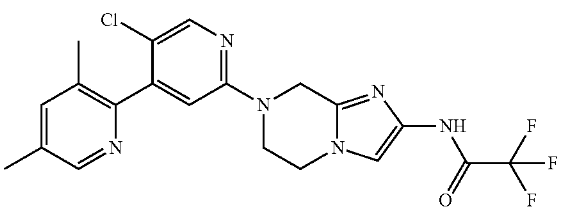 [SMILES: Cc1cnc(-c2cc(N3CCn4cc(NC(=O)C(F)(F)F)nc4C3)ncc2Cl)c(C)c1] | N-(7-(5'-chloro-3,5-dimethyl-2,4'-bipyridin-2'-yl)-5,6,7,8-tetrahydroimidazo-[1,2-a]pyrazin-2-yl)-2,2,2-trifluoroacetamide | D | 450.7 | ¹H NMR (400 MHz, CDCl₃) δ 10.76 (s, 1H), 8.34 (s, 1H), 8.25 (d, J = 2.8Hz, 1H), 7.43 (s, 1H), 7.36 (d, J = 2.4 Hz, 1H), 6.64 (s, 1H), 4.63 (s, 2H), 4.11 (s, 4H), 2.37 (s, 3H), 2.16 (s, 3H) |
| A-13 | 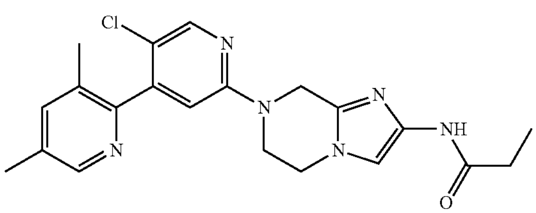 [SMILES: CCC(=O)Nc1cn2c(n1)CN(c1cc(-c3ncc(C)cc3C)c(Cl)cn1)CC2] | N-(7-(5'-chloro-3,5-dimethyl-2,4'-bipyridin-2'-yl)-5,6,7,8-tetrahydroimidazo-[1,2-a]pyrazin-2-yl)propionamide | E | 410.9 | ¹H NMR (400 MHz, CDCl₃) δ 8.35 (s, 1H), 8.25 (s, 1H), 8.22 (s,1H), 7.44 (s, 1H), 7.25 (s, 1H), 6.65 (s, 1H), 4.63 (s, 2H), 4.12 (s, 2H), 4.07 (d, J = 4.0 Hz, 2H), 2.38-2.35 (m, 5H), 2.17 (s, 3H), 1.22 (t, J = 7.8 Hz, 3H) |
| A-14 | 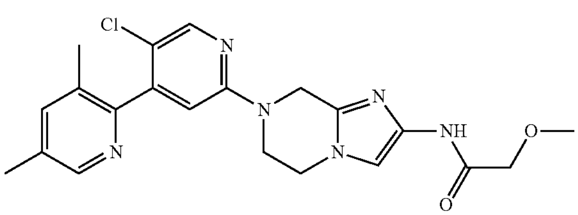 | N-(7-(5'-chloro-3,5-dimethyl-2,4'-bipyridin-2'-yl)-5,6,7,8-tetrahydroimidazo-[1,2-a]pyrazin-2-yl)-2-methoxyacetamide | E | 426.8 | ¹H NMR (400 MHz, CDCl₃) δ 8.65 (s, 1H), 8.36 (s, 1H), 8.26 (s, 1H), 7.44 (s, 1H), 7.29 (s, 1H), 6.65 (s, 1H), 4.64 (s, 2H), 4.15-4.07 (m, 4H), 4.02 (s, 2H), 3.47 (s, 3H), 2.39 (s, 3H), 2.18 (s, 3H) |

TABLE 1-continued

Selected compounds (A-1 to A-118) of the present invention.

| Example number | structure | Compound Name | Method | MS m/z (m + 1) | 1H NMR |
|---|---|---|---|---|---|
| A-15 | 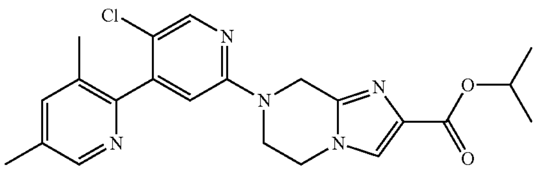 [SMILES: Cc1cnc(-c2cc(N3CCn4cc(C(=O)OC(C)C)nc4C3)ncc2Cl)c(C)c1] | isopropyl 7-(5'-chloro-3,5-dimethyl-2,4'-bipyridin-2'-yl)-5,6,7,8-tetrahydro-imidazo-[1,2-a]pyrazine-2-carboxylate | C | 425.8 | $^1$H NMR (300 MHz, CDCl$_3$) δ 8.34 (s, 1H), 8.24 (s, 1H), 7.56 (s, 1H), 7.43 (s, 1H), 6.62 (s, 1H), 5.34-5.18 (m, 1H), 4.74 (s, 2H), 4.16 (s, 4H), 2.38 (s, 3H), 2.16 (s, 3H), 1.37 (s, 3H), 1.35 (s, 3H) |
| A16 | 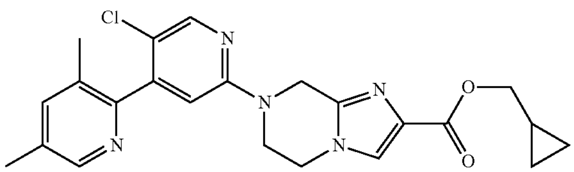 [SMILES: Cc1cnc(-c2cc(N3CCn4cc(C(=O)OCC5CC5)nc4C3)ncc2Cl)c(C)c1] | cyclopropylmethyl 7-(5'-chloro-3,5-dimethyl-2,4'-bipyridin-2'-yl)-5,6,7,8-tetrahydro-imidazo-[1,2-a]pyrazine-2-carboxylate | C | 437.8 | $^1$H NMR (300 MHz, CDCl$_3$) δ 8.35 (s, 1H), 8.25 (s, 1H), 7.59 (s,1H), 7.44 (s, 1H), 6.63 (s, 1H), 4.74 (s, 2H), 4.23-4.10 (m, 6H), 2.39 (s, 3H), 2.16 (s, 3H), 1.32-1.19 (m, 1H), 0.62-0.54 (m, 2H), 0.38-0.30 (m, 2H) |
| A-17 | 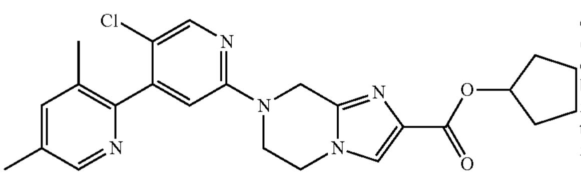 [SMILES: Cc1cnc(-c2cc(N3CCn4cc(C(=O)OC5CCCC5)nc4C3)ncc2Cl)c(C)c1] | cyclopentyl 7-(5'-chloro-3,5-dimethyl-2,4'-bipyridin-2'-yl)-5,6,7,8-tetrahydro-imidazo-[1,2-a]pyrazine-2-carboxylate | C | 451.8 | $^1$H NMR (300 MHz, CDCl$_3$) δ 8.35 (s, 1H), 8.24 (s, 1H), 7.53 (s, 1H), 7.44 (s, 1H), 6.63 (s, 1H), 5.38 (s, 1H), 4.73 (s, 2H), 4.16 (s, 4H), 2.38 (s, 3H), 2.16 (s, 3H), 2.08-1.92 (m, 2H), 1.89-1.73 (m, 4H), 1.59-1.56 (m, 2H) |
| A-18 | 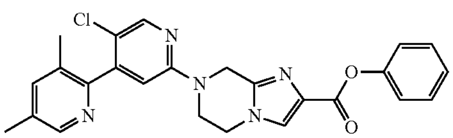 [SMILES: Cc1cnc(-c2cc(N3CCn4cc(C(=O)Oc5ccccc5)nc4C3)ncc2Cl)c(C)c1] | phenyl 7-(5'-chloro-3,5-dimethyl-2,4'-bipyridin-2'-yl)-5,6,7,8-tetrahydro-imidazo-[1,2-a]pyrazine-2-carboxylate | C | 459.8 | $^1$H NMR (300 MHz, CDCl$_3$) δ 8.35 (s, 1H), 8.26 (s, 1H), 7.74 (s,1H), 7.47-7.33 (m, 3H), 7.30-7.15 (m, 3H), 6.66 (s, 1H), 4.78 (s, 2H), 4.21 (s, 4H), 2.38 (s, 3H), 2.17 (s, 3H) |
| A-19 | 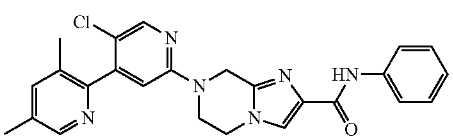 [SMILES: Cc1cnc(-c2cc(N3CCn4cc(C(=O)Nc5ccccc5)nc4C3)ncc2Cl)c(C)c1] | 7-(5'-chloro-3,5-dimethyl-2,4'-bipyridin-2'-yl)-N-phenyl-5,6,7,8-tetrahydro-imidazo-[1,2-a]pyrazine-2-carboxamide | C | 458.8 | $^1$H NMR (300 MHz, CDCl$_3$) δ 8.87 (s, 1H), 8.36 (s, 1H), 8.27 (s, 1H), 7.70 (s, 1H), 7.68 (s, 1H), 7.59 (s, 1H), 7.45 (s, 1H), 7.38-7.29 (m, 2H), 7.14-7.06 (m, 1H), 6.69 (s, 1H), 4.75 (s, 2H), 4.18 (s, 4H), 2.39 (s, 3H), 2.18 (s, 3H) |
| A-20 | 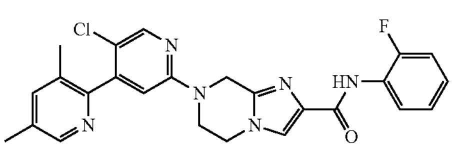 [SMILES: Cc1cnc(-c2cc(N3CCn4cc(C(=O)Nc5ccccc5F)nc4C3)ncc2Cl)c(C)c1] | 7-(5'-chloro-3,5-dimethyl-2,4'-bipyridin-2'-yl)-N-(2-fluorophenyl)-5,6,7,8-tetrahydro-imidazo-[1,2-a]pyrazine-2-carboxamide | C | 476.8 | $^1$H NMR (300 MHz, CDCl$_3$) δ 9.16 (s, 1H), 8.53-8.45 (m, 1H), 8.36 (s, 1H), 8.27 (s, 1H), 7.60 (s, 1H), 7.44 (s, 1H), 7.18-6.98 (m, 3H), 6.70 (s, 1H), 4.75 (s, 2H), 4.19 (s, 4H), 2.39 (s, 3H), 2.18 (s, 3H) |

TABLE 1-continued

Selected compounds (A-1 to A-118) of the present invention.

| Example number | structure | Compound Name | Method | MS m/z (m + 1) | 1H NMR |
|---|---|---|---|---|---|
| A-21 | 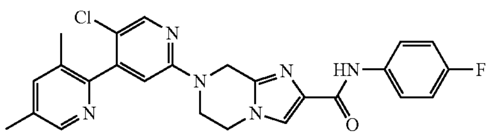 [SMILES: Cc1cnc(-c2cc(N3CCn4cc(C(=O)Nc5ccc(F)cc5)nc4C3)ncc2Cl)c(C)c1] | 7-(5'-chloro-3,5-dimethyl-2,4'-bipyridin-2'-yl)-N-(4-fluorophenyl)-5,6,7,8-tetrahydro-imidazo[1,2-a]pyrazine-2-carboxamide | C | 476.8 | $^1$H NMR (300 MHz, CDCl$_3$) δ 8.85 (s, 1H), 8.36 (s, 1H), 8.27 (s,1H), 7.69-7.61 (m, 2H), 7.59 (s, 1H), 7.44 (s, 1H), 7.08-6.96 (m, 2H), 6.69 (s, 1H), 4.74 (s, 2H), 4.18 (s, 4H), 2.39 (s, 3H), 2.17 (s, 3H) |
| A-22 | 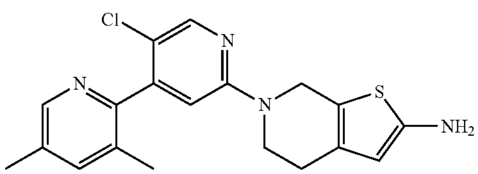 [SMILES: Cc1cnc(-c2cc(N3CCc4cc(N)sc4C3)ncc2Cl)c(C)c1] | 5-(5'-chloro-3,5-dimethyl-2,4'-bipyridin-2'-yl)-4,5,6,7-tetrahydro-thiazolo[5,4-c]pyridin-2-amine | F | 371.8 | $^1$H NMR (400 MHz, CDCl$_3$) δ 8.35 (s, 1H), 8.21 (s, 1H), 7.44 (s, 1H), 6.65 (s, 1H), 4.56 (s, 2H), 3.86 (s, 2H), 2.75 (s, 2H), 2.38 (s, 3H), 2.17 (s, 3H) |
| A-23 | 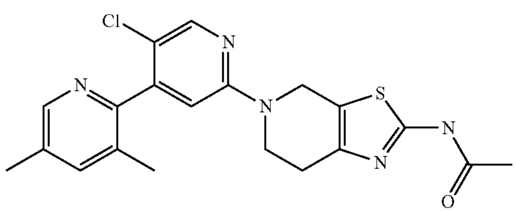 [SMILES: CC(=O)Nc1nc2c(s1)CN(c1cc(-c3ncc(C)cc3C)c(Cl)cn1)CC2] | N-(5-(5'-chloro-3,5-dimethyl-2,4'-bipyridin-2'-yl)-4,5,6,7-tetrahydro-thiazolo[5,4-c]pyridin-2-yl)acetamide | F | 413.8 | $^1$H NMR (400 MHz, CDCl$_3$) δ 9.55 (s, 1H), 8.35 (s, 1H), 8.22 (s, 1H), 7.43 (s, 1H), 6.66 (s, 1H), 4.68 (s, 2H), 3.96 (t, J = 5.6 Hz, 2H), 2.83 (t, J = 5.4 Hz, 2H), 2.38 (s, 3H), 2.23 (s, 3H), 2.17 (s, 3H) |
| A-24 | 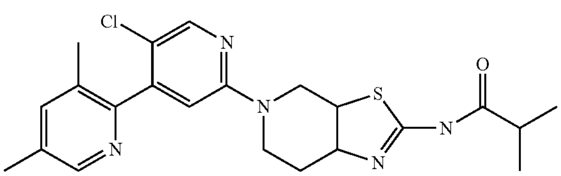 [SMILES: Cc1cnc(-c2cc(N3CCC4N=C(NC(=O)C(C)C)SC4C3)ncc2Cl)c(C)c1] | N-(5-(5'-chloro-3,5-dimethyl-2,4'-bipyridin-2'-yl)-4,5,6,7-tetrahydro-thiazolo[5,4-c]pyridin-2-yl)isobutyramide | F | 441.8 | $^1$H NMR (400 MHz, CDCl$_3$) δ 9.89 (s, 1H), 8.36 (s, 1H), 8.22 (s, 1H), 7.43 (s, 1H), 6.67 (s, 1H), 4.67 (s, 2H), 3.96 (t, J = 5.6 Hz, 2H), 2.82 (t, J = 5.4 Hz, 2H), 2.59 (m, 1H), 2.38 (s, 3H), 2.17 (s, 3H), 1.24 (d, J = 6.8 Hz, 6H) |
| A-25 | 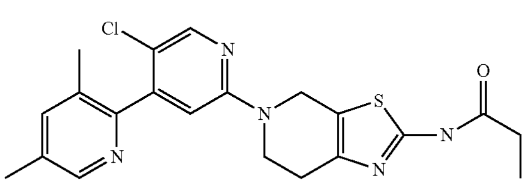 [SMILES: CCC(=O)Nc1nc2c(s1)CN(c1cc(-c3ncc(C)cc3C)c(Cl)cn1)CC2] | N-(5-(5'-chloro-3,5-dimethyl-2,4'-bipyridin-2'-yl)-4,5,6,7-tetrahydro-thiazolo[5,4-c]pyridin-2-yl)propionamide | F | 427.8 | $^1$H NMR (400 MHz, CDCl$_3$) δ 10.11 (s, 1H), 8.36 (s, 1H), 8.23 (s, 1H), 7.43 (s, 1H), 6.67 (s, 1H), 4.67 (s, 2H), 3.96 (t, J = 5.6 Hz, 2H), 2.82 (t, J = 5.0Hz, 2H), 2.45 (q, J = 7.5 Hz, 2H), 2.38 (s, 3H), 2.17 (s, 3H), 1.24 (t, J = 7.4 Hz, 3H) |
| A-26 | 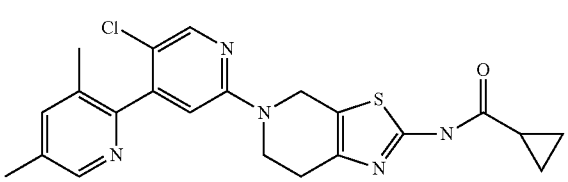 [SMILES: Cc1cnc(-c2cc(N3CCc4nc(NC(=O)C5CC5)sc4C3)ncc2Cl)c(C)c1] | N-(5-(5'-chloro-3,5-dimethyl-2,4'-bipyridin-2'-yl)-4,5,6,7-tetrahydro-thiazolo[5,4-c]pyridin-2-yl)cyclopropane carboxamide | F | 439.7 | $^1$H NMR (400 MHz, CDCl$_3$) δ 10.25 (s, 1H), 8.36 (s, 1H), 8.23 (s, 1H), 7.43 (s, 1H), 6.67 (s, 1H), 4.66 (s, 2H), 3.96 (t, J = 5.6 Hz, 2H), 2.83 (t, J = 5.2 Hz, 2H), 2.38 (s, 3H), 2.17 (s, 3H), 1.60 (m, 1H), 1.19-1.16 (m, 2H), 0.98-0.94 (m, 2H) |

TABLE 1-continued

Selected compounds (A-1 to A-118) of the present invention.

| Example number | structure | Compound Name | Method | MS m/z (m + 1) | 1H NMR |
|---|---|---|---|---|---|
| A-27 | 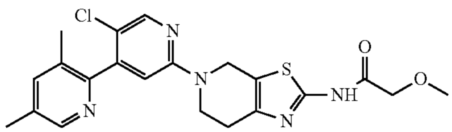 | N-(5-(5'-chloro-3,5-dimethyl-2,4'-bipyridin-2'-yl)-4,5,6,7-tetrahydrothiazolo[5,4-c]pyridin-2-yl)-2-methoxyacetamide | F | 443.8 | $^1$H NMR (400 MHz, CDCl$_3$) δ 9.65 (s, 1H), 8.35 (s, 1H), 8.22 (s, 1H), 7.43 (s, 1H), 6.67 (s, 1H), 4.71 (s, 2H), 4.11 (s, 2H), 3.96 (s, 2H), 3.49 (s, 3H), 2.85 (s, 2H), 2.37 (s, 3H), 2.16 (s, 3H) |
| A-28 | 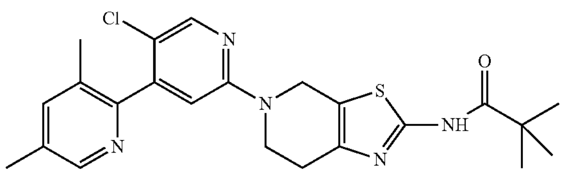 [SMILES: Cc1cnc(-c2cc(N3CCc4nc(NC(=O)C(C)(C)C)sc4C3)ncc2Cl)c(C)c1] | N-(5-(5'-chloro-3,5-dimethyl-2,4'-bipyridin-2'-yl)-4,5,6,7-tetrahydrothiazolo[5,4-c]pyridin-2-yl)pivalamide | F | 455.8 | $^1$H NMR (400 MHz, CDCl$_3$) δ 9.55 (s, 1H), 8.36 (s, 1H), 8.23 (s, 1H), 7.43 (s, 1H), 6.67 (s, 1H), 4.69 (s, 2H), 3.97 (t, J = 5.6 Hz, 2H), 2.83 (t, J = 5.6 Hz, 2H), 2.38 (s, 3H), 2.17 (s, 3H), 1.32 (s, 9H) |
| A-29 | 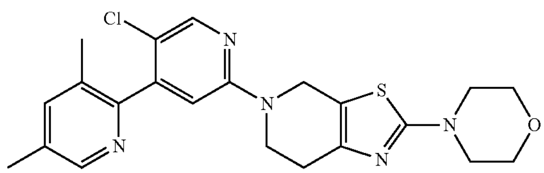 [SMILES: Cc1cnc(-c2cc(N3CCc4nc(N5CCOCC5)sc4C3)ncc2Cl)c(C)c1] | 4-(5-(5'-chloro-3,5-dimethyl-2,4'-bipyridin-2'-yl)-4,5,6,7-tetrahydrothiazolo[5,4-c]pyridin-2-yl)morpholine | G | 441.8 | $^1$H NMR (400 MHz, CDCl$_3$) δ 8.38 (s, 1H), 8.24 (s, 1H), 7.45 (s, 1H), 6.68 (s, 1H), 4.63 (s, 2H), 3.93 (t, J = 5.7 Hz, 2H), 3.82 (t, J = 4.8 Hz, 4H), 3.44 (t, J = 4.8 Hz, 4H), 2.80 (t, J = 5.4 Hz, 2H), 2.40 (s, 3H), 2.19 (s, 3H) |
| A-30 | 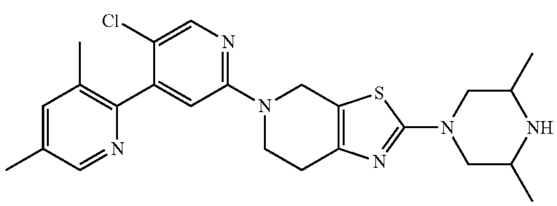 | 5-(5'-chloro-3,5-dimethyl-2,4'-bipyridin-2'-yl)-2-(3,5-dimethylpiperazin-1-yl)-4,5,6,7-tetrahydrothiazolo[5,4-c]pyridine | G | 468.8 | $^1$H NMR (400 MHz, CDCl$_3$) δ 8.34 (s, 1H), 8.20 (s, 1H), 7.41 (s, 1H), 6.64 (s, 1H), 4.58 (s, 2H), 3.90 (t, J = 5.6 Hz, 2H), 3.77-3.73 (m, 2H), 3.04-2.95 (m, 2H), 2.76 (t, J = 5.6 Hz, 2H), 2.63-2.57 (m, 2H), 2.36 (s, 3H), 2.16 (s, 3H), 1.14 (d, J = 6.4 Hz, 6H) |
| A-31 | 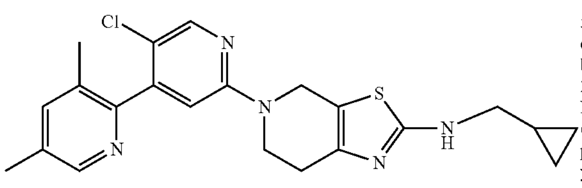 | 5-(5'-chloro-3,5-dimethyl-2,4'-bipyridin-2'-yl)-N-(cyclopropylmethyl)-4,5,6,7-tetrahydrothiazolo[5,4-c]pyridin-2-amine | G | 425.8 | $^1$H NMR (400 MHz, CDCl$_3$) δ 8.34 (s, 1H), 8.20 (s, 1H), 7.41 (s, 1H), 6.63 (s, 1H), 5.50 (s, 1H), 4.56 (s, 2H), 3.89 (t, J = 5.6 Hz, 2H), 3.08 (d, J = 7.2 Hz, 2H), 2.73 (t, J = 5.4 Hz, 2H), 2.36 (s, 3H), 2.15 (s, 3H), 1.10 (br s, 1H), 0.54 (d, J = 7.7 Hz, 2H), 0.24 (d, J = 5.1 Hz, 2H) |
| A-32 | 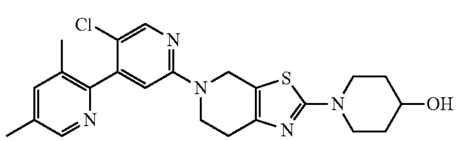 [SMILES: Cc1cnc(-c2cc(N3CCc4nc(N5CCC(O)CC5)sc4C3)ncc2Cl)c(C)c1] | 1-(5-(5'-chloro-3,5-dimethyl-2,4'-bipyridin-2'-yl)-4,5,6,7-tetrahydrothiazolo[5,4-c]pyridin-2-yl)piperidin-4-ol | G | 455.8 | $^1$H NMR (400 MHz, CDCl$_3$) δ 8.33 (s, 1H), 8.20 (s, 1H), 7.42 (s, 1H), 6.64 (s, 1H), 4.58 (s, 2H), 3.89 (t, J = 5.6 Hz, 2H), 3.87-3.84 (m, 1H), 3.78-3.73 (m, 2H), 3.20-3.14 (m, 2H), 2.75 (t, J = 5.6 Hz, 2H), 2.36 (s, 3H), 2.15 (s, 3H), 1.95-1.89 (m, 2H), 1.65-1.56 (m, 2H) |
| A-33 | 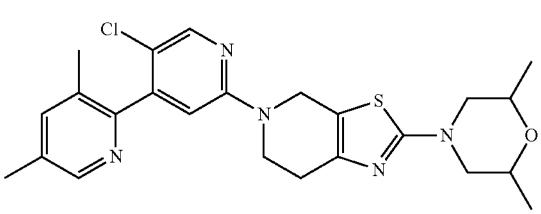 | 4-(5-(5'-chloro-3,5-dimethyl-2,4'-bipyridin-2'-yl)-4,5,6,7-tetrahydrothiazolo[5,4-c]pyridin-2-yl)-2,6-dimethylmorpholine | G | 469.8 | $^1$H NMR (400 MHz, CDCl$_3$) δ 8.34 (s, 1H), 8.21 (s, 1H), 7.42 (s, 1H), 6.65 (s, 1H), 4.60 (s, 2H), 3.91 (t, J = 5.8 Hz, 2H), 3.78-3.71 (m, 2H), 3.68 (d, J = 12.8 Hz, 2H), 2.77 (t, J = 5.6 Hz, 2H), 2.70 (t, J = 11.6 Hz, 2H), 2.37 (s, 3H), 2.16 (s, 3H), 1.24 (d, J = 6.4 Hz, 6H) |

TABLE 1-continued

Selected compounds (A-1 to A-118) of the present invention.

| Example number | structure | Compound Name | Method | MS m/z (m + 1) | 1H NMR |
|---|---|---|---|---|---|
| A-34 | 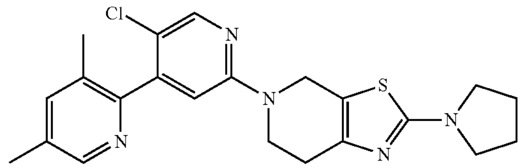 [SMILES: Cc1cnc(-c2cc(N3CCc4nc(N5CCCC5)sc4C3)ncc2Cl)c(C)c1] | 5-(5'-chloro-3,5-dimethyl-2,4'-bipyridin-2'-yl)-2-(pyrrolidin-1-yl)-4,5,6,7-tetrahydrothiazolo[5,4-c]pyridine | G | 425.8 | $^1$H NMR (400 MHz, CDCl$_3$) δ 8.34 (s, 1H), 8.20 (s, 1H), 7.41 (s, 1H), 6.64 (s, 1H), 4.59 (s, 2H), 3.91 (t, J = 5.6 Hz, 2H), 3.43 (t, J = 6.4 Hz, 4H), 2.79 (t, J = 5.4 Hz, 2H), 2.36 (s, 3H), 2.16 (s, 3H), 2.03-2.00 (m, 4H) |
| A-35 | 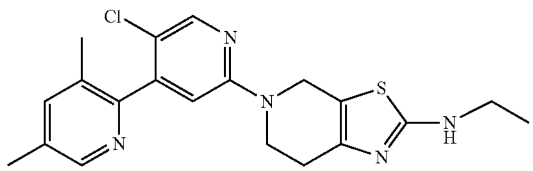 [SMILES: CCNc1nc2c(s1)CN(c1cc(-c3ncc(C)cc3C)c(Cl)cn1)CC2] | 5-(5'-chloro-3,5-dimethyl-2,4'-bipyridin-2'-yl)-N-ethyl-4,5,6,7-tetrahydrothiazolo[5,4-c]pyridin-2-amine | G | 399.8 | $^1$H NMR (400 MHz, CDCl$_3$) δ 8.36 (s, 1H), 8.20 (s, 1H), 7.42 (s, 1H), 6.63 (s, 1H), 4.55 (s, 2H), 3.86 (s, 2H), 3.24 (s, 2H), 2.72 (s, 2H), 2.37 (s, 3H), 2.16 (s, 3H), 1.31 (t, J = 6.6 Hz, 3H) |
| A-36 | 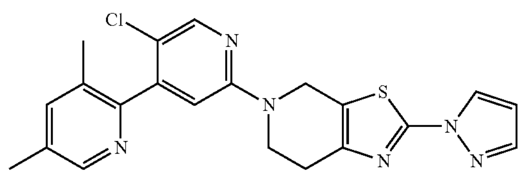 [SMILES: Cc1cnc(-c2cc(N3CCc4nc(-n5cccn5)sc4C3)ncc2Cl)c(C)c1] | 5-(5'-chloro-3,5-dimethyl-2,4'-bipyridin-2'-yl)-2-(1H-pyrazol-1-yl)-4,5,6,7-tetrahydrothiazolo[5,4-c]pyridine | G | 422.7 | $^1$H NMR (400 MHz, CDCl$_3$) δ 8.36 (s, 1H), 8.28 (s, 1H), 8.24 (s, 1H), 7.70 (s, 1H), 7.44 (s, 1H), 6.70 (s, 1H), 6.46 (s, 1H), 4.77 (s, 2H), 3.99 (s, 2H), 2.93 (s, 2H), 2.38 (s, 3H), 2.17 (s, 3H) |
| A-37 | 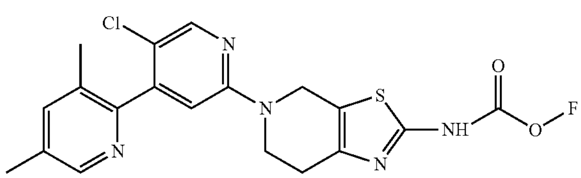 [SMILES: Cc1cnc(-c2cc(N3CCc4nc(NC(=O)OF)sc4C3)ncc2Cl)c(C)c1] | ethyl 5-(5'-chloro-3,5-dimethyl-2,4'-bipyridin-2'-yl)-4,5,6,7-tetrahydrothiazolo[5,4-c]pyridin-2-ylcarbamate | F | 443.8 | $^1$H NMR (400 MHz, CDCl$_3$) δ 9.95 (s, 1H), 8.35 (s, 1H), 8.23 (s, 1H), 7.43 (s, 1H), 6.67 (s, 1H), 4.67 (s, 2H), 4.30 (q, J = 6.9 Hz, 2H), 3.95 (s, 2H), 2.86 (s, 2H), 2.38 (s, 3H), 2.17 (s, 3H), 1.34 (t, J = 6.9 Hz, 3H) |
| A-38 | 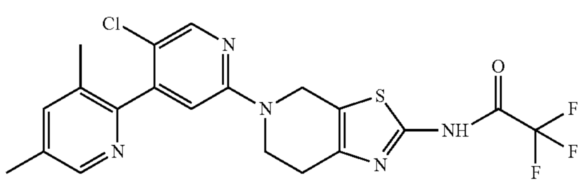 [SMILES: Cc1cnc(-c2cc(N3CCc4nc(NC(=O)C(F)(F)F)sc4C3)ncc2Cl)c(C)c1] | N-(5-(5'-chloro-3,5-dimethyl-2,4'-bipyridin-2'-yl)-4,5,6,7-tetrahydrothiazolo[5,4-c]pyridin-2-yl)-2,2,2-trifluoroacetamide | F | 467.7 | $^1$H NMR (400 MHz, CDCl$_3$) δ 8.42 (s, 1H), 8.21 (s, 1H), 7.47 (s, 1H), 6.70 (s, 1H), 4.67 (s, 2H), 3.86 (s, 2H), 2.66 (s, 2H), 2.39 (s, 3H), 2.17 (s, 3H) |
| A-39 | 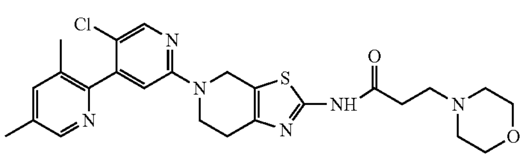 [SMILES: Cc1cnc(-c2cc(N3CCc4nc(NC(=O)CCN5CCOCC5)sc4C3)ncc2Cl)c(C)c1] | N-(5-(5'-chloro-3,5-dimethyl-2,4'-bipyridin-2'-yl)-4,5,6,7-tetrahydrothiazolo[5,4-c]pyridin-2-yl)-3-morpholinopropanamide | F | 512.7 | $^1$H NMR (400 MHz, CDCl$_3$) δ 8.35 (s, 1H), 8.22 (s, 1H), 7.43 (s, 1H), 6.66 (s, 1H), 4.68 (s, 2H), 3.95 (t, J = 5.2 Hz, 2H), 3.85 (s, 4H), 2.84 (s, 2H), 2.78 (t, J = 5.6 Hz, 2H), 2.64 (s, 6H), 2.37 (s, 3H), 2.16 (s, 3H) |
| A-40 | 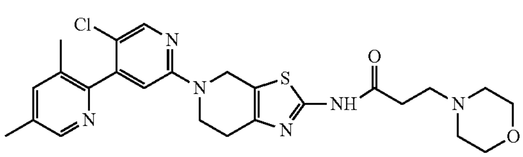 [SMILES: Cc1cnc(-c2cc(N3CCc4nc(NC(=O)CCN5CCOCC5)sc4C3)ncc2Cl)c(C)c1] | N-(5-(5'-chloro-3,5-dimethyl-2,4'-bipyridin-2'-yl)-4,5,6,7-tetrahydrothiazolo[5,4-c]pyridin-2-yl)-3-(piperidin-1-yl)propanamide | F | 510.7 | $^1$H NMR (400 MHz, CDCl$_3$) δ 8.36 (s, 1H), 8.22 (s, 1H), 7.43 (s, 1H), 6.67 (s, 1H), 4.68 (s, 2H), 3.95 (t, J = 5.2 Hz, 2H), 2.85 (s, 4H), 2.73 (t, J = 5.8 Hz, 2H), 2.68 (s, 4H), 2.38 (s, 3H), 2.17 (s, 3H), 1.80 (t, J = 5 Hz, 4H), 1.57 (s, 2H) |

TABLE 1-continued

Selected compounds (A-1 to A-118) of the present invention.

| Example number | structure | Compound Name | Method | MS m/z (m + 1) | 1H NMR |
|---|---|---|---|---|---|
| A-41 | 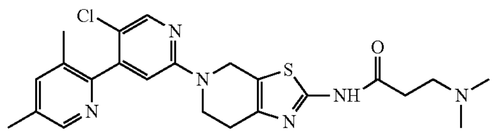 | N-(5-(5'-chloro-3,5-dimethyl-2,4'-bipyridin-2'-yl)-4,5,6,7-tetrahydrothiazolo-[5,4-c]pyridin-2-yl)-3-(dimethylamino)propanamide | F | 470.8 | $^1$H NMR (400 MHz, CDCl$_3$) δ 8.35 (s, 1H), 8.22 (s, 1H), 7.43 (s, 1H), 6.66 (s, 1H), 4.66 (s, 2H), 3.94 (t, J = 5.2 Hz, 2H), 3.02 (s, 2H), 2.89-2.83 (m, 4H), 2.61 (s, 6H), 2.38 (s, 3H), 2.17 (s, 3H) |
| A-42 | 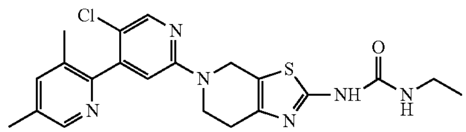 [SMILES: CCNC(=O)Nc1nc2c(s1)CN(c1cc(-c3ncc(C)cc3C)c(Cl)cn1)CC2] | 1-(5-(5'-chloro-3,5-dimethyl-2,4'-bipyridin-2'-yl)-4,5,6,7-tetrahydrothiazolo-[5,4-c]pyridin-2-yl)-3-ethylurea | F | 442.8 | $^1$H NMR (400 MHz, CDCl$_3$) δ 8.36 (s, 1H), 8.22 (s, 1H), 7.44 (s, 1H), 6.67 (s, 1H), 4.61 (s, 2H), 3.95 (s, 2H), 3.39-3.32 (m, 2H), 2.82 (s, 2H), 2.38 (s, 3H), 2.17 (s, 3H), 1.21 (t, J = 7.2 Hz, 3H) |
| A-43 | 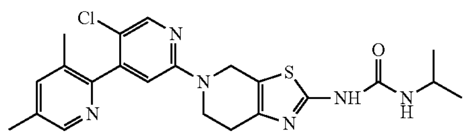 [SMILES: Cc1cnc(-c2cc(N3CCc4nc(NC(=O)NC(C)C)sc4C3)ncc2Cl)c(C)c1] | 1-(5-(5'-chloro-3,5-dimethyl-2,4'-bipyridin-2'-yl)-4,5,6,7-tetrahydrothiazolo-[5,4-c]pyridin-2-yl)-3-isopropylurea | F | 456.8 | $^1$H NMR (400 MHz, CDCl$_3$) δ 8.35 (s, 1H), 8.23 (s, 1H), 7.43 (s, 1H), 6.67 (s, 1H), 4.62 (s, 2H), 4.01 (m, 1H), 3.95 (s, 2H), 2.82 (s, 2H), 2.38 (s, 3H), 2.17 (s, 3H), 1.23 (s, 6H) |
| A-44 | 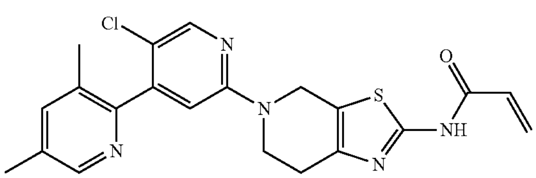 [SMILES: C=CC(=O)Nc1nc2c(s1)CN(c1cc(-c3ncc(C)cc3C)c(Cl)cn1)CC2] | N-(5-(5'-chloro-3,5-dimethyl-2,4'-bipyridin-2'-yl)-4,5,6,7-tetrahydrothiazolo-[5,4-c]pyridin-2-yl)acrylamide | F | 425.8 | $^1$H NMR (300 MHz, DMSO-d$_6$) δ 12.24 (s, 1H), 8.30 (s, 1H), 8.23 (s, 1H), 7.57 (s, 1H), 6.90 (s, 1H), 6.52-6.43 (m, 1H), 6.35 (d, J = 17.4 Hz, 1H), 5.86 (d, J = 9.3 Hz, 1H), 4.71 (s, 2H), 3.95 (t, J = 5.0 Hz, 2H), 2.71 (s, 2H), 2.31 (s, 3H), 2.07 (s, 3H) |
| A-45 | 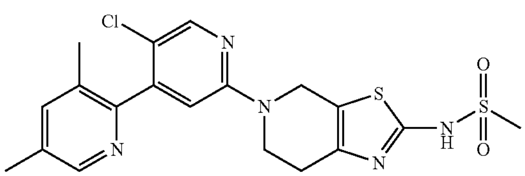 | N-(5-(5'-chloro-3,5-dimethyl-2,4'-bipyridin-2'-yl)-4,5,6,7-tetrahydrothiazolo-[5,4-c]pyridin-2-yl)methanesulfonamide | F | 449.7 | $^1$H NMR (300 MHz, CDCl$_3$) δ 8.35 (s, 1H), 8.22 (s, 1H), 7.44 (s, 1H), 6.65 (s, 1H), 4.53 (s, 2H), 3.90 (s, 2H), 2.99 (s, 3H), 2.78 (s, 2H), 2.38 (s, 3H), 2.16 (s, 3H) |
| A46 | 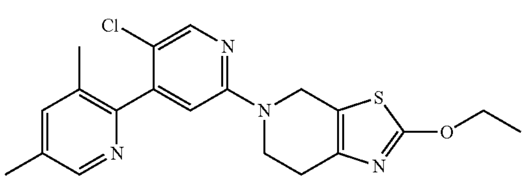 [SMILES: CCOc1nc2c(s1)CN(c1cc(-c3ncc(C)cc3C)c(Cl)cn1)CC2] | 5-(5'-chloro-3,5-dimethyl-2,4'-bipyridin-2'-yl)-2-ethoxy-4,5,6,7-tetrahydrothiazolo-[5,4-c]pyridine | G | 400.8 | $^1$H NMR (300 MHz, CDCl$_3$) δ 8.35 (s, 1H), 8.21 (s, 1H), 7.42 (s, 1H), 6.65 (s, 1H), 4.59 (s, 2H), 4.41 (q, J = 7.1 Hz, 2H), 3.92 (t, J = 5.6 Hz, 2H), 2.77 (t, J = 5.3 Hz, 2H), 2.37 (s, 3H), 2.16 (s, 3H), 1.41 (t, J = 7.1 Hz, 3H) |
| A-47 | 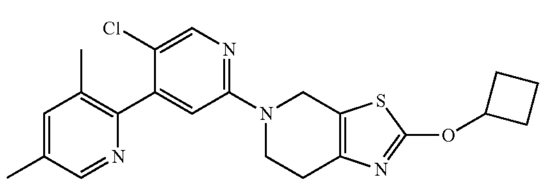 [SMILES: Cc1cnc(-c2cc(N3CCc4nc(OC5CCC5)sc4C3)ncc2Cl)c(C)c1] | 5-(5'-chloro-3,5-dimethyl-2,4'-bipyridin-2'-yl)-2-cyclobutoxy-4,5,6,7-tetrahydrothiazolo-[5,4-c]pyridine | G | 426.8 | $^1$H NMR (300 MHz, CDCl$_3$) δ 8.34 (s, 1H), 8.21 (s, 1H), 7.42 (s, 1H), 6.64 (s, 1H), 5.08 (m, 1H), 4.59 (s, 2H), 3.91 (t, J = 5.6 Hz, 2H), 2.76 (t, J = 5.1 Hz, 2H), 2.5-2.40 (m, 2H), 2.37 (s, 3H), 2.27-2.18 (m, 2H), 2.16 (s, 3H), 1.91-1.77(m, 1H), 1.71-1.64 (m, 1H) |

TABLE 1-continued

Selected compounds (A-1 to A-118) of the present invention.

| Example number | structure | Compound Name | Method | MS m/z (m + 1) | 1H NMR |
|---|---|---|---|---|---|
| A-48 | 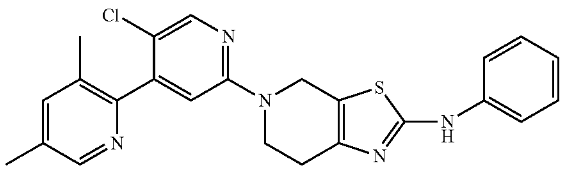 [SMILES: Cc1cnc(-c2cc(N3CCc4nc(Nc5ccccc5)sc4C3)ncc2Cl)c(C)c1] | 5-(5'-chloro-3,5-dimethyl-2,4'-bipyridin-2'-yl)-N-phenyl-4,5,6,7-tetrahydrothiazolo[5,4-c]pyridin-2-amine | G | 447.8 | $^1$H NMR (400 MHz, CDCl$_3$) δ 8.36 (s, 1H), 8.22 (s, 1H), 7.43 (s, 1H), 7.36-7.32 (m, 4H), 7.06 (t, J = 6 Hz, 1H), 6.66 (s, 1H), 4.63 (s, 2H), 3.93 (s, 2H), 2.81 (s, 2H), 2.38 (s, 3H), 2.17 (s, 3H) |
| A-49 | 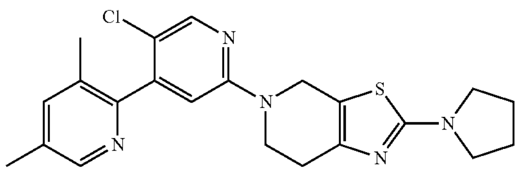 [SMILES: Cc1cnc(-c2cc(N3CCc4nc(N5CCCC5)sc4C3)ncc2Cl)c(C)c1] | 5-(5'-chloro-3,5-dimethyl-2,4'-bipyridin-2'-yl)-2-(pyrrolidin-1-yl)-6,7-dihydrothiazolo[5,4-c]pyridin-4(5H)-one | H | 440.3 | $^1$H NMR (400 MHz, CDCl$_3$) δ 8.43 (s, 1H), 8.33 (s, 1H), 7.93 (s, 1H), 7.42 (s, 1H), 4.37 (t, J = 6.6 Hz, 2H), 3.53 (s, 4H), 3.01 (t, J = 6.6 Hz, 2H), 2.36 (s, 3H), 2.22 (s, 3H), 2.10-2.07 (m, 4H) |
| A-50 | 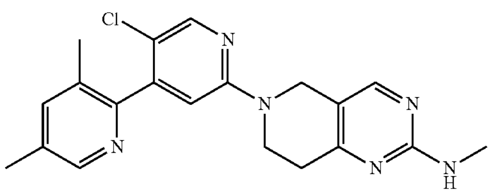 | 6-(5'-chloro-3,5-dimethyl-2,4'-bipyridin-2'-yl)-N-methyl-5,6,7,8-tetrahydropyrido[4,3-d]pyrimidin-2-amine | I | 380.8 | $^1$H NMR (400 MHz, CDCl$_3$) δ 8.35 (s, 1H), 8.23 (s, 1H), 8.11 (s, 1H), 7.43 (s, 1H), 6.65 (s, 1H), 4.54 (s, 2H), 3.90 (s, 2H), 3.00 (d, J = 5.0 Hz, 3H), 2.88 (s, 2H), 2.37 (s, 3H), 2.17 (s, 3H) |
| A-51 | 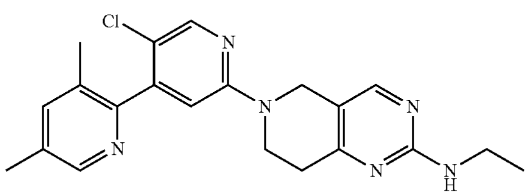 [SMILES: CCNc1ncc2c(n1)CCN(c1cc(-c3ncc(C)cc3C)c(Cl)cn1)C2] | 6-(5'-chloro-3,5-dimethyl-2,4'-bipyridin-2'-yl)-N-ethyl-5,6,7,8-tetrahydropyrido[4,3-d]pyrimidin-2-amine | I | 394.9 | $^1$H NMR (400 MHz, CDCl$_3$) δ 8.34 (s, 1H), 8.22 (s, 1H), 8.08 (s, 1H), 7.41 (s, 1H), 6.63 (s, 1H), 4.52 (s, 2H), 3.89 (t, J = 5.6 Hz, 2H), 3.47-3.37 (m, 2H), 2.85 (t, J = 5.8 Hz, 2H), 2.36 (s, 3H), 2.16 (s, 3H), 1.21 (t, J = 7.2 Hz, 3H) |
| A-52 | 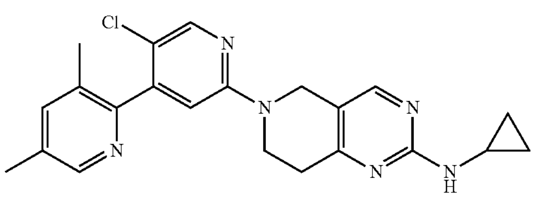 [SMILES: Cc1cnc(-c2cc(N3CCc4nc(NC5CC5)ncc4C3)ncc2Cl)c(C)c1] | 6-(5'-chloro-3,5-dimethyl-2,4'-bipyridin-2'-yl)-N-cyclopropyl-5,6,7,8-tetrahydropyrido[4,3-d]pyrimidin-2-amine | I | 406.9 | $^1$H NMR (400 MHz, CDCl$_3$) δ 8.39 (s, 1H), 8.23 (s, 1H), 8.17 (s, 1H), 7.42 (s, 1H), 6.65 (s, 1H), 4.55 (s, 2H), 3.90 (t, J = 5.6 Hz, 2H), 2.88 (t, J = 5.8 Hz, 2H), 2.77 (m, 1H), 2.42 (s, 3H), 2.21 (s, 3H), 1.29 (s, 1H), 0.87-079 (m, 2H), 0.62-0.55 (m, 2H) |
| A-53 | 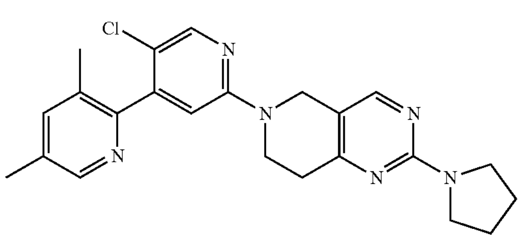 | 6-(5'-chloro-3,5-dimethyl-2,4'-bipyridin-2'-yl)-2-(pyrrolidin-1-yl)-5,6,7,8-tetrahydropyrido[4,3-d]pyrimidine | I | 420.8 | $^1$H NMR (400 MHz, CDCl$_3$) δ 8.35 (s, 1H), 8.23 (s, 1H), 8.12 (s, 1H), 7.42 (s, 1H), 6.63 (s, 1H), 4.51 (s, 2H), 3.89 (t, J = 5.6 Hz, 2H), 3.56 (t, J = 6.5 Hz, 4H), 2.89 (t, J = 5.8 Hz, 2H), 2.37 (s, 3H), 2.17 (s, 3H), 1.97 (t, J = 6.6 Hz, 4H) |

TABLE 1-continued

Selected compounds (A-1 to A-118) of the present invention.

| Example number | structure | Compound Name | Method | MS m/z (m + 1) | 1H NMR |
|---|---|---|---|---|---|
| A-54 | 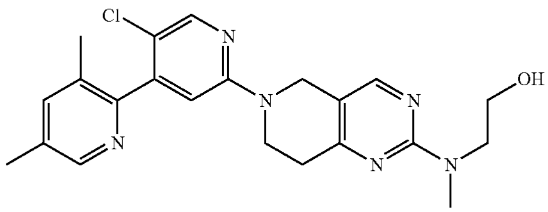 [SMILES: Cc1cnc(-c2cc(N3CCc4nc(N(C)CCO)ncc4C3)ncc2Cl)c(C)c1] | 2-((6-(5'-chloro-3,5-dimethyl-2,4'-bipyridin-2'-yl)-5,6,7,8-tetrahydropyrido[4,3-d]pyrimidin-2-yl)(methyl)amino)ethanol | I | 424.8 | $^1$H NMR (400 MHz, CDCl$_3$) δ 8.33 (s, 1H), 8.21 (s, 1H), 8.08 (s, 1H), 7.41 (s, 1H), 6.63 (s, 1H), 4.51 (s, 2H), 3.87(s, 4H), 3.74 (s, 2H), 3.19(s, 3H), 2.86 (s, 2H), 2.35 (s, 3H), 2.15 (s, 3H) |
| A-55 | 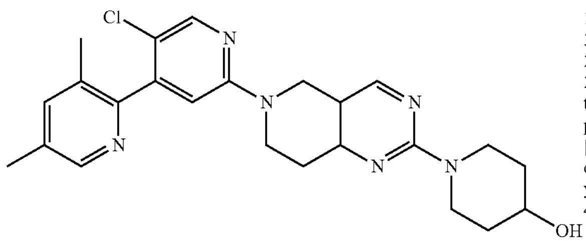 [SMILES: Cc1cnc(-c2cc(N3CCC4N=C(N5CCC(O)CC5)N=CC4C3)ncc2Cl)c(C)c1] | 1-(6-(5'-chloro-3,5-dimethyl-2,4'-bipyridin-2'-yl)-5,6,7,8-tetrahydropyrido[4,3-d]pyrimidin-2-yl)piperidin-4-ol | I | 450.8 | $^1$H NMR (400 MHz, CDCl$_3$) δ 8.37 (s, 1H), 8.24 (s, 1H), 8.12 (s, 1H), 7.47 (s, 1H), 6.66 (s, 1H), 4.53 (s, 2H), 4.43 (s, 2H), 3.40 (s, 3H), 3.31 (s, 2H), 2.89 (s, 2H), 2.39 (s, 3H), 2.25 (s, 3H), 1.94 (s, 2H), 1.55 (s, 2H) |
| A-56 | 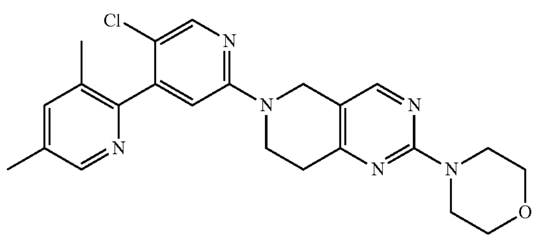 [SMILES: Cc1cnc(-c2cc(N3CCc4nc(N5CCOCC5)ncc4C3)ncc2Cl)c(C)c1] | 4-(6-(5'-chloro-3,5-dimethyl-2,4'-bipyridin-2'-yl)-5,6,7,8-tetrahydropyrido[4,3-d]pyrimidin-2-yl)morpholine | I | 436.8 | $^1$H NMR (400 MHz, CDCl$_3$) δ 8.40 (s, 1H), 8.25 (s, 1H), 8.15 (s, 1H), 7.52 (s, 1H), 6.69 (s, 1H), 4.56 (s, 2H), 3.91(s, 3H), 3.78-3.78 (m, 8H), 2.90 (s, 2H), 2.41 (s, 3H), 2.21 (s, 3H) |
| A-57 | 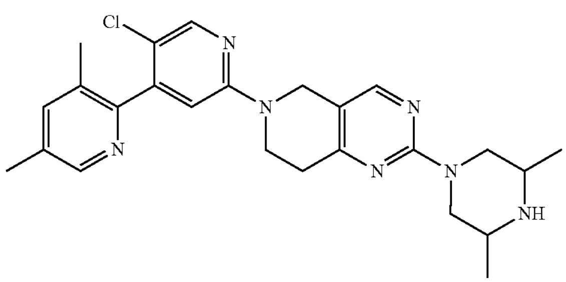 | 6-(5'-chloro-3,5-dimethyl-2,4'-bipyridin-2'-yl)-2-(3,5-dimethylpiperazin-1-yl)-5,6,7,8-tetrahydropyrido[4,3-d]pyrimidine | I | 463.8 | $^1$H NMR (400 MHz, CDCl$_3$) δ 8.29 (s, 1H), 8.17 (s, 1H), 8.06 (s, 1H), 7.36 (s, 1H), 6.59 (s, 1H), 4.82-4.59 (m, 2H), 4.48 (s, 2H), 3.84 (t, J = 5.2 Hz, 2H), 3.08 (s, 4H), 2.82 (t, J = 6.0 Hz, 2H), 2.31 (s, 3H), 2.11 (s, 3H), 1.50 (s, 6H) |
| A-58 | 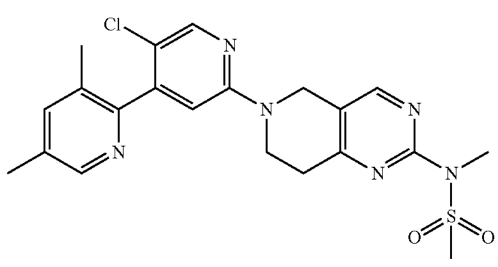 [SMILES: Cc1cnc(-c2cc(N3CCc4nc(N(C)S(C)(=O)=O)ncc4C3)ncc2Cl)c(C)c1] | N-(6-(5'-chloro-3,5-dimethyl-2,4'-bipyridin-2'-yl)-5,6,7,8-tetrahydropyrido[4,3-d]pyrimidin-2-yl)-N-methylmethanesulfonamide | I | 458.8 | $^1$H NMR (400 MHz, CDCl$_3$) δ 8.33 (s, 1H), 8.31 (s, 1H), 8.19 (s, 1H), 7.47 (s, 1H), 6.66 (s, 1H), 4.62 (s, 2H), 3.88 (t, J = 5.6 Hz, 2H), 3.47 (s, 3H), 3.44 (s, 3H), 2.97 (t, J=5.6 Hz, 2H), 2.35 (s, 3H), 2.15 (s, 3H) |
| A-59 | 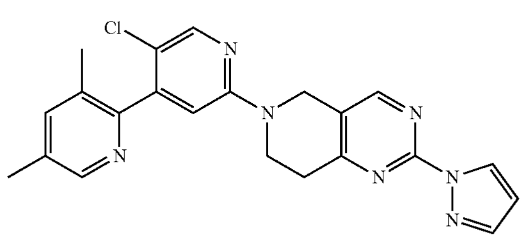 [SMILES: Cc1cnc(-c2cc(N3CCc4nc(-n5cccn5)ncc4C3)ncc2Cl)c(C)c1] | 6-(5'-chloro-3,5-dimethyl-2,4'-bipyridin-2'-yl)-2-(1H-pyrazol-1-yl)-5,6,7,8-tetrahydropyrido[4,3-d]pyrimidine | I | 417.8 | $^1$H NMR (400 MHz, CDCl$_3$) δ 8.56 (s, 1H), 8.51 (s, 1H), 8.38 (s, 1H), 8.25 (s, 1H), 7.80 (s, 1H), 7.52 (s, 1H), 6.74 (s, 1H), 6.47 (s, 1H), 4.76 (s, 2H), 3.97 (s, 2H), 3.16 (s, 2H), 2.40 (s, 3H), 2.20 (s, 3H) |

TABLE 1-continued

Selected compounds (A-1 to A-118) of the present invention.

| Example number | structure | Compound Name | Method | MS m/z (m + 1) | 1H NMR |
|---|---|---|---|---|---|
| A-60 | 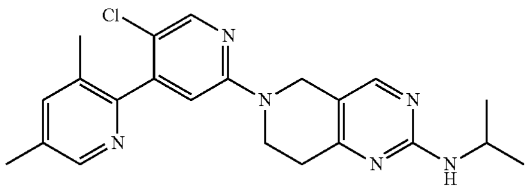 [SMILES: Cc1cnc(-c2cc(N3CCc4nc(NC(C)C)ncc4C3)ncc2Cl)c(C)c1] | 6-(5'-chloro-3,5-dimethyl-2,4'-bipyridin-2'-yl)-N-isopropyl-5,6,7,8-tetrahydro-pyrido-[4,3-d]pyrimidin-2-amine | I | 408.8 | $^1$H NMR (400 MHz, CDCl$_3$) δ 8.35 (s, 1H), 8.23 (s, 1H), 8.09 (s, 1H), 7.43 (s, 1H), 6.64 (s, 1H), 4.93 (d, J = 7.6 Hz, 1H), 4.53 (s, 2H), 4.13 (m, 1H), 3.90 (s, 2H), 2.84 (t, J = 5.6 Hz, 2H), 2.36 (s, 3H), 2.18 (s, 3H), 1.23 (d, J = 6.4 Hz, 6H) |
| A-61 | 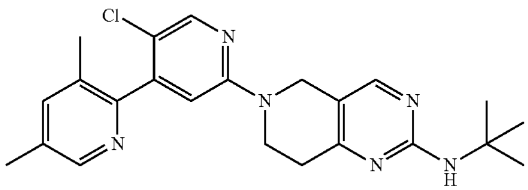 [SMILES: Cc1cnc(-c2cc(N3CCc4nc(NC(C)(C)C)ncc4C3)ncc2Cl)c(C)c1] | N-tert-butyl-6-(5'-chloro-3,5-dimethyl-2,4'-bipyridin-2'-yl)-5,6,7,8-tetrahydro-pyrido-[4,3-d]pyrimidin-2-amine | I | 422.8 | $^1$H NMR (400 MHz, CDCl$_3$) δ 8.35 (s, 1H), 8.23 (s, 1H), 8.06 (s, 1H), 7.42 (s, 1H), 6.63 (s, 1H), 5.15 (s, 1H), 4.51 (s, 2H), 3.88 (t, J = 5.2 Hz, 2H), 2.84 (t, J = 5.8 Hz, 2H), 2.37 (s, 3H), 2.17 (s, 3H), 1.43 (s, 9H) |
| A-62 | 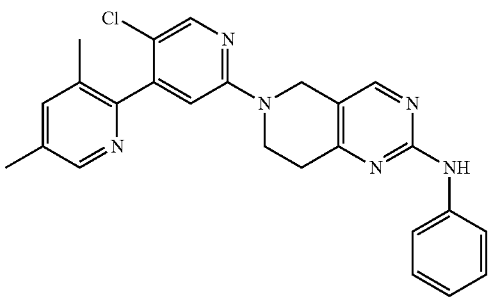 [SMILES: Cc1cnc(-c2cc(N3CCc4nc(Nc5ccccc5)ncc4C3)ncc2Cl)c(C)c1] | 6-(5'-chloro-3,5-dimethyl-2,4'-bipyridin-2'-yl)-N-phenyl-5,6,7,8-tetrahydro-pyrido-[4,3-d]pyrimidin-2-amine | I | 442.8 | $^1$H NMR (400 MHz, CDCl$_3$) δ 8.41 (s, 1H), 8.26 (d, J = 5.2 Hz, 2H), 7.64 (s, 1H), 7.62 (s, 1H), 7.55 (s, 1H), 7.34 (t, J = 7.2 Hz, 2H), 7.06 (t, J = 7.8 Hz, 1H), 6.73 (s, 1H), 4.63 (s, 2H), 3.95 (s, 2H), 3.01 (t, J = 5.4 Hz, 2H), 2.42 (s, 3H), 2.22 (s, 3H) |
| A-63 | 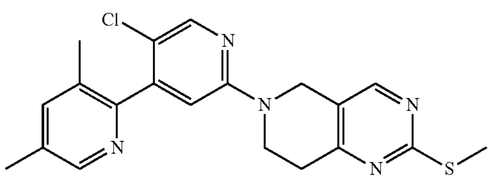 | 6-(5'-chloro-3,5-dimethyl-2,4'-bipyridin-2'-yl)-2-(methylthio)-5,6,7,8-tetrahydro-pyrido-[4,3-d]pyrimidine | I | 397.8 | $^1$H NMR (400 MHz, CDCl$_3$) δ 8.38 (s, 1H), 8.33 (s, 1H), 8.25 (s, 1H), 7.48 (s, 1H), 6.70 (s, 1H), 4.67 (s, 2H), 3.93 (t, J = 5.1 Hz, 2H), 3.01 (t, J = 5.4 Hz, 2H), 2.56 (s, 3H), 2.40 (s, 3H), 2.20 (s, 3H) |
| A-64 | 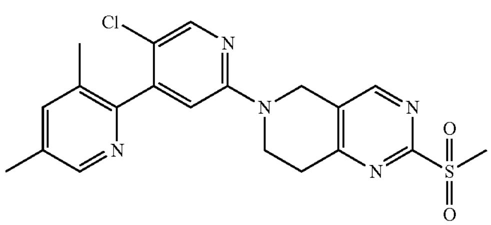 | 6-(5'-chloro-3,5-dimethyl-2,4'-bipyridin-2'-yl)-2-(methylsulfonyl)-5,6,7,8-tetrahydro-pyrido-[4,3-d]pyrimidine | I | 429.8 | $^1$H NMR (400 MHz, CDCl$_3$) δ 8.69 (s, 1H), 8.35 (s, 1H), 8.25 (s, 1H), 7.44 (s, 1H), 6.74 (s, 1H), 4.87 (s, 2H), 3.97 (t, J = 5.6 Hz, 2H), 3.35 (s, 3H), 3.22 (t, J = 5.8 Hz, 2H), 2.38 (s, 3H), 2.18 (s, 3H) |
| A-65 | 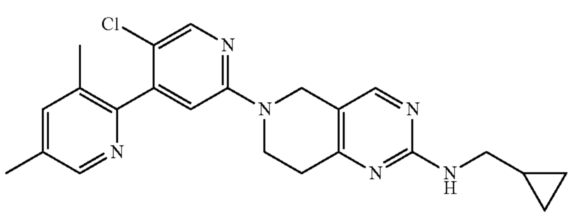 [SMILES: Cc1cnc(-c2cc(N3CCc4nc(NCC5CC5)ncc4C3)ncc2Cl)c(C)c1] | 6-(5'-chloro-3,5-dimethyl-2,4'-bipyridin-2'-yl)-N-(cyclopropylmethyl)-5,6,7,8-tetrahydro-pyrido-[4,3-d]pyrimidin-2-amine | I | 420.8 | $^1$H NMR (400 MHz, CDCl$_3$) δ 8.35 (s, 1H), 8.23 (s, 1H), 8.09 (s, 1H), 7.42 (s, 1H), 6.64 (s, 1H), 5.16 (t, J = 6.0 Hz, 1H), 4.52 (s, 2H), 3.89 (t, J = 5.0 Hz, 2H), 3.25 (t, J = 6.2 Hz, 2H), 2.86 (t, J = 5.4 Hz, 2H), 2.37 (s, 3H), 2.17 (s, 3H), 1.07 (m, 1H), 0.51 (d, J = 7.6 Hz, 2H), 0.24 (d, J = 4.8 Hz, 2H) |

TABLE 1-continued

Selected compounds (A-1 to A-118) of the present invention.

| Example number | structure | Compound Name | Method | MS m/z (m + 1) | 1H NMR |
|---|---|---|---|---|---|
| A-66 | 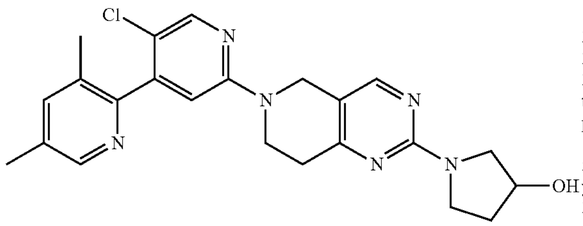 [SMILES: Cc1cnc(-c2cc(N3CCc4nc(N5CCC(O)C5)ncc4C3)ncc2Cl)c(C)c1] | 1-(6-(5'-chloro-3,5-dimethyl-2,4'-bipyridin-2'-yl)-5,6,7,8-tetrahydropyrido[4,3-d]pyrimidin-2-yl)pyrrolidin-3-ol | I | 436.8 | $^1$H NMR (400 MHz, CDCl$_3$) δ 8.34 (s, 1H), 8.23 (s, 1H), 8.12 (s, 1H), 7.42 (s, 1H), 6.64 (s, 1H), 4.57 (s, 1H), 4.51 (s, 2H), 3.89 (t, J = 5.2 Hz, 2H), 3.73-3.62 (m, 2H), 2.88 (t, J = 5.8 Hz, 2H), 2.37 (s, 3H), 2.17 (s, 3H), 2.13-2.01 (m, 2H) |
| A-67 | 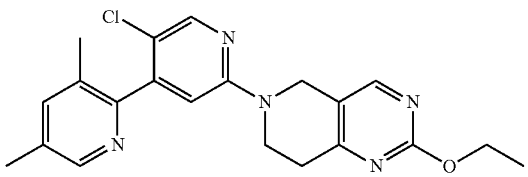 [SMILES: CCOc1ncc2c(n1)CCN(c1cc(-c3ncc(C)cc3C)c(Cl)cn1)C2] | 6-(5'-chloro-3,5-dimethyl-2,4'-bipyridin-2'-yl)-2-ethoxy-5,6,7,8-tetrahydropyrido[4,3-d]pyrimidine | I | 395.9 | $^1$H NMR (400 MHz, CDCl3) δ 8.35 (s, 1H), 8.28 (s, 1H), 8.24 (s, 1H), 7.43 (s, 1H), 6.67 (s, 1H), 4.64 (s, 2H), 4.39 (q, J = 7.2 Hz, 2H), 3.91 (s, 2H), 2.98 (t, J = 5.6 Hz, 2H), 2.37 (s, 3H), 2.17 (s, 3H), 1.42 (t, J = 7.1 Hz, 3H) |
| A-68 | 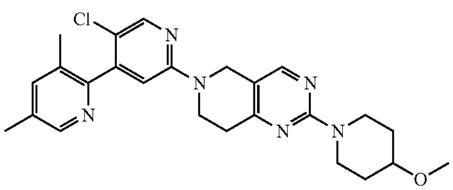 | 6-(5'-chloro-3,5-dimethyl-2,4'-bipyridin-2'-yl)-2-(4-methoxypiperidin-1-yl)-5,6,7,8-tetrahydropyrido[4,3-d]pyrimidine | I | 464.8 | $^1$H NMR (400 MHz, CDCl$_3$) δ 8.37 (s, 1H), 8.24 (s, 1H), 8.11 (s, 1H), 7.44 (s, 1H), 6.65 (s, 1H), 4.52 (s, 2H), 4.32 (d, J = 6.0 Hz, 2H), 3.90 (s, 2H), 3.45 (m, 1H), 3.40 (s, 3H), 3.38-3.34 (m, 2H), 2.87 (s, 2H), 2.38 (s, 3H), 2.18 (s, 3H), 1.93-1.93 (m, 2H), 1.61-1.54 (m, 2H) |
| A-69 | 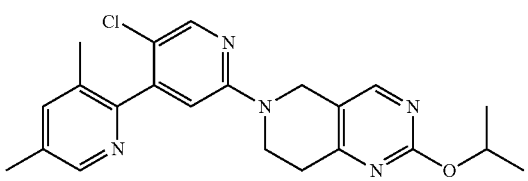 | 6-(5'-chloro-3,5-dimethyl-2,4'-bipyridin-2'-yl)-2-isopropoxy-5,6,7,8-tetrahydropyrido[4,3-d]pyrimidine | I | 409.8 | $^1$H NMR (400 MHz, CDCl$_3$) δ 8.36 (s, 1H), 8.28 (s, 1H), 8.24 (s, 1H), 7.43 (s, 1H), 6.68 (s, 1H), 5.26 (m, 1H), 4.64 (s, 2H), 3.91 (s, 2H), 2.98 (s, 2H), 2.38 (s, 3H), 2.18 (s, 3H), 1.38 (d, J = 4.4 Hz, 6H) |
| A-70 | 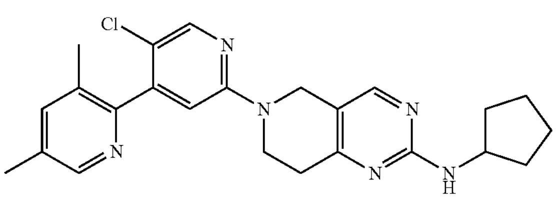 [SMILES: Cc1cnc(-c2cc(N3CCc4nc(NC5CCCC5)ncc4C3)ncc2Cl)c(C)c1] | 6-(5'-chloro-3,5-dimethyl-2,4'-bipyridin-2'-yl)-N-cyclopentyl-5,6,7,8-tetrahydropyrido[4,3-d]pyrimidin-2-amine | I | 434.8 | $^1$H NMR (400 MHz, CDCl$_3$) δ 8.33 (s, 1H), 8.21 (s, 1H), 8.07 (s, 1H), 7.40 (s, 1H), 6.62 (s, 1H), 5.13 (d, J = 8.8 Hz, 1H), 4.50 (s, 2H), 4.23 (m, 1H), 3.87 (t, J = 5.8 Hz, 2H), 2.83 (t, J = 5.8 Hz, 2H), 2.35 (s, 3H), 2.15 (s, 3H), 2.05-1.98 (m, 2H), 1.70-1.61 (m, 4H), 1.48-1.41 (m, 2H) |
| A-71 | 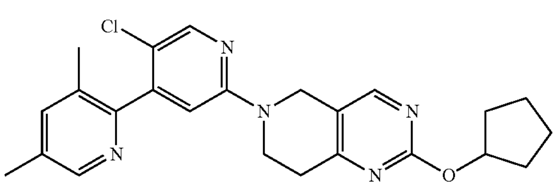 [SMILES: Cc1cnc(-c2cc(N3CCc4nc(OC5CCCC5)ncc4C3)ncc2Cl)c(C)c1] | 6-(5'-chloro-3,5-dimethyl-2,4'-bipyridin-2'-yl)-2-(cyclopentyloxy)-5,6,7,8-tetrahydropyrido[4,3-d]pyrimidine | I | 435.8 | $^1$H NMR (400 MHz, CDCl$_3$) δ 8.36 (s, 1H), 8.28 (s, 1H), 8.25 (s, 1H), 7.44 (s, 1H), 6.68 (s, 1H), 5.41 (m, 1H), 4.65 (s, 2H), 3.92 (t, J = 5.0 Hz, 2H), 2.99 (t, J = 5.6 Hz, 2H), 2.38 (s, 3H), 2.18 (s, 3H), 1.98-1.95 (m, 2H), 1.88 (s, 2H), 1.63 (s, 4H) |

TABLE 1-continued

Selected compounds (A-1 to A-118) of the present invention.

| Example number | structure | Compound Name | Method | MS m/z (m + 1) | 1H NMR |
|---|---|---|---|---|---|
| A-72 | 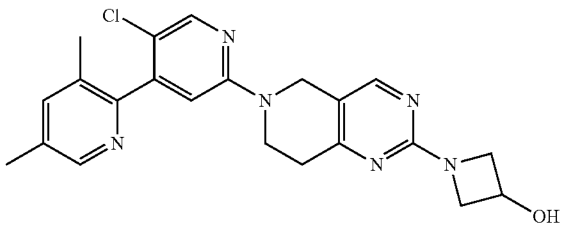 [SMILES: Cc1cnc(-c2cc(N3CCc4nc(N5CC(O)C5)ncc4C3)ncc2Cl)c(C)c1] | 1-(6-(5'-chloro-3,5-dimethyl-2,4'-bipyridin-2'-yl)-5,6,7,8-tetrahydropyrido[4,3-d]pyrimidin-2-yl)azetidin-3-ol | I | 422.8 | $^1$H NMR (400 MHz, CDCl$_3$) δ 8.35 (s, 1H), 8.24 (s, 1H), 8.13 (s, 1H), 7.43 (s, 1H), 6.65 (s, 1H), 4.86-4.67 (m, 1H), 4.54 (s, 2H), 4.39 (t, J = 8.0 Hz, 2H), 3.99-3.96 (m, 2H), 3.90 (t, J = 5.6 Hz, 2H), 2.90 (t, J = 6.0 Hz, 2H), 2.38 (s, 3H), 2.18 (s, 3H) |
| A-73 | 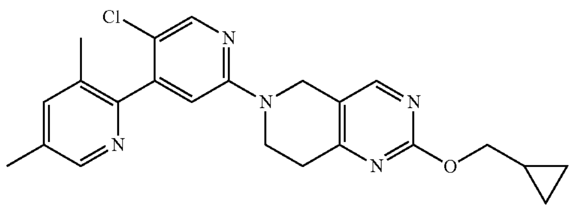 [SMILES: Cc1cnc(-c2cc(N3CCc4nc(OCC5CC5)ncc4C3)ncc2Cl)c(C)c1] | 6-(5'-chloro-3,5-dimethyl-2,4'-bipyridin-2'-yl)-2-(cyclopropylmethoxy)-5,6,7,8-tetrahydropyrido[4,3-d]pyrimidine | I | 421.9 | $^1$H NMR (400 MHz, CDCl$_3$) δ 8.36 (s, 1H), 8.29 (s, 1H), 8.25 (s, 1H), 7.44 (s, 1H), 6.68 (s, 1H), 4.65 (s, 2H), 4.18 (d, J = 7.6 Hz, 2H), 3.92 (t, J = 4.6 Hz, 2H), 2.99 (t, J = 5.6 Hz, 2H), 2.38 (s, 3H), 2.18 (s, 3H), 1.32 (m , 1H), 0.61 (d, J = 7.2 Hz, 2H), 0.37 (d, J = 4.8 Hz, 2H) |
| A-74 | 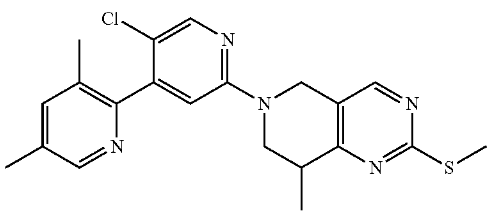 | 6-(5'-chloro-3,5-dimethyl-2,4'-bipyridin-2'-yl)-8-methyl-2-(methylthio)-5,6,7,8-tetrahydropyrido[4,3-d]-pyrimidine | K | 411.8 | $^1$H NMR (400 MHz, CDCl$_3$) δ 8.36 (s, 1H), 8.31 (s, 1H), 8.24 (s, 1H), 7.44 (s,1H), 6.67 (s, 1H), 4.63 (m, 2H), 3.99 (m, 1H), 3.58 (m, 1H), 3.12 (m, 1H), 2.57 (s, 3H), 2.38 (s, 3H), 2.18 (s, 3H), 1.38 (d, J = 5.0 Hz, 3H) |
| A-75 | 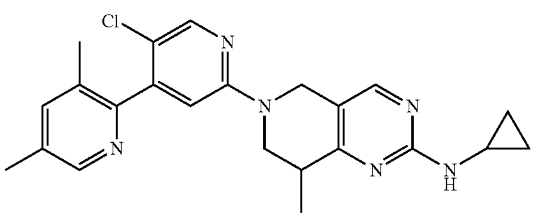 [SMILES: Cc1cnc(-c2cc(N3Cc4cnc(NC5CC5)nc4C(C)C3)ncc2Cl)c(C)c1] | 6-(5'-chloro-3,5-dimethyl-2,4'-bipyridin-2'-yl)-N-cyclopropyl-8-methyl-5,6,7,8-tetrahydropyrido[4,3-d]pyrimidin-2-amine | K | 443.8 | $^1$H NMR (400 MHz, CDCl$_3$) δ 8.34 (s, 1H), 8.22 (s, 1H), 8.15 (s, 1H), 7.42 (s, 1H), 6.63 (s, 1H), 5.21 (s, 1H), 4.53 (s, 2H), 3.92 (m, 1H), 3.59(m, 1H), 2.95 (m, 1H), 2.21 (m, 1H), 2.37 (s, 3H), 2.17 (s, 3H), 1.32 (d, J = 6.8 Hz, 3H), 0.87-079 (m, 2H), 0.58-0.52 (m, 2H) |
| A-76 | 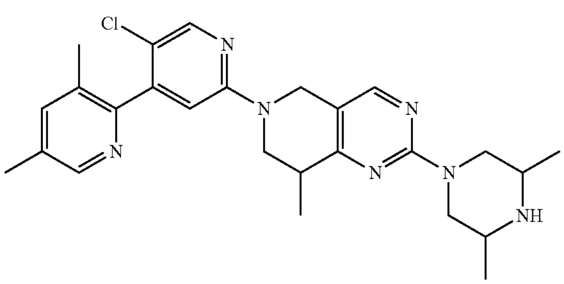 | 6-(5'-chloro-3,5-dimethyl-2,4'-bipyridin-2'-yl)-2-(3,5-dimethyl-piperazin-1-yl)-8-methyl-5,6,7,8-tetrahydropyrido[4,3-d]pyrimidine | K | 477.8 | $^1$H NMR (400 MHz, CDCl$_3$) δ 8.37 (s, 1H), 8.23 (s, 1H), 8.12 (s, 1H), 7.44 (s, 1H), 6.64 (s, 1H), 4.73 (m, 2H), 4.53 (m, 2H), 4.01 (m, 1H), 3.52(m, 1H), 3.01 (br, 3H), 2.71 (br, 2H), 2.38 (s, 3H), 2.19 (s, 3H), 1.35-1.26 (m, 9H) |
| A-77 | 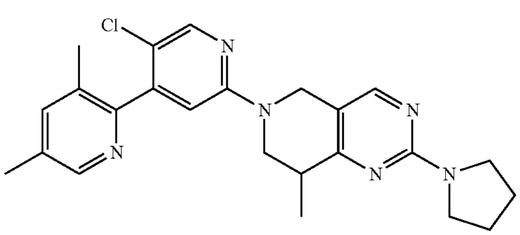 [SMILES: Cc1cnc(-c2cc(N3Cc4cnc(N5CCCC5)nc4C(C)C3)ncc2Cl)c(C)c1] | 6-(5'-chloro-3,5-dimethyl-2,4'-bipyridin-2'-yl)-8-methyl-2-(pyrrolidin-1-yl)-5,6,7,8-tetrahydropyrido[4,3-d]pyrimidine | K | 434.9 | $^1$H NMR (400 MHz, CDCl$_3$) δ 8.39 (s, 1H), 8.26 (s, 1H), 8.15 (s, 1H), 7.46 (s, 1H), 6.66 (s, 1H), 4.54 (s, 2H), 4.02 (m, 1H), 3.61-3.58 (m, 5H), 3.05 (m, 1H), 2.41 (s, 3H), 2.11 (s, 3H), 2.01-1.99 (m, 4H), 1.37 (d, J = 6.8 Hz, 3H) |

TABLE 1-continued

Selected compounds (A-1 to A-118) of the present invention.

| Example number | structure | Compound Name | Method | MS m/z (m + 1) | 1H NMR |
|---|---|---|---|---|---|
| A-78 | 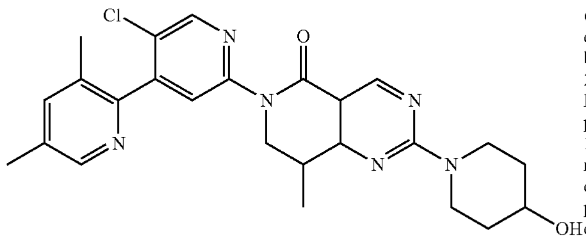 [SMILES: Cc1cnc(-c2cc(N3CC(C)C4N=C(N5CCC(O)CC5)N=CC4C3=O)ncc2Cl)c(C)c1] | 6-(5'-chloro-3,5-dimethyl-2,4'-bipyridin-2'-yl)-2-(4-hydroxy-piperidin-1-yl)-8-methyl-7,8-dihydro-pyrido[4,3-d]pyrimidin-5(6H)-one | K | 478.8 | $^1$H NMR (400 MHz, CDCl$_3$) δ 8.89 (s, 1H), 8.47 (s, 1H), 8.34 (s, 1H), 8.01 (s, 1H), 7.44 (s, 1H), 4.52-4.48 (m, 2H), 4.42-4.38 (m, 1H), 4.02-4.00 (m, 2H), 3.55-3.50 (m, 1H), 3.12-3.10 (m, 1H), 2.37 (s, 3H), 2.23 (s, 3H), 1.97 (m, 2H), 1.62 (m, 2H), 1.39 (d, J = 6.8 Hz, 3H) |
| A-79 | 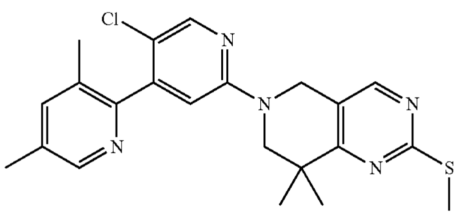 | 6-(5'-chloro-3,5-dimethyl-2,4'-bipyridin-2'-yl)-8,8-dimethyl-2-(methylthio)-5,6,7,8-tetrahydro-pyrido-[4,3-d]pyrimidine | K | 425.8 | $^1$H NMR (400 MHz, CDCl3) δ 8.37 (s, 1H), 8.30 (s, 1H), 8.24 (s, 1H), 7.45 (s, 1H), 6.68 (s, 1H), 4.62 (s, 2H), 3.68 (s, 2H), 2.57 (s, 3H), 2.39 (s, 3H), 2.19 (s, 3H), 1.34 (s, 6H) |
| A-80 | 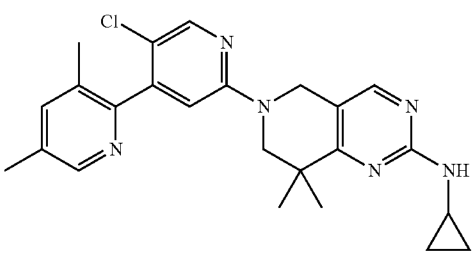 [SMILES: Cc1cnc(-c2cc(N3Cc4cnc(NC5CC5)nc4C(C)(C)C3)ncc2Cl)c(C)c1] | 6-(5'-chloro-3,5-dimethyl-2,4'-bipyridin-2'-yl)-N-cyclopropyl-8,8-dimethyl-5,6,7,8-tetrahydro-pyrido-[4,3-d]pyrimidin-2-amine | K | 434.8 | $^1$H NMR (400 MHz, CDCl$_3$) δ 8.36 (s, 1H), 8.24 (s, 1H), 8.19 (s, 1H), 7.44 (s, 1H), 6.64 (s, 1H), 5.38 (s, 1H), 4.53 (s, 2H), 3.65 (s, 2H), 2.68 (m, 1H), 2.38 (s, 3H), 2.19 (s, 3H), 1.30 (s, 6H), 0.81 (m, 2H), 0.55 (m, 2H) |
| A-81 | 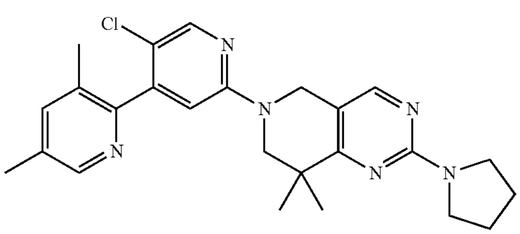 [SMILES: Cc1cnc(-c2cc(N3Cc4cnc(N5CCCC5)nc4C(C)(C)C3)ncc2Cl)c(C)c1] | 6-(5'-chloro-3,5-dimethyl-2,4'-bipyridin-2'-yl)-8,8-dimethyl-2-(pyrrolidin-1-yl)-5,6,7,8-tetrahydro-pyrido-[4,3-d]pyrimidine | K | 448.8 | $^1$H NMR (400 MHz, CDCl$_3$) δ 8.36 (s, 1H), 8.23 (s, 1H), 8.10 (s, 1H), 7.43 (s, 1H), 6.63 (s, 1H), 4.50 (s, 2H), 3.66 (br s, 2H), 3.58 (br, 4H), 2.38 (s, 3H), 2.19 (s, 3H), 1.98 (m, 4H), 1.31 (s, 6H) |
| A-82 | 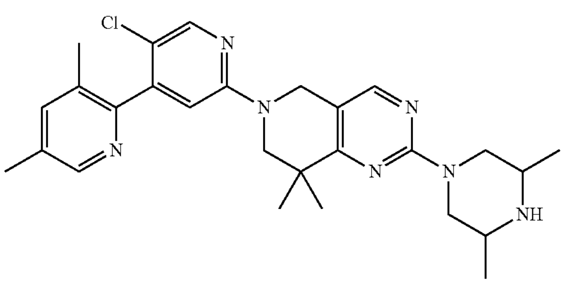 | 6-(5'-chloro-3,5-dimethyl-2,4'-bipyridin-2'-yl)-2-(3,5-dimethyl-piperazin-1-yl)-8,8-dimethyl-5,6,7,8-tetrahydro-pyrido-[4,3-d]pyrimidine | K | 491.8 | $^1$H NMR (400 MHz, CDCl$_3$) δ 8.36 (s, 1H), 8.23 (s, 1H), 8.12 (s, 1H), 7.44 (s, 1H), 6.64 (s, 1H), 4.80-4.77(m, 2H), 4.53 (br, 2H), 3.66 (s, 2H), 3.14 (br, 2H), 2.89 (m, 2H), 2.38 (s, 3H), 2.19 (s, 3H), 1.47 (d, J = 5.2 Hz, 6H), 1.31 (s, 6H) |

TABLE 1-continued

Selected compounds (A-1 to A-118) of the present invention.

| Example number | structure | Compound Name | Method | MS m/z (m + 1) | 1H NMR |
|---|---|---|---|---|---|
| A-83 | 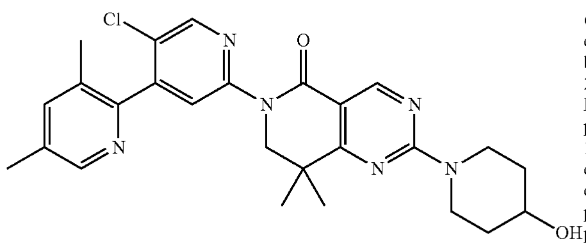 | 6-(5'-chloro-3,5-dimethyl-2,4'-bipyridin-2'-yl)-2-(4-hydroxy-piperidin-1-yl)-8,8-dimethyl-7,8-dihydro-pyrido[4,3-d]pyrimidin-5(6H)-one | K | 492.8 | $^1$H NMR (400 MHz, CDCl$_3$) δ 8.99 (s, 1H), 8.46 (s, 1H), 8.34 (s, 1H), 8.09 (s, 1H), 7.44 (s, 1H), 4.51-4.48 (m, 2H), 4.07 (s, 2H), 4.01(br s, 1H), 3.51 (t, J = 6.4 Hz, 2H), 2.37 (s, 3H), 2.23 (s, 3H), 1.99-1.97 (m, 2H), 1.59-1.57(m, 2H), 1.35 (s, 6H) |
| A-84 | 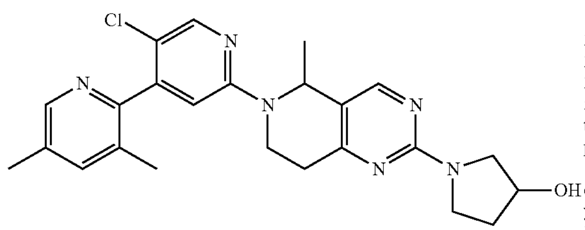 [SMILES: Cc1cnc(-c2cc(N3CCc4nc(N5CCC(O)C5)ncc4C3C)ncc2Cl)c(C)c1] | 1-(6-(5'-chloro-3,5-dimethyl-2,4'-bipyridin-2'-yl)-5-methyl-5,6,7,8-tetrahydro-pyrido[4,3-d]pyrimidin-2-yl)pyrrolidin-3-ol | N | 451.3 | $^1$H NMR (400 MHz, CDCl$_3$) δ 8.35 (s, 1H), 8.21 (s, 1H), 8.13 (s, 1H), 7.42 (s, 1H), 6.61 (s, 1H), 5.40-5.33 (m, 1H), 4.63-4.56 (m, 1H), 4.38-4.31 (m, 1H), 3.77-3.63 (m, 4H), 3.46-3.35 (m, 1H), 2.98-2.86 (m, 1H), 2.82-2.73 (m, 1H), 2.37 (s, 3H), 2.18 (s, 3H), 2.15-2.01 (m, 2H), 1.42 (d, J = 6.4 Hz, 3H) |
| A-85 | 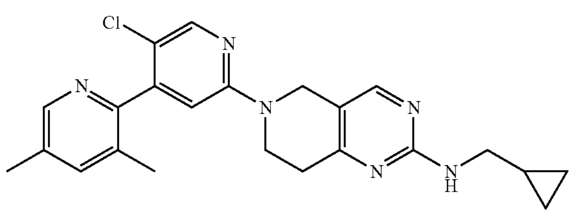 [SMILES: Cc1cnc(-c2cc(N3CCc4nc(NCC5CC5)ncc4C3)ncc2Cl)c(C)c1] | 6-(5'-chloro-3,5-dimethyl-2,4'-bipyridin-2'-yl)-N-(cyclopropylmethyl)-5-methyl-5,6,7,8-tetrahydro-pyrido[4,3-d]pyrimidin-2-amine | N | 435.3 | $^1$H NMR (400 MHz, CDCl$_3$) δ 8.35 (s, 1H), 8.21 (s, 1H), 8.08 (s, 1H), 7.43 (s, 1H), 6.60 (s, 1H), 5.44-5.36 (m, 1H), 5.15-5.09 (m, 1H), 4.39-4.32 (m, 1H), 3.45-3.36 (m, 1H), 3.27-3.24 (m, 2H), 2.94-2.84 (m, 1H), 2.69-2.78 (m, 1H), 2.37 (s, 3H), 2.18 (s, 3H), 1.43 (d, J = 6.4 Hz, 3H), 1.12-1.04 (m, 1H), 0.55-0.50 (m, 2H), 0.27-0.21 (m, 2H) |
| A-86 | 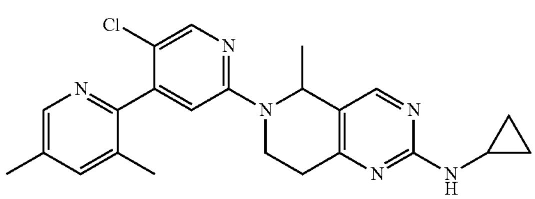 [SMILES: Cc1cnc(-c2cc(N3CCc4nc(NC5CC5)ncc4C3C)ncc2Cl)c(C)c1] | 6-(5'-chloro-3,5-dimethyl-2,4'-bipyridin-2'-yl)-N-cyclopropyl-5-methyl-5,6,7,8-tetrahydro-pyrido[4,3-d]pyrimidin-2-amine | N | 421.2 | $^1$H NMR (400 MHz, CDCl$_3$) δ 8.35 (s, 1H), 8.21 (s, 1H), 8.16 (s, 1H), 7.43 (s, 1H), 6.61 (s, 1H), 5.44-5.36 (m, 1H), 5.25 (br s, 1H), 4.41-4.32 (m, 1H), 3.46-3.37 (m, 1H), 2.97-2.85 (m, 1H), 2.80-2.71 (m, 2H), 2.38 (s, 3H), 2.18 (s, 3H), 1.44 (d, J = 6.4 Hz, 3H), 0.84-0.80 (m, 2H), 0.55-0.50 (m, 2H) |
| A-87 | 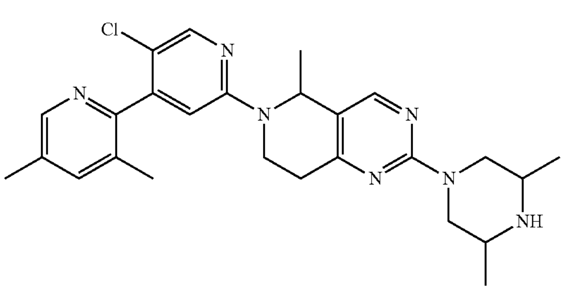 | 6-(5'-chloro-3,5-dimethyl-2,4'-bipyridin-2'-yl)-2-(3,5-dimethyl-piperazin-1-yl)-5-methyl-5,6,7,8-tetrahydro-pyrido[4,3-d]pyrimidine | N | 478.3 | $^1$H NMR (400 MHz, CDCl$_3$) δ 8.35 (s, 1H), 8.21 (s, 1H), 8.13 (s, 1H), 7.43 (s, 1H), 6.61 (s, 1H), 5.44-5.36 (m, 1H), 4.87 (d, J = 12.5 Hz, 2H), 4.41-4.30 (m, 1H), 3.44-3.35 (m, 1H), 3.32-3.21 (m, 2H), 3.18 (d, J = 13.4 Hz, 2H), 2.96-2.85 (m, 1H), 2.80-2.71 (m, 1H), 2.38 (s, 3H), 2.18 (s, 3H), 1.64 (d, J = 6.1 Hz, 6H), 1.44 (d, J = 6.6 Hz, 3H) |

TABLE 1-continued

Selected compounds (A-1 to A-118) of the present invention.

| Example number | structure | Compound Name | Method | MS m/z (m + 1) | 1H NMR |
|---|---|---|---|---|---|
| A-88 | 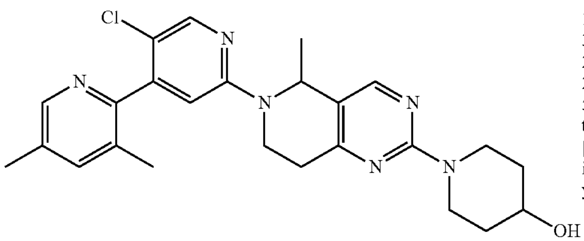 | 1-(6-(5'-chloro-3,5-dimethyl-2,4'-bipyridin-2'-yl)-5-methyl-5,6,7,8-tetrahydropyrido[4,3-d]pyrimidin-2-yl)piperidin-4-ol | N | 465.2 | $^1$H NMR (400 MHz, CDCl$_3$) δ 8.35 (s, 1H), 8.21 (s, 1H), 8.10 (s, 1H), 7.43 (s, 1H), 6.60 (s, 1H), 5.44-5.31 (m, 1H), 4.45-4.37 (m, 2H), 4.38-4.30 (m, 1H), 3.96-3.90 (m, 1H), 3.45-3.35 (m, 1H), 3.32-3.23 (m, 2H), 2.93-2.84 (m, 1H), 2.80-2.70 (m, 1H), 2.38 (s, 3H), 2.18 (s, 3H), 1.99-1.90 (m, 2H), 1.51-1.46 (m, 2H), 1.42 (d, J = 6.8 Hz, 3H) |
| A-89 | 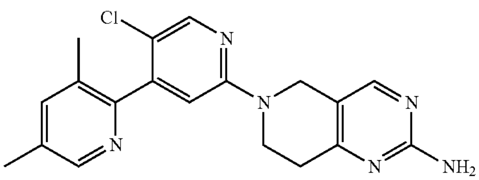 [SMILES: Cc1cnc(-c2cc(N3CCc4nc(N)ncc4C3)ncc2Cl)c(C)c1] | 6-(5'-chloro-3,5-dimethyl-2,4'-bipyridin-2'-yl)-5,6,7,8-tetrahydropyrido[4,3-d]pyrimidin-2-amine | J | 366.8 | $^1$H NMR (400 MHz, CDCl$_3$) δ 8.35 (s, 1H), 8.23 (s, 2H), 8.10 (s, 1H), 7.43 (s, 1H), 6.65 (s, 1H), 4.94 (s, 2H), 4.56 (s, 2H), 3.90 (t, J = 5.8 Hz, 2H), 2.87 (t, J = 5.8 Hz, 2H), 2.37 (s, 3H), 2.17 (s, 3H) |
| A-90 | 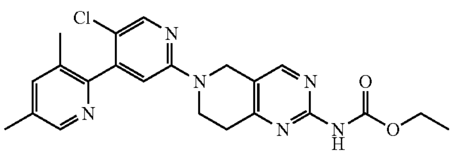 [SMILES: CCOC(=O)Nc1ncc2c(n1)CCN(c1cc(-c3ncc(C)cc3C)c(Cl)cn1)C2] | ethyl 6-(5'-chloro-3,5-dimethyl-2,4'-bipyridin-2'-yl)-5,6,7,8-tetrahydropyrido[4,3-d]pyrimidin-2-ylcarbamate | J | 439.0 | $^1$H NMR (400 MHz, CDCl$_3$) δ 8.40 (s, 1H), 8.35 (s, 1H), 8.24 (s, 1H), 7.60 (s, 1H), 7.43 (s, 1H), 6.68 (s, 1H), 4.66 (s, 2H), 4.28 (m, 2H), 3.93 (s, 2H), 3.02 (s, 2H), 2.38 (s, 3H), 2.17 (s, 3H), 1.32 (t, J = 7.0 Hz, 3H) |
| A-91 | 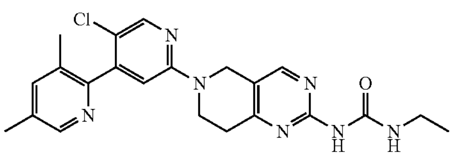 | 1-(6-(5'-chloro-3,5-dimethyl-2,4'-bipyridin-2'-yl)-5,6,7,8-tetrahydropyrido[4,3-d]pyrimidin-2-yl)-3-ethylurea | J | 438.1 | $^1$H NMR (400 MHz, CDCl$_3$) δ 8.92 (s, 1H), 8.36 (s, 1H), 8.26 (s, 1H), 8.25 (s, 1H), 7.45 (s, 1H), 7.30 (s, 1H), 6.69 (s, 1H), 4.65 (s, 2H), 3.93 (s, 2H), 3.41 (t, J = 6.4 Hz, 2H), 2.98 (d, J = 2.6 Hz, 2H), 2.39 (s, 3H), 2.18 (s, 3H), 1.24 (t, J = 7.0 Hz, 3H) |
| A-92 | 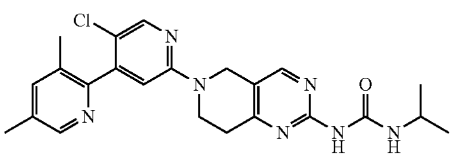 [SMILES: Cc1cnc(-c2cc(N3CCc4nc(NC(=O)NC(C)C)ncc4C3)ncc2Cl)c(C)c1] | 1-(6-(5'-chloro-3,5-dimethyl-2,4'-bipyridin-2'-yl)-5,6,7,8-tetrahydropyrido[4,3-d]pyrimidin-2-yl)-3-isopropylurea | J | 452.0 | $^1$H NMR (300 MHz, CDCl$_3$) δ 8.87 (s, 1H), 8.35 (s, 1H), 8.28 (s, 1H), 8.24 (s, 1H), 7.44 (s, 1H), 7.39 (s, 1H), 6.68 (s, 1H), 4.64 (s, 2H), 4.08 (m, 1H), 3.93 (t, J = 5.7 Hz, 2H), 2.96 (t, J = 5.4 Hz, 2H), 2.38 (s, 3H), 2.18 (s, 3H), 1.26 (d, J = 3 Hz, 6H) |
| A-93 | 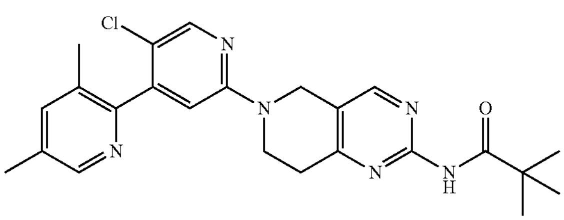 [SMILES: Cc1cnc(-c2cc(N3CCc4nc(NC(=O)C(C)(C)C)ncc4C3)ncc2Cl)c(C)c1] | N-(6-(5'-chloro-3,5-dimethyl-2,4'-bipyridin-2'-yl)-5,6,7,8-tetrahydropyrido[4,3-d]pyrimidin-2-yl)pivalamide | J | 451.2 | $^1$H NMR (300 MHz, CDCl$_3$) δ 8.70 (s, 1H), 8.27 (s, 1H), 8.22 (s, 1H), 7.83 (d, J = 8.1 Hz, 1H), 7.43-7.39 (m, 1H), 6.64 (s, 1H), 5.74 (br s, 1H), 4.59 (s, 2H), 3.93 (t, J = 11.2 Hz, 2H), 2.94 (t, J = 11.7 Hz, 2H), 2.82-2.76 (m, 1H), 0.87-0.81 (m, 2H), 0.59-0.54 (m, 2H) |
| A-94 | 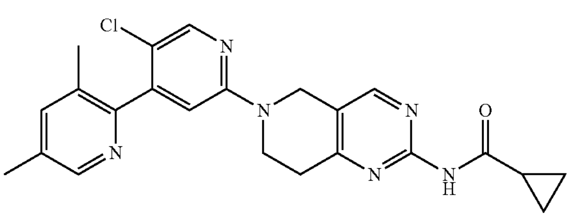 [SMILES: Cc1cnc(-c2cc(N3CCc4nc(NC(=O)C5CC5)ncc4C3)ncc2Cl)c(C)c1] | N-(6-(5'-chloro-3,5-dimethyl-2,4'-bipyridin-2'-yl)-5,6,7,8-tetrahydropyrido[4,3-d]pyrimidin-2-yl)cyclopropane carboxamide | J | 435.0 | $^1$H NMR (400 MHz, CDCl$_3$) δ8.40 (s, 1H), 8.35 (s, 1H), 8.24 (s, 1H), 8.14 (s, 1H), 7.43 (s, 1H), 6.68 (s, 1H), 4.67 (s, 2H), 3.93 (t, J = 5.4 Hz, 2H), 3.02 (t, J = 6.0 Hz, 2H), 2.38 (s, 3H), 2.17 (s, 3H), 1.33 (s, 1H), 1.18-1.16 (m, 2H), 0.95-0.90 (m, 2H) |

TABLE 1-continued

Selected compounds (A-1 to A-118) of the present invention.

| Example number | structure | Compound Name | Method | MS m/z (m + 1) | 1H NMR |
|---|---|---|---|---|---|
| A-95 | 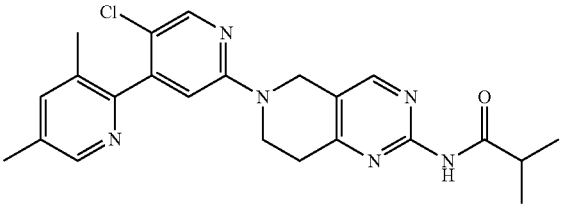 [SMILES: Cc1cnc(-c2cc(N3CCc4nc(NC(=O)C(C)C)ncc4C3)ncc2Cl)c(C)c1] | N-(6-(5'-chloro-3,5-dimethyl-2,4'-bipyridin-2'-yl)-5,6,7,8-tetrahydropyrido[4,3-d]pyrimidin-2-yl)isobutyramide | J | 437.2 | $^1$H NMR (400 MHz, CDCl$_3$) δ 8.40 (s, 1H), 8.35 (s, 1H), 8.24 (s, 1H), 7.88 (s, 1H), 7.43 (s, 1H), 6.68 (s, 1H), 4.67 (s, 2H), 3.93 (t, J = 5.6 Hz, 2H), 3.02 (t, J = 5.8 Hz, 2H), 2.38 (s, 3H), 2.17 (s, 3H), 1.33 (s, 1H), 1.27(s, 6H) |
| A-96 | 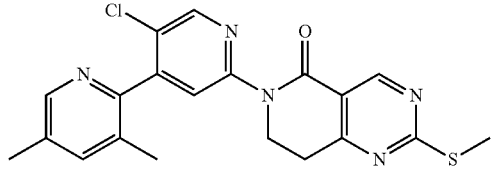 | 6-(5'-chloro-3,5-dimethyl-2,4'-bipyridin-2'-yl)-2-(methylthio)-7,8-dihydropyrido[4,3-d]pyrimidin-5(6H)-one | L | 411.8 | $^1$H NMR (400 MHz, CDCl$_3$) δ 9.07 (s, 1H), 8.49 (s, 1H), 8.35 (s, 1H), 8.04 (s, 1H), 7.45 (s, 1H), 4.40 (t, J = 6.4 Hz, 2H), 3.20 (t, J = 6.4 Hz, 2H), 2.63 (s, 3H), 2.38 (s, 3H), 2.23 (s, 3H) |
| A-97 | 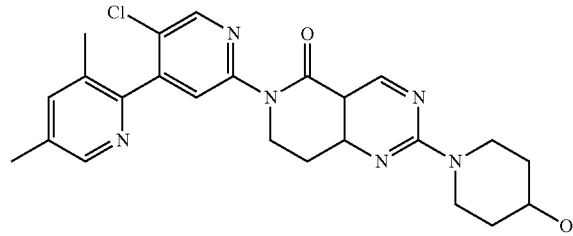 | 6-(5'-chloro-3,5-dimethyl-2,4'-bipyridin-2'-yl)-2-(4-hydroxypiperidin-1-yl)-7,8-dihydropyrido[4,3-d]pyrimidin-5(6H)-one | M | 464.8 | $^1$H NMR (400 MHz, CDCl$_3$) δ 8.89 (s, 1H), 8.46 (s, 1H), 8.34 (s, 1H), 8.02 (s, 1H), 7.44 (s, 1H), 4.51-4.44 (m, 2H), 4.32 (t, J = 6.6 Hz, 2H), 4.02 (m, 1H), 3.56-3.49 (m, 2H), 3.02 (t, J = 6.2 Hz, 2H), 2.37 (s, 3H), 2.23 (s, 3H), 2.01-1.95 (m, 2H), 1.63-1.61 (m, 2H) |
| A-98 | 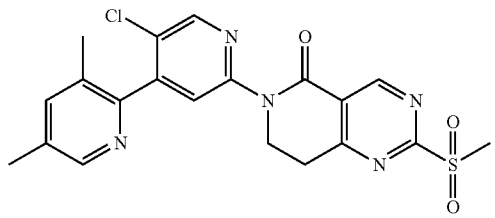 | 6-(5'-chloro-3,5-dimethyl-2,4'-bipyridin-2'-yl)-2-(methylsulfonyl)-7,8-dihydropyrido[4,3-d]pyrimidin-5(6H)-one | L | 443.7 | $^1$H NMR (400 MHz, CDCl$_3$) δ 9.44 (s, 1H), 8.52 (s, 1H), 8.36 (s, 1H), 8.06 (s, 1H), 7.47 (s, 1H), 4.51 (t, J = 6.4 Hz, 2H), 3.45 (t, J = 6.6 Hz, 2H), 3.42 (s, 3H), 2.39 (s, 3H), 2.23 (s, 3H) |
| A99 | 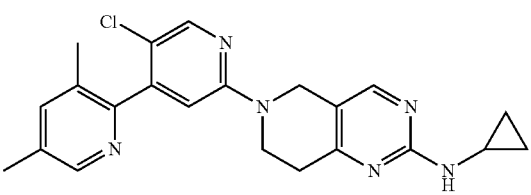 [SMILES: Cc1cnc(-c2cc(N3CCc4nc(NC5CC5)ncc4C3)ncc2Cl)c(C)c1] | 6-(5'-chloro-3,5-dimethyl-2,4'-bipyridin-2'-yl)-2-(cyclopropylamino)-7,8-dihydropyrido[4,3-d]pyrimidin-5(6H)-one | M | 420.9 | $^1$H NMR (400 MHz, CDCl$_3$) δ 8.95 (s, 1H), 8.47 (s, 1H), 8.34 (s, 1H), 8.03 (s, 1H), 7.44 (s, 1H), 5.74 (s, 1H), 4.34 (t, J = 6.2 Hz, 2H), 3.06 (s, 2H), 2.90 (m, 1H), 2.37 (s, 3H), 2.23 (s, 3H), 0.92-0.87 (m, 2H), 0.63-0.59 (m, 2H) |
| A-100 | 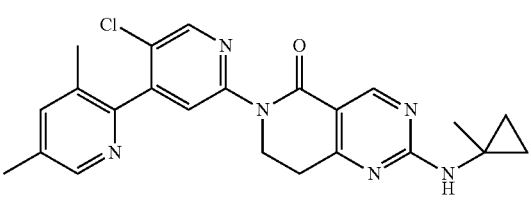 [SMILES: Cc1cnc(-c2cc(N3CCc4nc(NC5(C)CC5)ncc4C3=O)ncc2Cl)c(C)c1] | 6-(5'-chloro-3,5-dimethyl-2,4'-bipyridin-2'-yl)-2-(1-methylcyclopropylamino)-7,8-dihydropyrido[4,3-d]pyrimidin-5(6H)-one | M | 435.1 | $^1$H NMR (400 MHz, CDCl$_3$) δ 8.93 (d, J = 82.4 Hz, 1H), 8.46 (s, 1H), 8.34 (s, 1H), 8.02 (s, 1H), 7.44 (s, 1H), 5.94 (s, 1H), 4.33 (t, J = 6.4 Hz, 2H), 3.03 (d, J = 48.4 Hz, 2H), 2.37 (s, 3H), 2.23 (s, 3H), 1.48 (s, 3H), 0.84 (s, 2H), 0.77 (s, 2H) |

TABLE 1-continued

Selected compounds (A-1 to A-118) of the present invention.

| Example number | structure | Compound Name | Method | MS m/z (m + 1) | 1H NMR |
|---|---|---|---|---|---|
| A-101 | 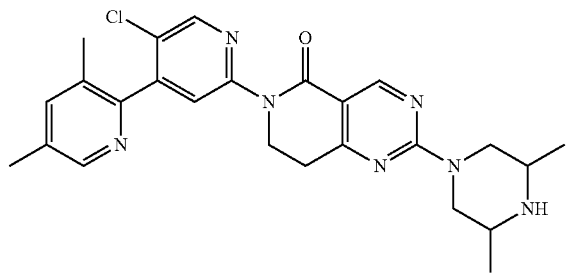 | 6-(5'-chloro-3,5-dimethyl-2,4'-bipyridin-2'-yl)-2-(3,5-dimethyl-piperazin-1-yl)-7,8-dihydro-pyrido[4,3-d]pyrimidin-5(6H)-one | M | 478.0 | $^1$H NMR (400 MHz, CDCl$_3$) δ 8.89 (s, 1H), 8.46 (s, 1H), 8.33 (s, 1H), 8.02 (s, 1H), 7.43 (s, 1H), 4.83 (d, J = 12.0 Hz, 2H), 4.32 (t, J = 6.4 Hz, 2H), 3.02 (t, J = 6.4 Hz, 2H), 2.89 (s, 2H), 2.54 (t, J = 11.8 Hz, 2H), 2.37 (s, 3H), 2.23 (s, 3H), 1.17 (d, J = 6.0 Hz, 6H) |
| A-102 | 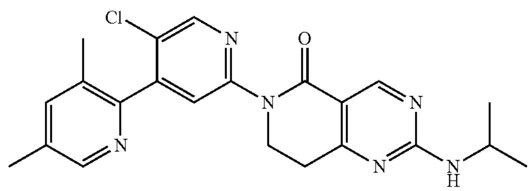 [SMILES: Cc1cnc(-c2cc(N3CCc4nc(NC(C)C)ncc4C3=O)ncc2Cl)c(C)c1] | 6-(5'-chloro-3,5-dimethyl-2,4'-bipyridin-2'-yl)-2-(isopropylamino)-7,8-dihydro-pyrido[4,3-d]pyrimidin-5(6H)-one | M | 423.1 | $^1$H NMR (400 MHz, CDCl$_3$) δ 8.90 (d, J = 28.8 Hz, 1H), 8.46 (s, 1H), 8.34 (s, 1H), 8.01 (s, 1H), 7.44 (s, 1H), 5.42 (s, 1H), 4.32 (t, J = 6.4 Hz, 2H), 4.26 (m, 1H), 3.02 (s, 2H), 2.37 (s, 3H), 2.23 (s, 3H), 1.27 (d, J = 6.5 Hz, 6H) |
| A-103 | 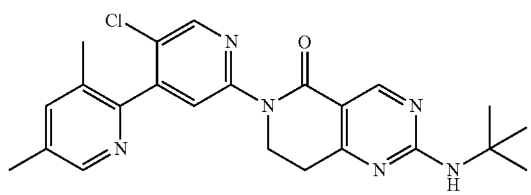 [SMILES: Cc1cnc(-c2cc(N3CCc4nc(NC(C)(C)C)ncc4C3=O)ncc2Cl)c(C)c1] | 2-(tert-butylamino)-6-(5'-chloro-3,5-dimethyl-2,4'-bipyridin-2'-yl)-7,8-dihydro-pyrido[4,3-d]pyrimidin-5(6H)-one | M | 437.2 | $^1$H NMR (400 MHz, CDCl$_3$) δ 8.85 (s, 1H), 8.44 (s, 1H), 8.32 (s, 1H), 7.98 (s, 1H), 7.41 (s, 1H), 5.59 (s, 1H), 4.30 (t, J = 6.4 Hz, 2H), 2.97 (s, 2H), 2.35 (s, 3H), 2.21 (s, 3H), 1.46 (s, 9H) |
| A-104 | 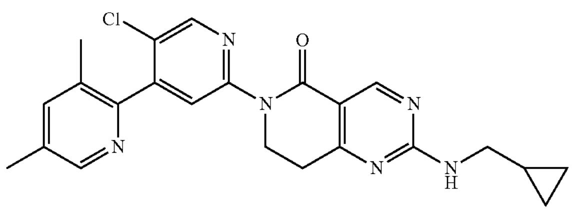 [SMILES: Cc1cnc(-c2cc(N3CCc4nc(NCC5CC5)ncc4C3=O)ncc2Cl)c(C)c1] | 6-(5'-chloro-3,5-dimethyl-2,4'-bipyridin-2'-yl)-2-(cyclopropylmethylamino)-7,8-dihydro-pyrido[4,3-d]pyrimidin-5(6H)-one | M | 435.1 | $^1$H NMR (400 MHz, CDCl$_3$) δ 8.89 (d, J = 23.6 Hz, 1H), 8.47 (s, 1H), 8.34 (s, 1H), 8.01 (s, 1H), 7.44 (s, 1H), 5.71 (s, 1H), 4.33 (t, J = 6.2 Hz, 2H), 3.36 (t, J = 6.0 Hz, 2H), 3.04 (s, 2H), 2.37 (s, 3H), 2.23 (s, 3H), 1.10 (m, 1H), 0.59-0.55 (m, 2H), 0.30-0.26 (m, 2H) |
| A-105 | 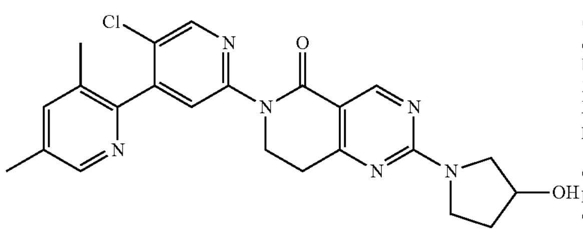 [SMILES: Cc1cnc(-c2cc(N3CCc4nc(N5CCC(O)C5)ncc4C3=O)ncc2Cl)c(C)c1] | 6-(5'-chloro-3,5-dimethyl-2,4'-bipyridin-2'-yl)-2-(3-hydroxy-pyrrolidin-1-yl)-7,8-dihydro-pyrido[4,3-d]pyrimidin-5(6H)-one | M | 450.9 | $^1$H NMR (400 MHz, CDCl$_3$) δ 8.93 (s, 1H), 8.46 (s, 1H), 8.34 (s, 1H), 8.03 (s, 1H), 7.44 (s, 1H), 4.64 (m, 1H), 4.32 (t, J = 6.4 Hz, 2H), 3.90-3.79 (m, 2H), 3.77 (s, 2H), 3.04 (t, J = 6.4 Hz, 2H), 2.37 (s, 3H), 2.23 (s, 3H), 2.17-2.06 (m, 2H) |
| A-106 | 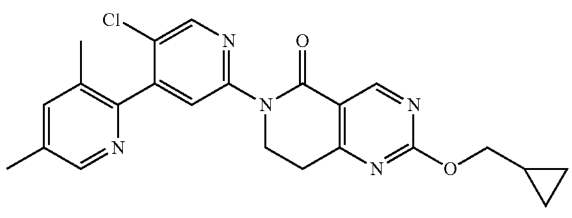 | 6-(5'-chloro-3,5-dimethyl-2,4'-bipyridin-2'-yl)-2-(cyclopropylmethoxy)-7,8-dihydro-pyrido[4,3-d]pyrimidin-5(6H)-one | M | 436.1 | $^1$H NMR (400 MHz, CDCl$_3$) δ 9.09 (s, 1H), 8.48 (s, 1H), 8.35 (s, 1H), 8.03 (s, 1H), 7.45 (s, 1H), 4.39 (t, J = 6.4 Hz, 2H), 4.30 (d, J = 7.2 Hz, 2H), 3.18 (t, J = 6.4 Hz, 2H), 2.38 (s, 3H), 2.23 (s, 3H), 0.88 (m, 1H), 0.64 (d, J = 6.4 Hz, 2H), 0.40 (d, J = 5.6 Hz, 2H) |

TABLE 1-continued

Selected compounds (A-1 to A-118) of the present invention.

| Example number | structure | Compound Name | Method | MS m/z (m + 1) | 1H NMR |
|---|---|---|---|---|---|
| A-107 | 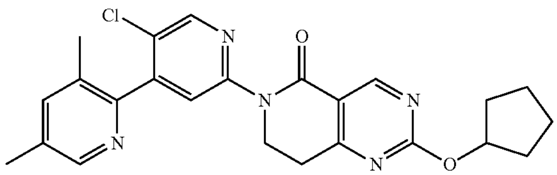 [SMILES: Cc1cnc(-c2cc(N3CCc4nc(OC5CCCC5)ncc4C3=O)ncc2Cl)c(C)c1] | 6-(5'-chloro-3,5-dimethyl-2,4'-bipyridin-2'-yl)-2-(cyclopentyloxy)-7,8-dihydropyrido[4,3-d]pyrimidin-5(6H)-one | M | 450.0 | $^1$H NMR (400 MHz, CDCl$_3$) δ 9.09 (s, 1H), 8.49 (s, 1H), 8.35 (s, 1H), 8.02 (s, 1H), 7.45 (s, 1H), 5.54 (s, 1H), 4.38 (t, J = 6.6 Hz, 2H), 3.17 (t, J = 6.4 Hz, 2H), 2.38 (s, 3H), 2.23 (s, 3H), 2.05-1.99 (m, 2H), 1.93 (s, 2H), 1.89-1.82 (m, 2H), 1.70 (s, 2H) |
| A-108 | 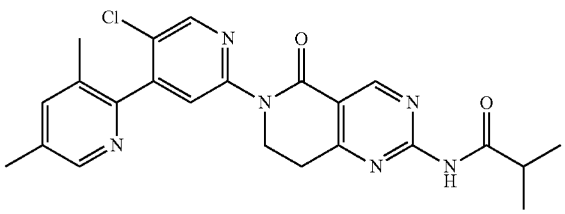 [SMILES: Cc1cnc(-c2cc(N3CCc4nc(NC(=O)C(C)C)ncc4C3=O)ncc2Cl)c(C)c1] | N-(6-(5'-chloro-3,5-dimethyl-2,4'-bipyridin-2'-yl)-5-oxo-5,6,7,8-tetrahydropyrido[4,3-d]pyrimidin-2-yl)isobutyramide | L | 451.1 | $^1$H NMR (400 MHz, CDCl$_3$) δ 9.17 (s, 1H), 8.71 (s, 1H), 8.49 (s, 1H), 8.35 (s, 1H), 8.05 (s, 1H), 7.46 (s, 1H), 4.40 (t, J = 6.6 Hz, 2H), 3.24 (t, J = 6.6 Hz, 2H), 3.06 (m, 1H), 2.38 (s, 3H), 2.23 (s, 3H), 1.28 (d, J = 6.8 Hz, 6H) |
| A-109 | 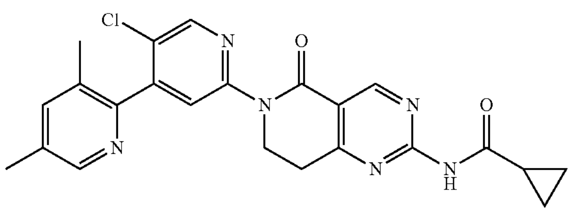 [SMILES: Cc1cnc(-c2cc(N3CCc4nc(NC(=O)C5CC5)ncc4C3=O)ncc2Cl)c(C)c1] | N-(6-(5'-chloro-3,5-dimethyl-2,4'-bipyridin-2'-yl)-5-oxo-5,6,7,8-tetrahydropyrido[4,3-d]pyrimidin-2-yl)cyclopropanecarboxamide | L | 449.2 | $^1$H NMR (400 MHz, CDCl$_3$) δ 9.17 (s, 1H), 8.51 (s, 1H), 8.47 (s, 1H), 8.37 (s, 1H), 8.06 (s, 1H), 7.47 (s, 1H), 4.43 (t, J = 6.6 Hz, 2H), 3.25 (t, J = 6.6 Hz, 2H), 2.44 (m, 1H), 2.40 (s, 3H), 2.25 (s, 3H), 1.26-1.22 (m, 2H), 1.04-0.99 (m, 2H) |
| A-110 | 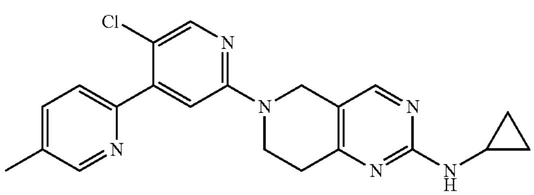 [SMILES: Cc1ccc(-c2cc(N3CCc4nc(NC5CC5)ncc4C3)ncc2Cl)nc1] | 6-(5'-chloro-5-methyl-2,4'-bipyridin-2'-yl)-N-cyclopropyl-5,6,7,8-tetrahydropyrido[4,3-d]pyrimidin-2-amine | O | 392.8 | $^1$H NMR (400 MHz, CDCl$_3$) δ 8.54 (s, 1H), 8.25 (s, 1H), 8.18 (s, 1H), 7.64-7.59 (m, 2H), 6.96 (s, 1H), 5.82 (br s, 1H), 4.58 (s, 2H), 3.92 (t, J = 5.6 Hz, 2H), 2.88 (t, J = 5.6 Hz, 2H), 2.77 (br s, 1H), 2.42 (s, 3H), 0.81 (s, 2H), 0.54 (s, 2H) |
| A-111 | 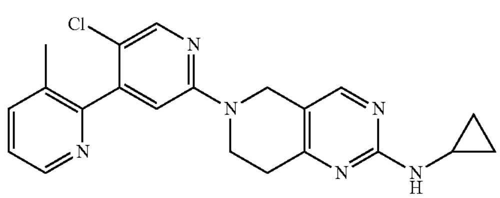 [SMILES: Cc1cccnc1-c1cc(N2CCc3nc(NC4CC4)ncc3C2)ncc1Cl] | 6-(5'-chloro-3-methyl-2,4'-bipyridin-2'-yl)-N-cyclopropyl-5,6,7,8-tetrahydropyrido[4,3-d]pyrimidin-2-amine | O | 392.8 | $^1$H NMR (400 MHz, CDCl$_3$) δ 8.53 (d, J = 4.4 Hz, 1H), 8.25 (s, 1H), 8.17 (s, 1H), 7.62 (d, J = 7.6 Hz, 1H), 7.29-7.28 (m, 1H), 5.28 (s, 1H), 4.56 (s, 2H), 3.99-3.83 (m, 2H), 2.89 (t, J = 11.2 Hz, 2H), 2.83-2.73 (m, 1H), 2.21 (s, 3H), 0.85-0.78 (m, 2H), 0.59-0.48 (m, 2H) |
| A-112 | 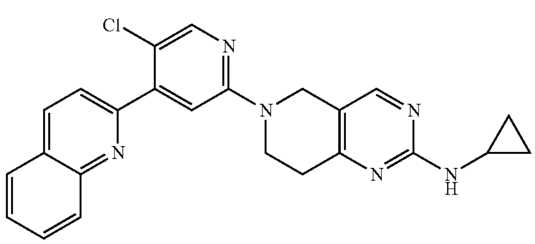 [SMILES: Clc1cnc(N2CCc3nc(NC4CC4)ncc3C2)cc1-c1ccc2ccccc2n1] | 6-(5-chloro-4-(quinolin-2-yl)pyridin-2-yl)-N-cyclopropyl-5,6,7,8-tetrahydropyrido[4,3-d]pyrimidin-2-amine | O | 428.8 | $^1$H NMR (400 MHz, CDCl$_3$) δ 8.23 (s, 1H), 8.19 (d, J = 8.4 Hz, 1H), 8.14-8.12 (m, 2H), 7.83 (d, J = 8.4 Hz, 1H), 7.71-7.68 (m, 2H), 7.55 (d, J = 7.2Hz, 1H), 6.97 (s, 1H), 5.39 (br s, 1H), 4.54 (s, 2H), 3.89 (t, J = 5.6 Hz, 2H), 2.83 (t, J = 5.6 Hz, 2H), 2.69 (br s, 1H), 0.76-0.74 (m, 2H), 0.46 (s, 2H) |

TABLE 1-continued

Selected compounds (A-1 to A-118) of the present invention.

| Example number | structure | Compound Name | Method | MS m/z (m + 1) | 1H NMR |
|---|---|---|---|---|---|
| A-113 | 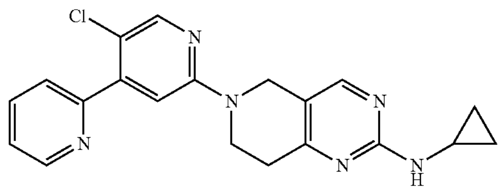 | 6-(5'-chloro-2,4'-bipyridin-2'-yl)-N-cyclopropyl-5,6,7,8-tetrahydropyrido-[4,3-d]pyrimidin-2-amine | O | 378.8 | $^1$H NMR (400 MHz, CDCl$_3$) δ 8.75 (d, J = 4.8 Hz, 1H), 8.27 (s, 1H), 8.20 (s, 1H), 7.83-7.79 (m, 1H), 7.72 (d, J = 8.0 Hz, 1H), 7.38-7.35 (m, 1H), 6.97 (s, 1H), 5.24 (s, 1H), 4.59 (s, 2H), 3.94 (t, J = 11.6 Hz, 2H), 2.89 (t, J = 11.6 Hz, 2H), 2.80-2.74 (m, 1H), 0.85-0.80 (m, 2H), 0.55-0.52 (m, 2H) |
| A-114 | 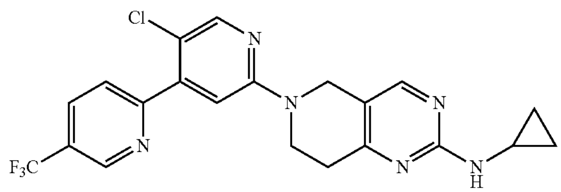 [SMILES: FC(F)(F)c1ccc(-c2cc(N3CCc4nc(NC5CC5)ncc4C3)ncc2Cl)nc1] | 6-(5'-chloro-5-(trifluoro-methyl)-2,4'-bipyridin-2'-yl)-N-cyclopropyl-5,6,7,8-tetrahydro-pyrido-[4,3-d]pyrimidin-2-amine | O | 446.8 | $^1$H NMR (400 MHz, CDCl$_3$) δ 9.04 (s, 1H), 8.75-8.71 (m, 1H), 8.65 (d, J = 2.0 Hz, 1H), 8.30 (s, 1H), 8.21 (s, 1H), 6.96 (s, 1H), 5.48 (br s, 1H), 4.60 (s, 2H), 3.95 (t, J = 12.0 Hz, 2H), 2.92 (t, J = 12.0 Hz, 2H), 2.78-2.77 (m, 1H), 0.85-0.81 (m, 2H), 0.56-0.53 (m, 2H) |
| A-115 | 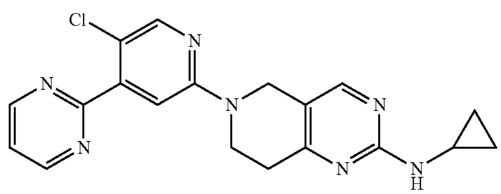 [SMILES: Clc1cnc(N2CCc3nc(NC4CC4)ncc3C2)cc1-c1ncccn1] | 6-(5-chloro-4-(pyrimidin-2-yl)pyridin-2-yl)-N-cyclopropyl-5,6,7,8-tetrahydro-pyrido-[4,3-d]pyrimidin-2-amine | P | 380.1 | $^1$H NMR (400 MHz, CDCl$_3$) δ 8.97 (d, J = 4.8 Hz, 2H), 8.31 (s, 1H), 8.20 (s, 1H), 7.37 (t, J = 4.8 Hz, 1H), 7.08 (s, 1H), 5.29 (br s, 1H), 4.59 (s, 2H), 3.94 (t, J = 6.0 Hz, 2H), 2.90 (t, J = 5.6 Hz, 2H), 2.77 (br s, 1H), 0.84-0.80 (m, 2H), 0.54 (s, 2H) |
| A-116 | 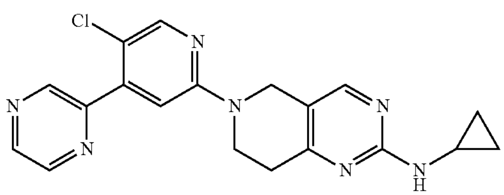 [SMILES: Clc1cnc(N2CCc3nc(NC4CC4)ncc3C2)cc1-c1cnccn1] | 6-(5-chloro-4-(pyrazin-2-yl)pyridin-2-yl)-N-cyclopropyl-5,6,7,8-tetrahydro-pyrido-[4,3-d]pyrimidin-2-amine | Q | 379.9 | $^1$H NMR (400 MHz, CDCl$_3$) δ 9.02 (s, 1H), 8.30 (s, 1H), 8.22 (s, 1H), 8.05 (d, J = 8.0 Hz, 1H), 7.88 (d, J = 8.0 Hz, 1H), 6.98 (s, 1H), 5.88 (br s, 1H), 4.62 (s, 2H), 3.95 (t, J = 11.2 Hz, 2H), 296 (t, J = 11.2 Hz, 2H), 2.83-2.77 (m, 1H), 0.87-0.83 (m, 2H), 0.60-0.56 (m, 2H) |
| A-117 | 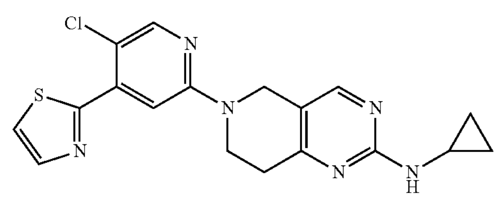 [SMILES: Clc1cnc(N2CCc3nc(NC4CC4)ncc3C2)cc1-c1nccs1] | 6-(5-chloro-4-(thiazol-2-yl)pyridin-2-yl)-N-cyclopropyl-5,6,7,8-tetrahydro-pyrido-[4,3-d]pyrimidin-2-amine | R | 384.8 | $^1$H NMR (300 MHz, CDCl$_3$) δ 8.31 (s, 1H), 8.24 (s, 1H), 8.02 (d, J = 3.0 Hz, 1H), 7.62 (s, 1H), 7.61 (d, J = 3 Hz, 1H), 5.70 (br s, 1H), 4.63 (s, 2H), 3.98 (t, J = 11.2 Hz, 2H), 2.99-2.93 (m, 2H), 2.83-2.75 (m, 1H), 0.87-0.81 (m, 2H), 0.61-0.50 (m, 2H) |
| A-118 | 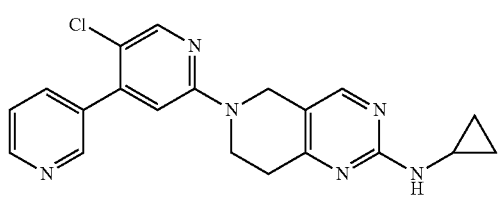 [SMILES: Clc1cnc(N2CCc3nc(NC4CC4)ncc3C2)cc1-c1cccnc1] | 6-(5'-chloro-3,4'-bipyridin-2'-yl)-N-cyclopropyl-5,6,7,8-tetrahydro-pyrido-[4,3-d]pyrimidin-2-amine | O | 378.9 | $^1$H NMR (300 MHz, CDCl$_3$) δ 8.70 (s, 1H), 8.27 (s, 1H), 8.22 (s, 1H), 7.83 (d, J = 8.1 Hz, 1H), 7.43-7.39 (m, 1H), 6.64 (s, 1H), 5.74 (br s, 1H), 4.59 (s, 2H), 3.93 (t, J = 11.2 Hz, 2H), 2.94 (t, J = 11.7 Hz, 2H), 2.82-2.76 (m, 1H), 0.87-0.81 (m, 2H), 0.59-0.54 (m, 2H) |

Biological Activities:

The primary assay is based on NIH3T3-GRE-Luc Reporter Gene Assay:

NIH3T3 cells (CRL-1658, ATCC) were maintained in DMEM (11965, Gibico) supplemented with 10% FBS (Hyclone). GRE-Luc plasmid was generated by cloning 8×Gli-1 responsive element (GRE) into the MCS of pGL4.26 (Promega). NIH3T3-GRE-Luc reporter cell lines were established by hygromycin (Invitrogen) selection after transfection with GRE-Luc luciferase reporter plasmid. Single clones were validated for the assay quality with N-terminal fragment of recombinant sonic hedgehog protein or small molecule agonist SAG (ABIN629346). Selected clone were used to monitor the Hh signaling.

The NIH3T3-GRE-Luc cells were maintained in complete culture medium (DMEM with 4 mM L-Gln, 1.5 g/L sodium bicarbonate and 4.5 g/L glucose supplemented with 100 ug/ml hygromycin and 10% FBS). When confluent, the cells were trypsinized and resuspended in assay medium (0.5% serum-containing DMEM). After 100 ul/well of cells suspension was added to the 96-well-plate (Final cell concentration is 15,000 cells/well.), cells were cultured for additional 48 hours before adding the compounds.

Compounds were serially diluted in DMSO and further diluted with assay medium. In an embodiment, 10 nM SAG was added in assay medium as the agonist of Hh signaling. After the compounds and agonist were prepared, carefully remove medium (Aspirate the medium with pipette instead of vacuum, or else the NIH3T3 cells monolayer will be detached). 100 ul of assay medium containing compound or agonist was added to the cell with care. Cell plates were incubated at 37 degree for additional 48 hours.

Following the 48 hours incubation, 40 ul/well of luciferase media (Brigh-Glo, Promega) was added to the cells. The plate was incubated at room temperature for 5 min under gentle shaking. Luminescence signal was measured with plate reader (PHERAstar FS, BMG). The potency of compounds was calculated basing on the inhibition of luminescence signaling. Curves of the IC50 measurement for standard compound A when using the primary assay are shown in FIG. 1.

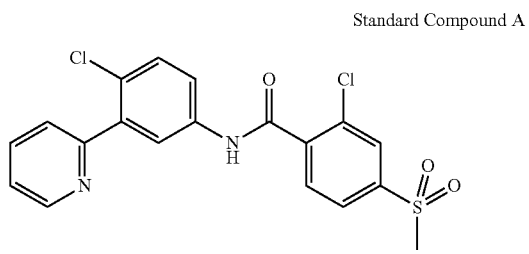 [SMILES: CS(=O)(=O)c1ccc(C(=O)Nc2ccc(Cl)c(-c3ccccn3)c2)c(Cl)c1]

Standard Compound A

The confirmation assay is based on Bodipy-Cyclopamine Binding Assay:

Bodipy-Cyclopamine binding assay is a fluorescence based assay used to analysis the binding of Smo agonists. Hek293-SMO stable clones were established by puromycin (1 ug/ml, Invitrogen) selection after transfection with SMO-HA-pLVX plasmid Hek293-SMO cells were maintained in complete culture medium (DMEM with 4 mM L-Gln, 1.5 g/L sodium bicarbonate and 4.5 g/L glucose supplemented with 100 ug/ml hygromycin and 10% FBS). The expression of SMO was validated with western blot and cell immunofluorescence. Bodipy-Cyclopamine was purchased from Toronto Research Chemicals and dissolved in methanol.

Hek293-SMO cells were plated in 96-well-plate (3340, Corning), the final cell concentration is 15,000 cells/well in 100 ul 1% serum-containing DMEM. The plates were incubated in 37 degree for additional 48 hours.

Hek293-SMO plate were washed with PBS and fixed with 4% paraformaldehyde (PFA)/PBS for 20 min at room temperature. After removing the PFA buffer, the cells were incubated with DAPI/PBS (5 ug/mL) for 10 min and followed by twice wash with PBS. After wash, cells were incubated for 2 h at room temperature in binding buffer (HBSS W/O $Ca^{2+}$ and $Mg^{2+}$) containing 100 nM bodipy-cyclopamine and compounds over a range of concentrations from 0-10 μM for competitive binding. After incubation, the cells were washed twice with the PBS. The fluorescence images were automatically captured and analyzed by a high content fluorescence imaging system (Arrayscan VTI, Thermo). GDC-0449 was used as reference compound to normalize the data. IC50 values were calculated with GraphPad Prism software using the sigmoidal dose-response function. The Ki was calculated following the Cheng-Prusoff equation, as Ki=IC50/[1+[bodipy-cyclopamine]/Kd)]. The Kd of bodipy-cyclopamine for WT-Smo is 3.5±0.8 nM.

Figure 2:
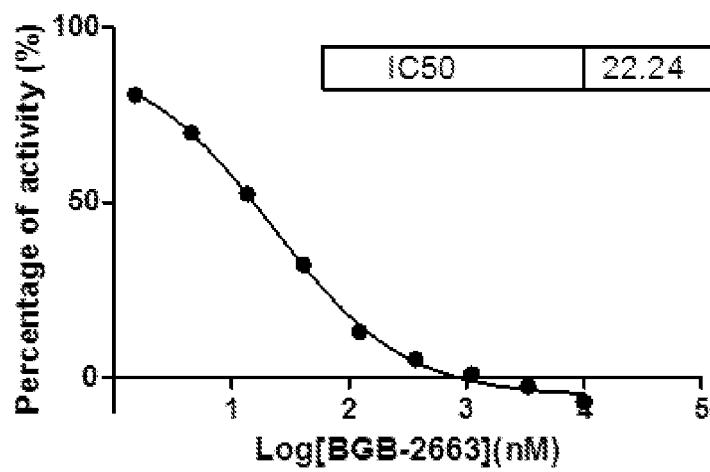
FIG. 2 depicts the IC50 curve of compound A54 of the present invention in the primary assay.
Figure 3:
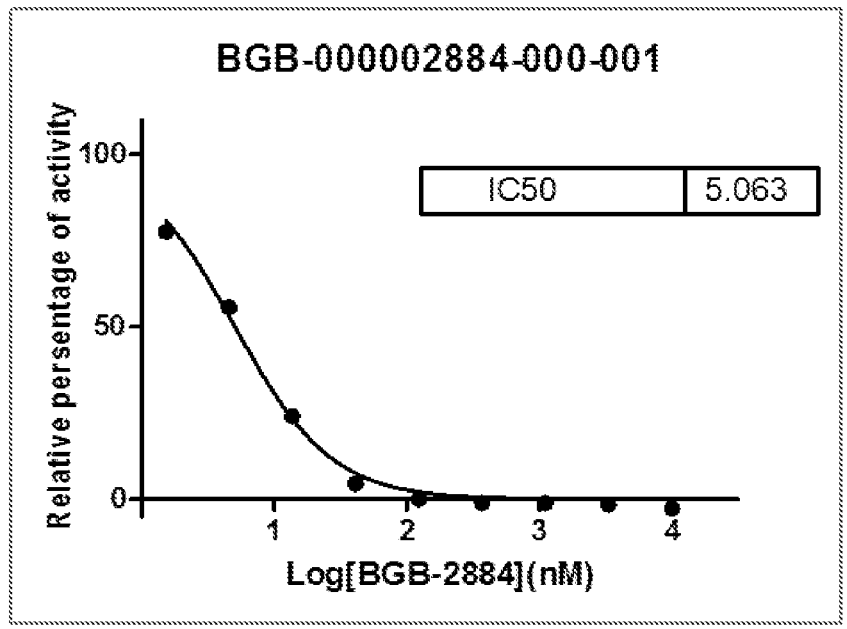
FIG. 3 depicts the IC50 curve of compound A55 of the present invention in the primary assay.
Figure 4:
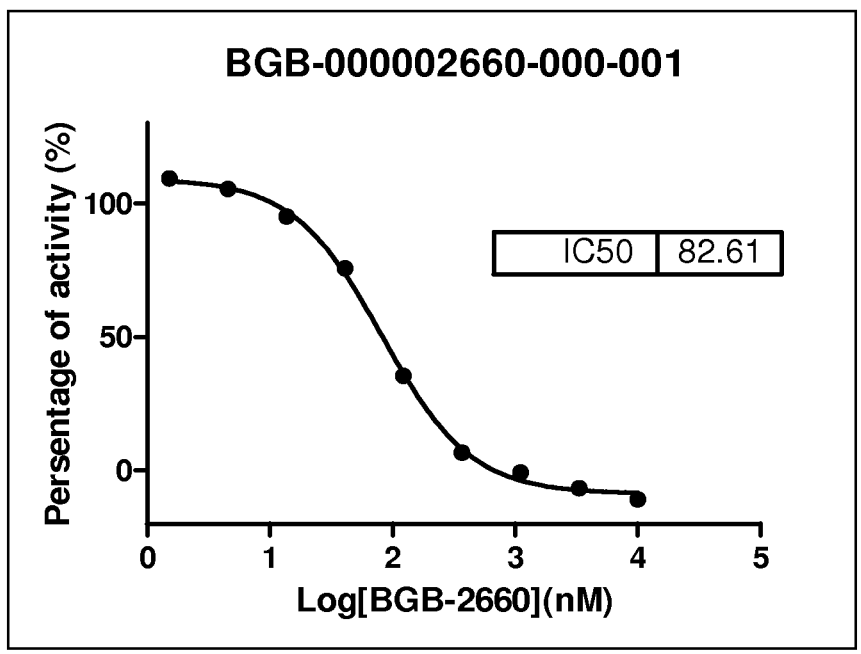
FIG. 4 depicts the IC50 curve of compound A56 of the present invention in the primary assay.

The above mentioned compounds were tested in the assays described above and the data were summarized in Table 2. The standard compound was Vismodegib and its potency was listed in column 3. The ratio was the potency of the tested compound vs the potency of Vismodegib in the same assay. Some of the tested curves were shown in FIGS. 2-4.

TABLE 2

Results of selected compounds of the present invention when tested in the confirmation essay.

| Example number | Smo IC50 (nM) | Smo IC50 (nM) (vismodegib) | ratio |
|---|---|---|---|
| A-1 | 320.6 | 26.6 | 12.0 |
| A-2 | >10000 | 7.4 | |
| A-3 | 243.5 | 16.8 | 15.2 |
| A-4 | 639.1 | 8.8 | 72.6 |
| A-5 | 1154.0 | 16.8 | 69.6 |
| A-6 | 1262.0 | 14.07 | 89.7 |
| A-7 | 655.8 | 8.8 | 72.6 |
| A-8 | 2011.0 | 8.8 | 228 |
| A-9 | >1000 | 19.6 | |
| A-10 | >1000 | 19.7 | |
| A-11 | 676.0 | 19.7 | 34.3 |
| A-12 | >1000 | 101.1 | |
| A-13 | >1000 | 184.8 | |
| A-14 | >1000 | 184.8 | |
| A-15 | 588.6 | 44.6 | 13 |
| A16 | 441.8 | 44.6 | 10 |
| A-17 | >1000 | 44.6 | |
| A-18 | >1000 | 44.6 | |
| A-19 | 311.3 | 44.6 | 7.0 |
| A-20 | 507.2 | 44.6 | 11 |
| A-21 | >1000( | 44.6 | |
| A-22 | 768.2 | 101.1 | 7.6 |
| A-23 | 363.4 | 101.1 | 3.6 |
| A-24 | 58.3 | 101.1 | 0.56 |
| A-25 | 100.7 | 101.1 | 1.0 |
| A-26 | 71 | 101.1 | 0.7 |
| A-27 | 422.7 | 70.8 | 6.0 |
| A-28 | 126.8 | 101.1 | 1.3 |
| A-29 | 169.5 | 101.1 | 1.7 |
| A-30 | 69.7 | 101.1 | 0.69 |
| A-31 | 54.8 | 101.1 | 0.54 |
| A-32 | 86.7 | 10.1 | 0.86 |
| A-33 | 447.3 | 70.8 | 3.7 |
| A-34 | 370.7 | 70.8 | 5.2 |
| A-35 | 259.8 | 70.8 | 3.7 |

TABLE 2-continued

Results of selected compounds of the present invention when tested in the confirmation essay.

| Example number | Smo IC50 (nM) | Smo IC50 (nM) (vismodegib) | ratio |
|---|---|---|---|
| A-36 | 564.9 | 70.8 | 8.0 |
| A-37 | 486.8 | 70.8 | 6.9 |
| A-38 | >1000 | 70.8 | |
| A-39 | 134.3 | 70.8 | 1.9 |
| A-40 | 150.9 | 70.8 | 2.1 |
| A-41 | 173.2 | 70.8 | 2.5 |
| A-42 | 189.7 | 184.8 | 1.0 |
| A-43 | 200.8 | 184.8 | 1.1 |
| A-44 | >1000 | 44.6 | |
| A-45 | >1000 | 44.6 | |
| A46 | 157.9 | 44.6 | 3.5 |
| A-47 | 88.3 | 44.6 | 2.0 |
| A-48 | 329.6 | 184.8 | 1.8 |
| A-49 | ND | ND | |
| A-50 | 231.5 | 26.6 | 8.71 |
| A-51 | 16.8 | 12 | 1.4 |
| A-52 | 5.4 | 8.8 | 0.61 |
| A-53 | 24.9 | 12 | 2.1 |
| A-54 | 22.9 | 16.8 | 1.4 |
| A-55 | 5.1 | 8.8 | 0.58 |
| A-56 | 48.7 | 16.8 | 2.9 |
| A-57 | 11.1 | 19.6 | 0.57 |
| A-58 | 59.8 | 19.6 | 3.1 |
| A-59 | 48.8 | 19.6 | 2.5 |
| A-60 | 18 | 19.6 | 0.92 |
| A-61 | 14.1 | 19.6 | 0.72 |
| A-62 | 51.1 | 19.6 | 2.6 |
| A-63 | 87.6 | 19.7 | 4.4 |
| A-64 | 500.1 | 101.1 | 4.9 |
| A-65 | 85.3 | 80.6 | 1.1 |
| A-66 | 85.1 | 80.6 | 1.1 |
| A-67 | 206.7 | 80.6 | 2.6 |
| A-68 | 163.4 | 101.1 | 1.6 |
| A-69 | 97.8 | 80.6 | 1.2 |
| A-70 | 117.3 | 101.1 | 1.2 |
| A-71 | 77.1 | 80.6 | 0.96 |
| A-72 | 283 | 80.6 | 3.5 |
| A-73 | 84 | 80.6 | 1.0 |
| A-74 | 574.9 | 101.1 | 5.7 |
| A-75 | 257.1 | 70.8 | 3.6 |
| A-76 | 146.7 | 70.8 | 2.1 |
| A-77 | 92.9 | 70.8 | 1.3 |
| A-78 | 124.9 | 70.8 | 1.8 |
| A-79 | 187.9 | 70.8 | 2.7 |
| A-80 | 28.1 | 70.8 | 0.40 |
| A-81 | 167.2 | 70.8 | 2.4 |
| A-82 | 105.2 | 70.8 | 1.5 |
| A-83 | 211.3 | 70.8 | 3.0 |
| A-84 | ND | ND | |
| A-85 | ND | ND | |
| A-86 | ND | ND | |
| A-87 | ND | ND | |
| A-88 | ND | ND | |
| A-89 | >1000 | 45.1 | |
| A-90 | 407.5 | 184.8 | 2.2 |
| A-91 | >1000 | 184.8 | |
| A-92 | 961.4 | 184.8 | 5.2 |
| A-93 | 103.6 | 184.8 | 0.56 |
| A-94 | ND | ND | |
| A-95 | ND | ND | |
| A-96 | 169.2 | 44.6 | 3.8 |
| A-97 | 84.1 | 45.1 | 1.9 |
| A-98 | 835.2 | 44.6 | 19 |
| A99 | 24.8 | 44.6 | 0.57 |
| A-100 | ND | ND | |
| A-101 | 252.6 | 44.6 | 5.7 |
| A-102 | ND | ND | |
| A-103 | ND | ND | |
| A-104 | 76.0 | 44.6 | 1.7 |
| A-105 | 271.7 | 44.6 | 6.1 |
| A-106 | ND | ND | |
| A-107 | ND | ND | |
| A-108 | ND | ND | |
| A-109 | ND | ND | |
| A-110 | >1000 | 45.1 | |
| A-111 | 82.9 | 45.1 | 1.8 |
| A-112 | 112.6 | 45.1 | 2.5 |
| A-113 | 469.7 | 45.1 | 10.4 |
| A-114 | >1000 | 45.1 | |
| A-115 | >1000 | 44.6 | |
| A-116 | 234.8 | 45.1 | 5.2 |
| A-117 | 169 | 184.8 | 0.91 |
| A-118 | >1000 | 184.4 | |

What is claimed is:

1. A compound of Formula I-a:

or a pharmaceutically acceptable salt, or solvate thereof, wherein $A^4$ is C—$R^7$;
$R^3$ and $R^4$ are independently H or methyl;
$R^5$ and $R^6$ are independently H or methyl;
V' is C—$R^7$;
V and $V^6$ are N;
U is $R^7$ is independently selected from the group consisting of hydrogen, halogen, haloalkyl, CN, cyanoalkyl, trifluoromethyl, alkyl, alkenyl, alkenyl, amino, oxygen, hydroxyl, sulfur, hydrosulfuryl, alkoxy, acyloxy, acylamino, urea, carbamoyloxy, thiourea, sulfone, sulfoxide, sulfonamide, azido, alkylalkenyl, alkylalkynyl, alkylamino, alkylacyloxy, alkylsulphonyl, alkylsulfinyl, alkylsulfonamide, azidoalkyl, cycloalkyl, cycloalkenyl, 3-12 membered heterocycle, aryl, and 5-12 membered heteroaryl; and $R^{20}$ to $R^{22}$ are independently selected from the group consisting of hydrogen, halogen, haloalkyl, alkyl, trifluoromethyl, alkyl sulfonyl, alkylsulfinyl, alkylsulfonamide, sulfonamide, and alkylacyloxy.

2. The compound of claim 1, wherein the compound is according to Formula I-d:

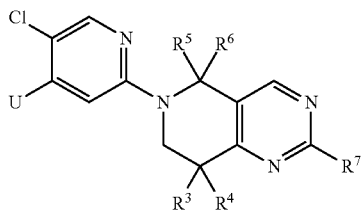

wherein $R^3$ and $R^4$ are independently H or methyl; and $R^5$ and $R^6$ are independently H or methyl.

3. A compound according to Formula I-g:

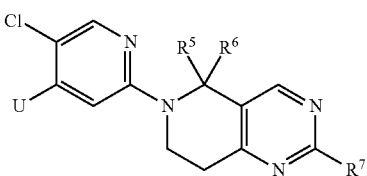

wherein $R^5$ and $R^6$ are independently H or methyl;
$R^7$ is selected from the group consisted of hydrogen, halogen, haloalkyl, CN, cyanoalkyl, trifluoromethyl, alkyl, alkenyl, alkynyl, amino, oxygen, hydroxyl, sulfur, hydrosulfuryl, alkoxy, acyloxy, acylamino, urea, carbamoyloxy, thiourea, sulfone, sulfoxide, sulfonamide, azido, alkylalkenyl, alkylalkynyl, alkylamino, alkylacyloxy, alkylsulphonyl, alkylsulfinyl, alkylsulfonamide, azidoalkyl, cycloalkyl, cycloalkenyl, 3-12 membered heterocycle, aryl, and 5-12 membered heteroaryl; and
U is a 5-12 membered heteroaryl.

4. The compound of claim 3, wherein $R^7$ is selected from the group consisting of

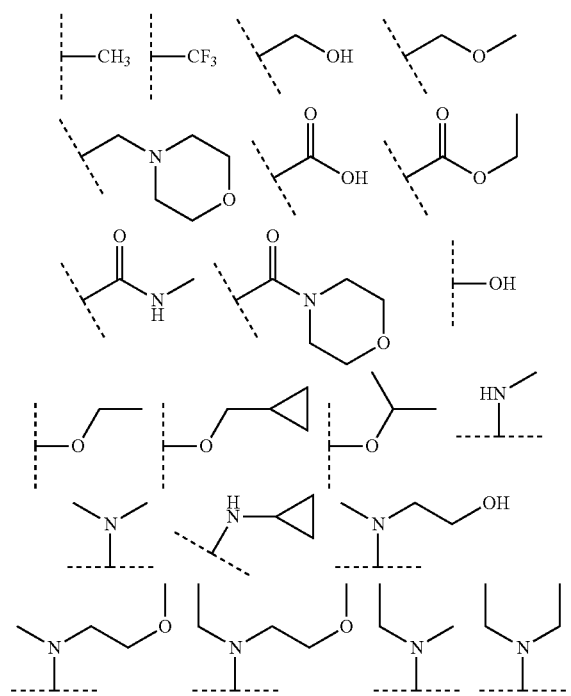

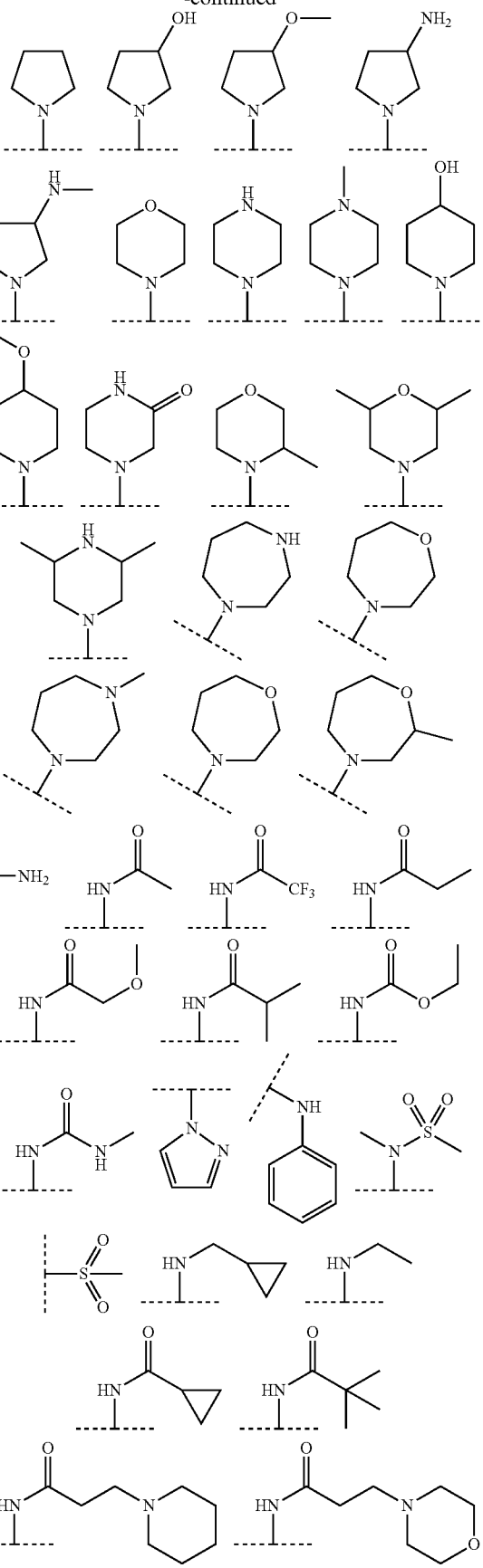

-continued

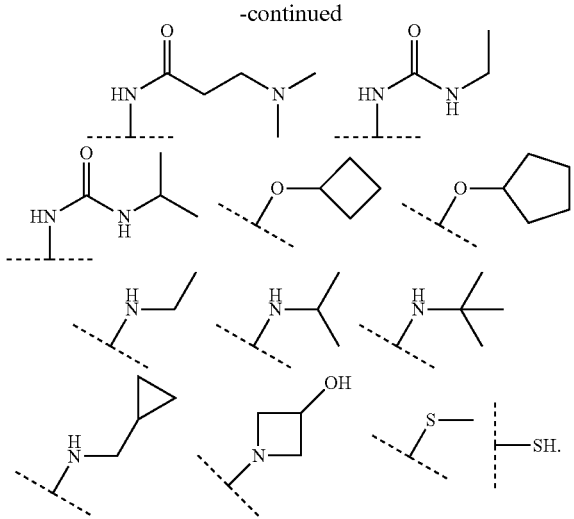

5. The compound of claim 4, wherein U is selected from a group consisting of pyridine, pyrazine, quinoline, and thiazole, with 0-2 substituents.

6. The compound of claim 5, wherein U is

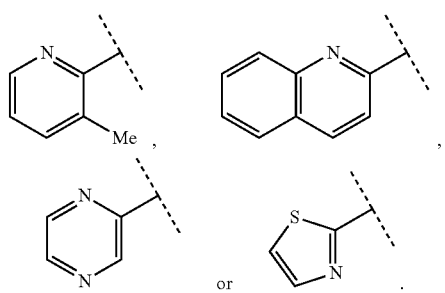

7. A pharmaceutical composition comprising a compound of formula I-a in claim 1 and a pharmaceutically acceptable carrier.

8. A method for inhibiting an activation of a hedgehog-patched pathway in a patient diagnosed with a hyperproliferative disorder consisting of prostate cancer, glioblastoma, medulloblastoma, basal cell carcinoma, non-small cell lung cancer, cervical carcinoma, pancreas carcinoma, breast carcinoma, stomach carcinoma, dermal carcinoma, kidney cancer, and leukemia, comprising administering to the patient a composition comprising a hedgehog pathway inhibitor in an effective amount to reduce the activation of the hedgehog-patched pathway in a cell of the patient, wherein the hedgehog pathway inhibitor is a compound of formula I-a:

I-a

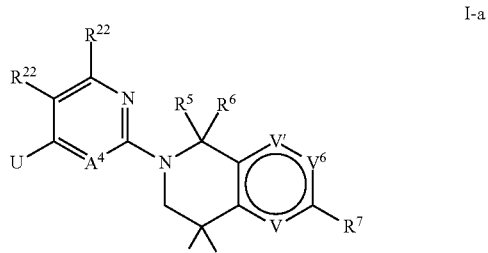

or a pharmaceutically acceptable salt, or solvate thereof,
wherein $A^4$ is C—$R^7$;
$R^3$, $R^4$, $R^5$ and $R^6$ are independently H or methyl;
V and $V^6$ are N;
V' is C—$R^7$;
U is

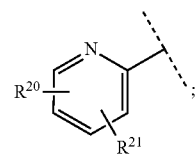

$R^7$ is independently selected from the group consisting of hydrogen, halogen, haloalkyl, CN, cyanoalkyl, trifluoromethyl, alkyl, alkenyl, alkynyl, amino, oxygen, hydroxyl, sulfur, hydrosulfuryl, alkoxy, acyloxy, acylamino, urea, carbamoyloxy, thiourea, sulfone, sulfoxide, sulfonamide, azido, alkylalkenyl, alkylalkynyl, alkylamino, alkylacyloxy, alkylsulphonyl, alkylsulfinyl, alkylsulfonamide, azidoalkyl, cycloalkyl, cycloalkenyl, 3-12 membered heterocycle, aryl, and 5-12 membered heteroaryl; and $R^{20}$ to $R^{22}$ are independently selected from the group consisting of hydrogen, halogen, haloalkyl, alkyl, trifluoromethyl, alkylsulfonyl, alkylsulfinyl, alkylsulfonamide, sulfonamide, and alkylacyloxy.

\* \* \* \* \*